US012497438B2

(12) United States Patent
Bloom

(10) Patent No.: US 12,497,438 B2
(45) Date of Patent: Dec. 16, 2025

(54) COMPOUNDS

(71) Applicant: IP2IPO Innovations Limited, London (GB)

(72) Inventor: Stephen Robert Bloom, London (GB)

(73) Assignee: IP2IPO Innovations Limited, London (GB)

(*) Notice: Subject to any disclaimer, the term of this patent is extended or adjusted under 35 U.S.C. 154(b) by 0 days.

(21) Appl. No.: 19/308,016

(22) Filed: Aug. 22, 2025

(65) Prior Publication Data

US 2025/0368710 A1 Dec. 4, 2025

Related U.S. Application Data

(63) Continuation of application No. 18/266,571, filed as application No. PCT/GB2021/053249 on Dec. 10, 2021.

(30) Foreign Application Priority Data

Dec. 11, 2020 (GB) ..................................... 2019588
Jul. 27, 2021 (GB) ..................................... 2110809

(51) Int. Cl.
*C07K 14/605* (2006.01)
*A61K 38/26* (2006.01)
*A61P 3/04* (2006.01)

(52) U.S. Cl.
CPC ............ *C07K 14/605* (2013.01); *A61K 38/26* (2013.01); *A61P 3/04* (2018.01)

(58) Field of Classification Search
CPC .......... C07K 14/605; A61K 38/26; A61P 3/04
See application file for complete search history.

(56) References Cited

U.S. PATENT DOCUMENTS

| | | | |
|---|---|---|---|
| 4,179,337 A | 12/1979 | Davis et al. | |
| 5,700,486 A | 12/1997 | Canal et al. | |
| 5,936,092 A | 8/1999 | Shen et al. | |
| 5,939,380 A | 8/1999 | Wang | |
| 5,993,414 A | 11/1999 | Haller | |
| 6,093,692 A | 7/2000 | Shen et al. | |
| 6,225,445 B1 | 5/2001 | Shen et al. | |
| 6,436,091 B1 | 8/2002 | Harper et al. | |
| 6,447,743 B1 | 9/2002 | Devic et al. | |
| 2011/0097751 A1* | 4/2011 | Nicolaou | G01N 33/5008 435/7.1 |

FOREIGN PATENT DOCUMENTS

| | | | |
|---|---|---|---|
| CN | 104211801 A | 12/2014 | |
| WO | WO-0104156 A1 | 1/2001 | |
| WO | WO-2005021022 A2 | 3/2005 | |
| WO | WO-2006097538 A1 | 9/2006 | |
| WO | WO-2008081418 A1 | 7/2008 | |
| WO | WO-2009030771 A1 | 3/2009 | |
| WO | WO-2009035540 A2 | 3/2009 | |
| WO | WO-2010120476 A2 | 10/2010 | |
| WO | WO-2011134471 A1 | 11/2011 | |
| WO | WO-2013004983 A1 | 1/2013 | |
| WO | WO-2015132599 A1 | 9/2015 | |
| WO | WO-2017178829 A1 | 10/2017 | |
| WO | WO-2022123271 A1 | 6/2022 | |

OTHER PUBLICATIONS

Buchwald, H., et al.; "Long-term, continuous intravenous heparin administration by an implantable infusion pump in ambulatory patients with recurrent venous thrombosis," Surgery; 88(4):507-516 (1980).
International Preliminary Report on Patentability, Chapter II, Patent Cooperation Treaty Application No. PCT/GB2021/053249, dated Feb. 6, 2023, 9 pages.
International Search Report and Written Opinion, Patent Cooperation Treaty Application No. PCT/GB2021/053249, dated Mar. 22, 2022, 14 pages.
Jameson & Wolf, "The antigenic index: a novel algorithm for predicting antigenic determinants," Comput. Appl. Biosci., vol. 4(1), 1988, pp. 181-186.
Jequier, E., "Energy, obesity, and body weight standards," American Journal of Clinical Nutrition, vol. 45, May 1987, pp. 1035-1036.
Kolaskar & Tongaonkar, "A semi-empirical method for prediction of antigenic determinants on protein antigens," FEBS Lett., vol. 10, No. 276(1-2), Dec. 1990, pp. 172-174.
Langer, R., "New methods of drug delivery," Science. Sep. 28, 1990; 249(4976):1527-33.
Lyznicki, J. M. et al., "Obesity: assessment and management in primary care," American Family Physician, vol. 63, No. 11, Jun. 2001, pp. 2185-2196.
Pellequer & Westhof, "PREDITOP: A program for antigenicity prediction," J. Mol. Graph., vol. 11, No. 3, 1993, pp. 204-210 (10 pages total).
Saudek, C.D., et al.; "A preliminary trial of the programmable implantable medication system for insulin delivery," N Engl J Med.; 321(9):574-579 (1989).
Sefton, M.V., "Implantable pumps," Crit Rev Biomed Eng., 14(3):201-240 (1987).
Teramoto, S. et al., "Exendin-4, a glucagon-like peptide-1 receptor agonist, provides neuroprotection in mice transient focal cerebral ischemia," Journal of Cerebral Blood Flow & Metabolism, vol. 31, Apr. 13, 2011, pp. 1696-1705.

(Continued)

*Primary Examiner* — Jeanette M Lieb
(74) *Attorney, Agent, or Firm* — COOLEY LLP

(57) ABSTRACT

The disclosure provides novel compounds which are peptide hormone analogues, and which are useful in treating disorders such as diabetes and obesity. The compounds of the general sequence recited in the specification possess a tailored profile with regards to potency properties at the glucagon and GLP-1 receptors. With regard to in vivo properties, administration of example peptides of the invention have been shown, in animal models, to result in increased weight loss. Preferred compounds achieve this without reducing food intake significantly.

24 Claims, 66 Drawing Sheets

Specification includes a Sequence Listing.

(56) References Cited

OTHER PUBLICATIONS

Timmers, L., et al., "Exenatide reduces infarct size and improves cardiac function in a porcine model of ischemia and reperfusion injury," Journal of the American College of Cardiology, vol. 53, Issue 6, Feb. 10, 2009, pp. 501-510.

Wang, Y. et al., "Parenteral Formulations of Proteins and Peptides: Stability and Stabilizers," Journal of Parenteral Science and Technology, Technical Report No. 10, Supplement 1988, vol. 42, No. 2S, pp. S2-S25.

* cited by examiner

Figure 1

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 1 | 5883 | 1 | dupl 6149 | His | AIB | His | Gly | Thr | Phe | Thr | Ser | Asp | Leu | Ser | Lys | Gln | Leu | Glu | Glu | Glu |
| 2 | 6033 | 2 | | His | AIB | His | Gly | Thr | Phe | Thr | Ser | Asp | Leu | Ser | Lys | Gln | Leu | Glu | Glu | Glu |
| 3 | 6036 | 3 | | His | AIB | His | Gly | Thr | Phe | Thr | Ser | Asp | Leu | Ser | Lys | Gln | Leu | Glu | Glu | Glu |
| 4 | 6037 | 4 | | His | AIB | His | Gly | Thr | Phe | Thr | Ser | Asp | Leu | Ser | Lys | Gln | Leu | Glu | Glu | Glu |
| 5 | 6038 | 5 | | His | AIB | His | Gly | Thr | Phe | Thr | Ser | Asp | Leu | Ser | Lys | Gln | Leu | Glu | Glu | Glu |
| 6 | 6039 | 6 | | His | AIB | His | Gly | Thr | Phe | Thr | Ser | Asp | Leu | Ser | Lys | Gln | Leu | Glu | Glu | Glu |
| 7 | 6040 | 7 | | His | AIB | His | Gly | Thr | Phe | Thr | Ser | Asp | Leu | Ser | Lys | Gln | Leu | Glu | Glu | Glu |
| 8 | 6041 | 8 | | His | AIB | His | Gly | Thr | Phe | Thr | Ser | Asp | Leu | Ser | Lys | Gln | Leu | Glu | Glu | Glu |
| 9 | 6043 | 9 | | His | AIB | His | Gly | Thr | Phe | Thr | Ser | Asp | Leu | Ser | Lys | Gln | Leu | Glu | Glu | Glu |
| 10 | 6044 | 10 | | His | AIB | His | Gly | Thr | Phe | Thr | Ser | Asp | Leu | Ser | Lys | Gln | Leu | Glu | Glu | Glu |
| 11 | 6060 | 11 | | His | AIB | His | Gly | Thr | Phe | Thr | Ser | Asp | Leu | Ser | Lys | Gln | Leu | Glu | Glu | Glu |
| 12 | 6061 | 12 | | His | AIB | His | Gly | Thr | Phe | Thr | Ser | Asp | Leu | Ser | Lys | Gln | Leu | Glu | Glu | Glu |
| 13 | 6063 | 13 | | His | AIB | His | Gly | Thr | Phe | Thr | Ser | Asp | Leu | Ser | Lys | Gln | Leu | Glu | Glu | Glu |
| 14 | 6082 | 14 | | His | AIB | His | Gly | Thr | Phe | Thr | Ser | Asp | Leu | Ser | Lys | Gln | Leu | Glu | Glu | Glu |
| 15 | 6083 | 15 | | His | AIB | His | Gly | Thr | Phe | Thr | Ser | Asp | Leu | Ser | Lys | Gln | Leu | Glu | Glu | Glu |
| 16 | 6084 | 16 | | His | AIB | His | Gly | Thr | Phe | Thr | Ser | Asp | Leu | Ser | Lys | Gln | Leu | Glu | Glu | Glu |
| 17 | 6087 | 17 | | His | AIB | His | Gly | Thr | Phe | Thr | Ser | Asp | Leu | Ser | Lys | Gln | Leu | Glu | Glu | Glu |
| 18 | 6088 | 18 | | His | AIB | His | Gly | Thr | Phe | Thr | Ser | Asp | Leu | Ser | Lys | Gln | Leu | Glu | Glu | Glu |
| 19 | 6089 | 19 | | His | AIB | His | Gly | Thr | Phe | Thr | Ser | Asp | Leu | Ser | Lys | Gln | Leu | Glu | Glu | Glu |
| 20 | 6094 | 20 | | His | AIB | His | Gly | Thr | Phe | Thr | Ser | Asp | Leu | Ser | Lys | Gln | Leu | Glu | Glu | Glu |
| 21 | 6095 | 21 | | His | AIB | His | Gly | Thr | Phe | Thr | Ser | Asp | Leu | Ser | Lys | Gln | Leu | Glu | Glu | Glu |
| 22 | 6149 | 22 | dupl 5883 | His | AIB | His | Gly | Thr | Phe | Thr | Ser | Asp | Leu | Ser | Lys | Gln | Leu | Glu | Glu | Glu |
| 23 | 6155 | 23 | | Phe | AIB | His | Gly | Thr | Phe | Thr | Ser | Asp | Leu | Ser | Lys | Gln | Leu | Glu | Glu | Glu |
| 24 | 6157 | 24 | | His | AIB | His | Gly | Thr | Phe | Thr | Ser | Asp | Leu | Ser | Lys | Gln | Leu | Glu | Glu | Glu |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | His |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | His |
| Ala | Val | Arg | Glu | Phe | Ile | Glu | Trp | Leu | Lys | Asn | Gly | Gly | Pro | Ser | Ser | Gly | Ala | | Pro | Pro | Pro | | | Lys | Asn | |
| Ala | Val | Arg | Glu | Phe | Ile | Glu | Trp | Leu | Lys | His | Gly | Gly | Pro | Ser | Ser | Gly | Ala | | Pro | Pro | Pro | | | Lys | Asn | |
| Ala | Val | Arg | Glu | Phe | Ile | Glu | Trp | Leu | Lys | Gln | Gly | Gly | Pro | Ser | Ser | Gly | Ala | | Pro | Pro | Pro | | | Lys | Asn | |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | |
| Arg | Val | Arg | Glu | Phe | Ile | Glu | Trp | Leu | Lys | Asn | Gly | Gly | Pro | Ser | Ser | Gly | Ala | | Pro | Pro | Pro | | | Lys | Asn | |
| Ala | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Ala | Val | Arg | Glu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Glu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Glu | Phe | Ile | Glu | Trp | Leu | Lys | Asn | Gly | Gly | Pro | Ser | Ser | Gly | Ala | | Pro | Pro | Pro | Gly | | Lys | | His |
| Arg | Val | Arg | Glu | Phe | Ile | Glu | Trp | Leu | Lys | His | Gly | Gly | Pro | Ser | Ser | Gly | Ala | | Pro | Pro | Pro | Gly | | Lys | | |
| Arg | Val | His | Glu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | His | Gly | Gly | Pro | Ser | His | Gly | Ala | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Asn | Gly | Gly | Pro | Ser | His | Gly | His | | Pro | Pro | Pro | Gly | | Lys | | |
| Arg | Val | Arg | Leu | Phe | Ile | Glu | Trp | Leu | Lys | Asn | Gly | Gly | Pro | Ser | His | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | His | | Pro | Pro | Pro | Gly | | Lys | | |
| Ala | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | His |
| Ala | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | His |
| Arg | Val | Arg | Leu | Phe | Ile | Glu | Trp | Leu | Lys | Asn | Gly | Gly | Pro | Ser | Ser | Gly | His | | Pro | Pro | Pro | | | Lys | Asn | His |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 16 | 1 | 4 | 14 | 7 | 1.8 | 1 | 30 |
| 16 | 2 | 2 | 12 | 4 | 1.4 | | |
| 18 | 3 | 1 | 4 | 2 | 11.5 | | |
| 18 | 4 | 1 | 7 | 2 | 15.9 | | |
| 18 | 5 | 1 | 6 | 2 | 13.9 | | |
| 18 | 6 | 3 | 13 | 7 | 3.7 | | |
| 18 | 7 | 1 | 5 | 2 | 6.6 | | |
| 18 | 8 | 4 | 15 | 6 | 3.3 | | |
| 18 | 9 | 1 | 4 | 3 | 6.8 | | |
| 18 | 10 | 1 | 10 | 2 | 4.5 | | |
| 18 | 11 | 1 | 6 | 2 | 5 | | |
| 18 | 12 | 1 | 4 | 2 | 6 | | |
| 18 | 13 | 1 | 3 | 2 | 6.7 | | |
| 18 | 14 | 2 | 15 | 6 | 3.7 | | |
| 18 | 15 | 7 | 13 | 8 | 3 | 3 | 77 |
| 18 | 16 | 1 | 10 | 5 | 3 | | |
| 18 | 17 | 1 | 10 | 2 | 4.1 | | |
| 18 | 18 | 1 | 10 | 4 | 4 | 1 | 57 |
| 18 | 19 | 1 | 11 | 2 | 3.5 | | |
| 18 | 20 | 1 | 15 | 2 | 4.7 | | |
| 18 | 21 | 4 | 15 | 4 | 2.8 | | |
| 16 | 22 | | | 3 | 2 | | |
| 16 | 23 | | | 1 | 59 | | |
| 16 | 24 | 1 | 15 | 5 | 1.3 | 1 | 31 |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 25 | 6158 | 25 | | His | AIB | His | Gly | Thr | Phe | Thr | Ser | Asp | Leu | Ser | Lys | Gln | Leu | Glu | Glu | Glu |
| 26 | 6159 | 26 | | His | AIB | His | Gly | Thr | Phe | Thr | Ser | Asp | Leu | Ser | Lys | Gln | Leu | Glu | Glu | Glu |
| 27 | 6160 | 27 | | His | AIB | His | Gly | Thr | Phe | Thr | Ser | Asp | Leu | Ser | Lys | Gln | Leu | Glu | Glu | Glu |
| 28 | 6161 | 28 | | His | AIB | His | Gly | Thr | Phe | Thr | Ser | Asp | Leu | Ser | Lys | Gln | Leu | Glu | Glu | Glu |
| 29 | 6162 | 29 | | His | AIB | His | Gly | Thr | Phe | Thr | Ser | Asp | Leu | Ser | Lys | Gln | Leu | Glu | Glu | Glu |
| 30 | 6163 | 30 | | His | AIB | His | Gly | Thr | Phe | Thr | Ser | Asp | Leu | Ser | Lys | Gln | Leu | Glu | Glu | Glu |
| 31 | 6168 | 31 | | His | AIB | His | Gly | Thr | Phe | Thr | Ser | Asp | Leu | Ser | Lys | Gln | Leu | Glu | Glu | Glu |
| 32 | 6170 | 32 | | His | AIB | His | Gly | Thr | Phe | Thr | Ser | Asp | Leu | Ser | Lys | Gln | Leu | Glu | Glu | Glu |
| 33 | 6173 | 33 | | His | AIB | His | Gly | Thr | Phe | Thr | Ser | Asp | Leu | Ser | Lys | Gln | Leu | Glu | Glu | Glu |
| 34 | 6191 | 34 | dupl 6341 + 6366 + 6458 | His | AIB | His | Gly | Thr | Phe | Thr | Ser | Asp | Leu | Ser | Lys | Gln | Leu | Glu | Glu | Lys |
| 35 | 6199 | 35 | | His | AIB | His | Gly | Thr | Phe | Thr | Ser | Asp | Leu | Ser | Lys | Gln | Leu | Glu | Glu | Lys |
| 36 | 6205 | 36 | dupl 6406 + 6470 | His | AIB | His | Gly | Thr | Phe | Thr | Ser | Asp | Leu | Ser | Lys | Gln | Leu | Glu | Glu | Lys |
| 37 | 6207 | 37 | | His | AIB | His | Gly | Thr | Phe | Thr | Ser | Asp | Leu | Ser | Lys | Gln | Leu | Glu | Glu | Lys |
| 38 | 6211 | 38 | | His | AIB | His | Gly | Thr | Phe | Thr | Ser | Asp | Leu | Ser | Lys | Gln | Leu | Glu | Glu | Lys |
| 39 | 6225 | 39 | | His | AIB | His | Gly | Thr | Phe | Thr | Ser | Asp | Leu | Ser | Lys | Gln | Leu | Glu | Glu | Glu |
| 40 | 6226 | 40 | | His | AIB | His | Gly | Thr | Phe | Thr | Ser | Asp | Leu | Ser | Lys | Gln | Leu | Glu | Glu | Glu |
| 41 | 6227 | 41 | | His | AIB | His | Gly | Thr | Phe | Thr | Ser | Asp | Leu | Ser | Lys | Gln | Leu | Glu | Glu | Glu |
| 42 | 6237 | 42 | dupl 6342 | His | AIB | His | Gly | Thr | Phe | Thr | Ser | Asp | Leu | Ser | Lys | Gln | Leu | Glu | Glu | Lys |
| 43 | 6238 | 43 | | His | AIB | His | Gly | Thr | Phe | Thr | Ser | Asp | Leu | Ser | Lys | Gln | Leu | Glu | Glu | Lys |
| 44 | 6239 | 44 | dupl 6578 | His | AIB | His | Gly | Thr | Phe | Thr | Ser | Asp | Leu | Ser | Lys | Gln | Leu | Glu | Glu | Lys |
| 45 | 6240 | 45 | | His | AIB | His | Gly | Thr | Phe | Thr | Ser | Asp | Leu | Ser | Lys | Gln | Leu | Glu | Glu | Glu |
| 46 | 6243 | 46 | | His | AIB | His | Gly | Thr | Phe | Thr | Ser | Asp | Leu | Ser | Lys | Gln | Leu | Glu | Glu | Lys |
| 47 | 6245 | 47 | | His | AIB | His | Gly | Thr | Phe | Thr | Ser | Asp | Leu | Ser | Lys | Gln | Leu | Glu | Glu | Glu |
| 48 | 6249 | 48 | | His | AIB | His | Gly | Thr | Phe | Thr | Ser | Asp | Leu | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Asn | Gly | Gly | Pro | Ser | Ser | Gly | Lys | | Pro | Pro | Pro | | | Lys | Asn | His |
| Arg | Val | Arg | Leu | Phe | Ile | Glu | Trp | Leu | Lys | Asn | Gly | Gly | Pro | Ser | His | Gly | Ala | | Pro | Pro | Pro | | | Lys | Asn | His |
| Arg | Val | Arg | Leu | Phe | Ile | Glu | Trp | Leu | Lys | Asn | Gly | Gly | Pro | Ser | His | Gly | His | | Pro | Pro | Pro | | | Lys | Asn | His |
| Ala | Val | Arg | Glu | Phe | Ile | Glu | Trp | Leu | Lys | Asn | Gly | Gly | Pro | Ser | His | Gly | His | | Pro | Pro | Pro | | | Lys | Asn | His |
| Arg | Val | Arg | Leu | Phe | Ile | Glu | Trp | Leu | Lys | Asn | Gly | Gly | Pro | Ser | His | Gly | His | | Pro | Pro | Pro | | | Lys | | |
| Arg | Val | Arg | Glu | Phe | Ile | Glu | Trp | Leu | Lys | Asn | Gly | Gly | Pro | Ser | His | Gly | His | | Pro | Pro | Pro | | | Lys | | |
| Arg | Val | Arg | Leu | Phe | Ile | Glu | Trp | Leu | Lys | Asn | Gly | Gly | Pro | Ser | His | Gly | His | | Pro | Pro | Pro | | | Lys | | |
| Ala | Val | Arg | Leu | Phe | Ile | Glu | Trp | Leu | Lys | Asn | Gly | Gly | Pro | Ser | His | Gly | His | | Pro | Pro | Pro | | | Lys | | |
| Ala | Val | Arg | Leu | Phe | Ile | Glu | Trp | Leu | Lys | Asn | Gly | Gly | Pro | Ser | His | Gly | His | | Pro | Pro | Pro | | | Lys | Asn | His |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Ala | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | His |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | Asn | His |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | Asn | |
| Ala | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | Asn | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | Asn | |
| Arg | Val | Arg | Leu | Phe | Ile | Glu | Trp | Leu | Lys | Asn | Gly | Gly | Pro | Ser | Ser | Gly | His | | Pro | Pro | Pro | Gly | | Lys | Asn | |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | | |
| Arg | Val | Arg | Leu | Phe | Ile | Glu | Trp | Leu | Lys | Asn | Gly | Gly | Pro | Ser | His | Gly | His | | Pro | Pro | Pro | | | Lys | | |
| Arg | Val | Arg | Leu | Phe | Ile | Glu | Trp | Leu | Lys | Asn | Gly | Gly | Pro | Ser | Ser | Gly | His | | Pro | Pro | Pro | | | Lys | | |
| Arg | Val | Arg | Leu | Phe | Ile | Glu | Trp | Leu | Lys | Asn | Gly | Gly | Pro | Ser | Ser | Gly | His | | Pro | Pro | Pro | | | Lys | | |
| Arg | Val | Arg | Leu | Phe | Ile | Glu | Trp | Leu | Lys | Asn | Gly | Gly | Pro | Ser | Ser | Gly | His | | Pro | Pro | Pro | Gly | | Lys | Asn | |
| Ala | Val | Arg | Leu | Phe | Ile | Glu | Trp | Leu | Lys | Asn | Gly | Gly | Pro | Ser | Ser | Gly | His | | Pro | Pro | Pro | Gly | | Lys | | |
| Ala | Val | Arg | Leu | Phe | Ile | Glu | Trp | Leu | Lys | Asn | Gly | Gly | Pro | Ser | Ser | Gly | His | | Pro | Pro | Pro | Gly | | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 16 | 25 | 1 | 15 | 5 | 1 | 1 | 22 |
| 16 | 26 | 1 | 15 | | | | |
| 16 | 27 | | | | | | |
| 16 | 28 | | | | | | |
| 16 | 29 | | | | | | |
| 16 | 30 | 1 | 4 | 2 | 0.6 | | |
| 18 | 31 | 1 | 7 | | | | |
| 18 | 32 | 1 | 10 | | | | |
| 16 | 33 | | | 2 | 2.6 | | |
| 18 | 34 | 6 | 19 | 7 | 2.7 | 1 | 44 |
| 18 | 35 | 5 | 17 | 6 | 2.4 | 1 | 44 |
| 16 | 36 | 5 | 18 | 6 | 0.8 | | |
| 16 | 37 | 1 | 13 | 2 | 1.3 | | |
| 18 | 38 | 3 | 16 | 2 | 3 | | |
| 18 | 39 | 3 | 14 | 6 | 2.8 | | |
| 18 | 40 | 2 | 15 | 5 | 1.8 | | |
| 18 | 41 | 2 | 17 | 3 | 1.5 | 1 | 43 |
| 18 | 42 | 5 | 18 | 12 | 1.5 | 1 | 30 |
| 18 | 43 | 1 | 7 | 2 | 1.8 | | |
| 18 | 44 | 4 | 18 | 10 | 4.2 | 1 | 54 |
| 18 | 45 | 1 | 15 | 2 | 2.3 | | |
| 18 | 46 | 1 | 15 | 2 | 1.9 | | |
| 18 | 47 | 1 | 16 | 2 | 1.7 | 1 | 22 |
| 18 | 48 | 3 | 19 | 5 | 2.9 | 1 | 38 |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 49 | 6250 | 49 | dupl 6367 | His | AIB | His | Gly | Thr | Phe | Thr | Ser | Asp | Leu | Ser | Lys | Gln | Leu | Glu | Glu | Lys |
| 50 | 6252 | 50 | | His | AIB | His | Gly | Thr | Phe | Thr | Ser | Asp | Leu | Ser | Lys | Gln | Leu | Glu | Glu | Glu |
| 51 | 6277 | 51 | | His | AIB | His | Gly | Thr | Phe | Thr | Ser | Asp | Leu | Ser | Lys | Gln | Leu | Glu | Glu | Lys |
| 52 | 6299 | 52 | dupl 6407 | His | AIB | His | Gly | Thr | Phe | Thr | Ser | Asp | Leu | Ser | Lys | Gln | Leu | Glu | Glu | Lys |
| 53 | 6321 | 53 | | His | AIB | His | Gly | Thr | Phe | Thr | Ser | Asp | Leu | Ser | Lys | Gln | Leu | Glu | Glu | Lys |
| 54 | 6341 | 54 | dupl 6191 + 6366 + 6458 | His | AIB | His | Gly | Thr | Phe | Thr | Ser | Asp | Leu | Ser | Lys | Gln | Leu | Glu | Glu | Lys |
| 55 | 6342 | 55 | dupl 6237 | His | AIB | His | Gly | Thr | Phe | Thr | Ser | Asp | Leu | Ser | Lys | Gln | Leu | Glu | Glu | Lys |
| 56 | 6366 | 56 | dupl 6191 + 6341 + 6458 | His | AIB | His | Gly | Thr | Phe | Thr | Ser | Asp | Leu | Ser | Lys | Gln | Leu | Glu | Glu | Lys |
| 57 | 6367 | 57 | dupl 6250 | His | AIB | His | Gly | Thr | Phe | Thr | Ser | Asp | Leu | Ser | Lys | Gln | Leu | Glu | Glu | Lys |
| 58 | 6400 | 58 | | His | AIB | His | Gly | Thr | Phe | Thr | Ser | Asp | Leu | Ser | Lys | Gln | Leu | Glu | Glu | Lys |
| 59 | 6401 | 59 | | His | AIB | His | Gly | Thr | Phe | Thr | Ser | Asp | Leu | Ser | Lys | Gln | Leu | Glu | Glu | Lys |
| 60 | 6406 | 60 | dupl 6205 + 6470 | His | AIB | His | Gly | Thr | Phe | Thr | Ser | Asp | Leu | Ser | Lys | Gln | Leu | Glu | Glu | Lys |
| 61 | 6407 | 61 | dupl 6299 | His | AIB | His | Gly | Thr | Phe | Thr | Ser | Asp | Leu | Ser | Lys | Gln | Leu | Glu | Glu | Lys |
| 62 | 6458 | 62 | dupl 6191 + 6341 + 6366 | His | AIB | His | Gly | Thr | Phe | Thr | Ser | Asp | Leu | Ser | Lys | Gln | Leu | Glu | Glu | Lys |
| 63 | 6470 | 63 | dupl 6205 + 6406 | His | AIB | His | Gly | Thr | Phe | Thr | Ser | Asp | Leu | Ser | Lys | Gln | Leu | Glu | Glu | Lys |
| 64 | 6495 | 64 | | His | AIB | His | Gly | Thr | Phe | Thr | Ser | Asp | Tyr | Ser | Lys | Gln | Leu | Glu | Glu | Lys |
| 65 | 6496 | 65 | | His | AIB | His | Gly | Thr | Phe | Thr | Ser | Asp | Leu | Ser | Lys | Gln | Leu | Glu | Glu | Lys |
| 66 | 6505 | 66 | | His | AIB | His | Gly | Thr | Phe | Thr | Ser | Asp | Leu | Ser | Lys | Gln | Leu | Glu | Glu | Lys |
| 67 | 6506 | 67 | | His | AIB | His | Gly | Thr | Phe | Thr | Ser | Asp | Leu | Ser | Lys | Gln | Leu | Glu | Glu | Lys |
| 68 | 6509 | 68 | | His | AIB | His | Gly | Thr | Phe | Thr | Ser | Asp | Leu | Ser | Lys | Gln | Leu | Glu | Glu | Lys |
| 69 | 6510 | 69 | | His | AIB | His | Gly | Thr | Phe | Thr | Ser | Asp | Leu | Ser | Lys | Gln | Leu | Glu | Glu | Lys |
| 70 | 6538 | 70 | | His | AIB | His | Gly | Thr | Phe | Thr | Ser | Asp | Leu | Ser | Lys | Gln | Leu | Glu | Glu | Lys |
| 71 | 6539 | 71 | | His | AIB | His | Gly | Thr | Phe | Thr | Ser | Asp | Leu | Ser | Lys | Gln | Leu | Glu | Glu | Lys |
| 72 | 6540 | 72 | | His | AIB | His | Gly | Thr | Phe | Thr | Ser | Asp | Leu | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Asn | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Gly | | | Lys | | |
| Arg | Val | Arg | Leu | Phe | Ile | Glu | Trp | Leu | Lys | Asn | Gly | Gly | Pro | Ser | Ser | Gly | His | | Pro | Pro | Gly | | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Ala | Val | Arg | Leu | Phe | Ile | Glu | Trp | Leu | Lys | Asn | Gly | Gly | Pro | Ser | Ser | Gly | Ala | | Pro | Pro | Gly | | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | His |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | | | Lys | Asn | His |
| Arg | Val | Arg | Leu | Phe | Ile | Glu | Trp | Leu | Lys | Gln | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | Pro | | Pro | Pro | Gly | | | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | Asn | His |
| Arg | Val | Arg | Leu | Phe | Ile | Glu | Trp | Leu | Lys | Asn | Ala | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Ala | | Pro | Pro | Pro | Gly | | Lys | Asn | His |
| Arg | Val | Arg | Leu | Phe | Ile | Glu | Trp | Leu | Lys | Asn | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Asn | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Asn | Gly | Gly | Pro | Ser | Ser | Gly | Ala | | Pro | Pro | Pro | | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 49 | 3 | 18 | 9 | 3.3 | 3 | 48 |
| 18 | 50 | 1 | 16 | 4 | 3 | 1 | 55 |
| 18 | 51 | 1 | 12 | 2 | 5.6 | | |
| 16 | 52 | 2 | 18 | 6 | 0.7 | | |
| 18 | 53 | 1 | 7 | 2 | 5.6 | | |
| 18 | 54 | 4 | 19 | 6 | 2.7 | 2 | 36 |
| 18 | 55 | 2 | 18 | 5 | 3.1 | | |
| 18 | 56 | | | 2 | 4.8 | | |
| 18 | 57 | 2 | 15 | 2 | 3.8 | | |
| 16 | 58 | 3 | 14 | 2 | 1.2 | 1 | 76 |
| 18 | 59 | 1 | 5 | 2 | 3.5 | | |
| 16 | 60 | | | 2 | 1.1 | | |
| 16 | 61 | | | 3 | 0.9 | | |
| 18 | 62 | | | 3 | 3.1 | | |
| 16 | 63 | | | 3 | 0.8 | | |
| 16 | 64 | 1 | 18 | 4 | 0.51 | 1 | 28 |
| 16 | 65 | 1 | 18 | 4 | 1.4 | 1 | 10 |
| 18 | 66 | 1 | 12 | 4 | 2.7 | 1 | 32 |
| 18 | 67 | 1 | 16 | 4 | 4.3 | 1 | 44 |
| 18 | 68 | 1 | 19 | 3 | 2.8 | 1 | 35 |
| 18 | 69 | 1 | 17 | 4 | 3 | 1 | 58 |
| 16 | 70 | 3 | 14 | 5 | 1.2 | 1 | 37 |
| 18 | 71 | 1 | 7 | 2 | 3.8 | | |
| 16 | 72 | 1 | 10 | 2 | 0.8 | 1 | 67 |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 73 | 6541 | 73 | | His | AIB | His | Gly | Thr | Phe | Thr | Ser | Asp | Leu | Ser | Lys | Gln | Leu | Glu | Glu | Lys |
| 74 | 6545 | 74 | | His | AIB | His | Gly | Thr | Phe | Thr | Ser | Asp | Leu | Ser | Lys | Gln | Leu | Glu | Glu | Lys |
| 75 | 6548 | 75 | | His | AIB | His | Gly | Thr | Phe | Thr | Ser | Asp | Leu | Ser | Lys | Gln | Leu | Glu | Glu | Lys |
| 76 | 6549 | 76 | | His | AIB | His | Gly | Thr | Phe | Thr | Ser | Asp | Tyr | Ser | Lys | Gln | Leu | Glu | Glu | Lys |
| 77 | 6552 | 77 | | His | AIB | His | Gly | Thr | Phe | Thr | Ser | Asp | Tyr | Ser | Lys | Gln | Leu | Glu | Glu | Lys |
| 78 | 6553 | 78 | | His | AIB | His | Gly | Thr | Phe | Thr | Ser | Asp | Tyr | Ser | Lys | Gln | Leu | Glu | Glu | Lys |
| 79 | 6554 | 79 | | His | AIB | His | Gly | Thr | Phe | Thr | Ser | Asp | Leu | Ser | Lys | Gln | Leu | Glu | Glu | Lys |
| 80 | 6555 | 80 | | His | AIB | His | Gly | Thr | Phe | Thr | Ser | Asp | Leu | Ser | Lys | Gln | Leu | Glu | Glu | Lys |
| 81 | 6556 | 81 | | His | AIB | His | Gly | Thr | Phe | Thr | Ser | Asp | Leu | Ser | Lys | Gln | Leu | Glu | Glu | Lys |
| 82 | 6557 | 82 | | His | AIB | His | Gly | Thr | Phe | Thr | Ser | Asp | Leu | Ser | Lys | Gln | Leu | Glu | Glu | Lys |
| 83 | 6558 | 83 | | His | AIB | His | Gly | Thr | Phe | Thr | Ser | Asp | Leu | Ser | Lys | Gln | Leu | Glu | Glu | Glu |
| 84 | 6559 | 84 | | His | AIB | His | Gly | Thr | Phe | Thr | Ser | Asp | Leu | Ser | Lys | Gln | Leu | Glu | Glu | Glu |
| 85 | 6560 | 85 | | His | AIB | His | Gly | Thr | Phe | Thr | Ser | Asp | Leu | Ser | Lys | Gln | Leu | Glu | Glu | Lys |
| 86 | 6561 | 86 | | His | AIB | His | Gly | Thr | Phe | Thr | Ser | Asp | Leu | Ser | Lys | Gln | Leu | Glu | Glu | Glu |
| 87 | 6568 | 87 | | His | AIB | His | Gly | Thr | Phe | Thr | Ser | Asp | Leu | Ser | Lys | Gln | Leu | Glu | Glu | Lys |
| 88 | 6569 | 88 | | His | AIB | His | Gly | Thr | Phe | Thr | Ser | Asp | Leu | Ser | Lys | Gln | Leu | Glu | Glu | Lys |
| 89 | 6570 | 89 | | His | AIB | His | Gly | Thr | Phe | Thr | Ser | Asp | Leu | Ser | Lys | Gln | Leu | Glu | Glu | Lys |
| 90 | 6571 | 90 | | His | AIB | His | Gly | Thr | Phe | Thr | Ser | Asp | Leu | Ser | Lys | Gln | Leu | Glu | Glu | Lys |
| 91 | 6572 | 91 | | His | AIB | His | Gly | Thr | Phe | Thr | Ser | Asp | Tyr | Ser | Lys | Gln | Leu | Glu | Glu | Lys |
| 92 | 6573 | 92 | | His | AIB | His | Gly | Thr | Phe | Thr | Ser | Asp | Leu | Ser | Lys | Gln | Leu | Glu | Glu | Lys |
| 93 | 6574 | 93 | | His | AIB | His | Gly | Thr | Phe | Thr | Ser | Asp | Tyr | Ser | Lys | Gln | Leu | Glu | Glu | Lys |
| 94 | 6575 | 94 | | His | AIB | His | Gly | Thr | Phe | Thr | Ser | Asp | Leu | Ser | Lys | Gln | Leu | Glu | Glu | Lys |
| 95 | 6576 | 95 | | His | AIB | His | Gly | Thr | Phe | Thr | Ser | Asp | Leu | Ser | Lys | Gln | Leu | Glu | Glu | Lys |
| 96 | 6577 | 96 | | His | AIB | His | Gly | Thr | Phe | Thr | Ser | Asp | Leu | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Asn | Gly | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Ala | | Pro | Pro | Pro | | | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Ala | | Pro | Pro | Pro | | | Lys | | |
| Arg | Val | Arg | Leu | Phe | Ile | Glu | Trp | Leu | Lys | Asn | Ala | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Lys | | Pro | Pro | Pro | Gly | | Lys | | |
| Ala | Val | Arg | Leu | Phe | Ile | Glu | Trp | Leu | Lys | Gln | Gly | Gly | Pro | Ser | Ser | Gly | Lys | | Pro | Pro | Pro | Gly | | Lys | | |
| Ala | Val | Arg | Leu | Phe | Ile | Glu | Trp | Leu | Lys | Gln | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | Lys | | Pro | Pro | Pro | Gly | | Lys | | |
| Ala | Val | Arg | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | His | | Pro | Pro | Pro | | | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | | | Lys | | |
| Arg | Val | Arg | Leu | Phe | Ile | Glu | Trp | Leu | Lys | His | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | His | | Pro | Pro | Pro | Gly | | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 73 | 1 | 8 | 3 | 3.2 | 1 | 54 |
| 18 | 74 | 1 | 6 | 2 | 1.8 | | |
| 18 | 75 | 1 | 10 | 3 | 3.6 | 1 | 60 |
| 18 | 76 | 1 | 10 | 3 | 1.6 | 1 | 70 |
| 18 | 77 | 1 | 6 | 3 | 2.3 | | |
| 18 | 78 | 1 | 6 | 3 | 3.3 | | |
| 16 | 79 | 1 | 11 | 3 | 0.9 | | |
| 18 | 80 | 1 | 5 | 3 | 2.5 | | |
| 16 | 81 | 2 | 16 | 4 | 1 | 1 | 37 |
| 18 | 82 | 1 | 9 | 3 | 2.5 | | |
| 16 | 83 | 2 | 15 | 3 | 0.6 | 1 | 68 |
| 18 | 84 | 1 | 6 | 3 | 1.7 | | |
| 18 | 85 | 1 | 5 | 3 | 2.3 | | |
| 18 | 86 | 1 | 7 | 2 | 2.6 | | |
| 18 | 87 | 1 | 11 | 2 | 3.1 | 1 | 64 |
| 18 | 88 | 1 | 9 | 2 | 3.7 | | |
| 18 | 89 | 1 | 7 | 2 | 4.5 | | |
| 18 | 90 | 1 | 3 | 2 | 5.2 | | |
| 16 | 91 | 1 | 14 | 2 | 0.6 | | |
| 16 | 92 | 1 | 13 | 3 | 1.2 | 1 | 35 |
| 18 | 93 | 1 | 10 | 3 | 3 | 1 | 70 |
| 18 | 94 | 1 | 10 | 2 | 4.6 | | |
| 18 | 95 | 1 | 12 | 2 | 4 | | |
| 18 | 96 | 1 | 3 | 2 | 3.5 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 97 | 6578 | 97 | dupl 6239 | His | AIB | His | Gly | Thr | Phe | Thr | Ser | Asp | Leu | Ser | Lys | Gln | Leu | Glu | Glu | Lys |
| 98 | 6579 | 98 | | His | AIB | His | Gly | Thr | Phe | Thr | Ser | Asp | Leu | Ser | Lys | Gln | Leu | Glu | Glu | Lys |
| 99 | 6580 | 99 | | His | AIB | His | Gly | Thr | Phe | Thr | Ser | Asp | Leu | Ser | Lys | Gln | Leu | Glu | Glu | Lys |
| 100 | 6581 | 100 | | His | AIB | His | Gly | Thr | Phe | Thr | Ser | Asp | Leu | Ser | Lys | Gln | Leu | Glu | Glu | Lys |
| 101 | 6582 | 101 | | His | AIB | His | Gly | Thr | Phe | Thr | Ser | Asp | Leu | Ser | Lys | Gln | Leu | Glu | Glu | Lys |
| 102 | 6583 | 102 | | His | AIB | His | Gly | Thr | Phe | Thr | Ser | Asp | Leu | Ser | Lys | Gln | Leu | Glu | Glu | Lys |
| 103 | 6584 | 103 | dupl 6935 | His | AIB | His | Gly | Thr | Phe | Thr | Ser | Asp | Leu | Ser | Lys | Gln | Leu | Glu | Glu | Lys |
| 104 | 6585 | 104 | | His | AIB | His | Gly | Thr | Phe | Thr | Ser | Asp | Tyr | Ser | Lys | Gln | Leu | Glu | Glu | Lys |
| 105 | 6587 | 105 | | His | AIB | His | Gly | Thr | Phe | Thr | Ser | Asp | Leu | Ser | Lys | Gln | Leu | Glu | Glu | Lys |
| 106 | 6595 | 106 | | His | AIB | His | Gly | Thr | Phe | Thr | Ser | Asp | Leu | Ser | Lys | Gln | Leu | Glu | Glu | Lys |
| 107 | 6597 | 107 | | His | AIB | His | Gly | Thr | Phe | Thr | Ser | Asp | Leu | Ser | Lys | Gln | Leu | Glu | Glu | Glu |
| 108 | 6600 | 108 | | His | AIB | His | Gly | Thr | Phe | Thr | Ser | Asp | Tyr | Ser | Lys | Gln | Leu | Glu | Glu | Lys |
| 109 | 6601 | 109 | | His | AIB | His | Gly | Thr | Phe | Thr | Ser | Asp | Leu | Ser | Lys | Gln | Leu | Glu | Glu | Lys |
| 110 | 6602 | 110 | | His | AIB | His | Gly | Thr | Phe | Thr | Ser | Asp | Leu | Ser | Lys | Gln | Leu | Glu | Glu | Lys |
| 111 | 6603 | 111 | | His | AIB | His | Gly | Thr | Phe | Thr | Ser | Asp | Tyr | Ser | Lys | Gln | Leu | Glu | Glu | Lys |
| 112 | 6604 | 112 | | His | AIB | His | Gly | Thr | Phe | Thr | Ser | Asp | Tyr | Ser | Lys | Gln | Leu | Glu | Glu | Lys |
| 113 | 6605 | 113 | | His | AIB | His | Gly | Thr | Phe | Thr | Ser | Asp | Tyr | Ser | Lys | Gln | Leu | Glu | Glu | Lys |
| 114 | 6606 | 114 | dupl 6608 | His | AIB | His | Gly | Thr | Phe | Thr | Ser | Asp | Tyr | Ser | Lys | Gln | Leu | Glu | Glu | Lys |
| 115 | 6607 | 115 | | His | AIB | His | Gly | Thr | Phe | Thr | Ser | Asp | Tyr | Ser | Lys | Gln | Leu | Glu | Glu | Lys |
| 116 | 6608 | 116 | dupl 6606 | His | AIB | His | Gly | Thr | Phe | Thr | Ser | Asp | Tyr | Ser | Lys | Gln | Leu | Glu | Glu | Lys |
| 117 | 6609 | 117 | dupl 6867 | His | AIB | His | Gly | Thr | Phe | Thr | Ser | Asp | Tyr | Ser | Lys | Gln | Leu | Glu | Glu | Lys |
| 118 | 6610 | 118 | | His | AIB | His | Gly | Thr | Phe | Thr | Ser | Asp | Tyr | Ser | Lys | Gln | Leu | Glu | Glu | Lys |
| 119 | 6611 | 119 | | His | AIB | His | Gly | Thr | Phe | Thr | Ser | Asp | Tyr | Ser | Lys | Gln | Leu | Glu | Glu | Lys |
| 120 | 6612 | 120 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Asn | Gly | Gly | Pro | Ser | Ser | Gly | His | | Pro | Pro | Pro | | | Lys | | |
| Arg | Val | Arg | Glu | Phe | Ile | Glu | Trp | Leu | Lys | Gln | Gly | Gly | Pro | Ser | Ser | Gly | Ala | | Pro | Pro | Pro | Gly | | Lys | | |
| Arg | Val | His | Glu | Phe | Ile | Glu | Trp | Leu | Lys | Gln | Gly | Gly | Pro | Ser | Ser | Gly | Ala | | Pro | Pro | Pro | Gly | | Lys | | |
| Arg | Val | Arg | Glu | Phe | Ile | Glu | Trp | Leu | Lys | Gln | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Gln | Gly | Gly | Pro | Ser | His | Gly | His | | Pro | Pro | Pro | Gly | | Lys | | |
| Arg | Val | His | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Gln | Glu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | Glu | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | Gly | | Lys | | |
| Ala | Val | Arg | Leu | Phe | Ile | Glu | Trp | Leu | Lys | Asn | Ala | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | | |
| Ala | Val | Arg | Leu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | | |
| Ala | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | | |
| Ala | Val | Arg | Leu | Phe | Ile | Glu | Trp | Leu | Lys | Ala | Gly | Gly | Pro | Ser | Ser | Gly | His | | Pro | Pro | Pro | | Lys | Lys | | |
| Ala | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | Asn | His |
| Ala | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | Asn | His |
| Ala | Val | Arg | Leu | Phe | Ile | Glu | Trp | Leu | Lys | Ala | Gly | Gly | Pro | Ser | Ser | Gly | His | | Pro | Pro | Pro | | Lys | Lys | Asn | His |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 97 | | | 2 | 5.1 | | |
| 18 | 98 | 2 | 12 | 2 | 3.3 | 1 | 65 |
| 18 | 99 | 1 | 7 | 2 | 2.5 | | |
| 18 | 100 | 1 | 7 | 2 | 2.6 | | |
| 18 | 101 | 2 | 9 | 3 | 2.6 | 1 | 78 |
| 18 | 102 | 2 | 6 | 2 | 5.3 | 1 | 90 |
| 18 | 103 | 3 | 9 | 3 | 2.8 | 3 | 67 |
| 18 | 104 | 2 | 12 | 3 | 3.6 | 2 | 85 |
| 18 | 105 | 1 | 2 | 2 | 2.8 | | |
| 18 | 106 | 1 | 12 | 4 | 4.7 | 1 | 37 |
| 18 | 107 | 2 | 9 | 4 | 3 | 2 | 68 |
| 18 | 108 | 1 | 8 | 2 | 3.8 | | |
| 18 | 109 | 1 | 11 | 3 | 5.3 | | |
| 16 | 110 | 2 | 16 | 5 | 1 | 1 | 46 |
| 18 | 111 | 2 | 15 | 4 | 1.6 | 2 | 67 |
| 18 | 112 | 3 | 16 | 6 | 2.2 | 2 | 56 |
| 18 | 113 | 2 | 10 | 4 | 2.9 | 2 | 47 |
| 18 | 114 | 1 | 12 | 2 | 2.6 | | |
| 18 | 115 | 2 | 11 | 2 | 3.9 | 2 | 72 |
| 18 | 116 | 1 | 14 | 2 | 2.8 | 1 | 70 |
| 18 | 117 | 2 | 13 | 4 | 3.9 | 2 | 84 |
| 16 | 118 | 1 | 14 | 2 | 0.8 | | |
| 16 | 119 | 1 | 17 | 2 | 0.9 | 1 | 62 |
| 16 | 120 | 1 | 16 | 3 | 1.2 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 121 | 6613 | 121 | | His | AIB | His | Gly | Thr | Phe | Thr | Ser | Asp | Tyr | Ser | Lys | Gln | Leu | Glu | Glu | Lys |
| 122 | 6614 | 122 | | His | AIB | His | Gly | Thr | Phe | Thr | Ser | Asp | Leu | Ser | Lys | Gln | Leu | Glu | Glu | Glu |
| 123 | 6615 | 123 | | His | AIB | His | Gly | Thr | Phe | Thr | Ser | Asp | Tyr | Ser | Lys | Gln | Leu | Glu | Glu | Glu |
| 124 | 6616 | 124 | | His | AIB | His | Gly | Thr | Phe | Thr | Ser | Asp | Tyr | Ser | Lys | Gln | Leu | Glu | Glu | Glu |
| 125 | 6617 | 125 | | His | AIB | His | Gly | Thr | Phe | Thr | Ser | Asp | Leu | Ser | Lys | Gln | Leu | Glu | Glu | Glu |
| 126 | 6618 | 126 | | His | AIB | His | Gly | Thr | Phe | Thr | Ser | Asp | Tyr | Ser | Lys | Gln | Leu | Glu | Glu | Glu |
| 127 | 6619 | 127 | | His | AIB | His | Gly | Thr | Phe | Thr | Ser | Asp | Tyr | Ser | Lys | Gln | Leu | Glu | Glu | Glu |
| 128 | 6620 | 128 | | His | AIB | His | Gly | Thr | Phe | Thr | Ser | Asp | Tyr | Ser | Lys | Gln | Leu | Glu | Glu | Lys |
| 129 | 6621 | 129 | | His | AIB | His | Gly | Thr | Phe | Thr | Ser | Asp | Tyr | Ser | Lys | Gln | Leu | Glu | Glu | Lys |
| 130 | 6622 | 130 | | His | AIB | His | Gly | Thr | Phe | Thr | Ser | Asp | Tyr | Ser | Lys | Gln | Leu | Glu | Glu | Lys |
| 131 | 6623 | 131 | | His | AIB | His | Gly | Thr | Phe | Thr | Ser | Asp | Tyr | Ser | Lys | Gln | Leu | Glu | Glu | Lys |
| 132 | 6624 | 132 | | His | AIB | His | Gly | Thr | Phe | Thr | Ser | Asp | Tyr | Ser | Lys | Gln | Leu | Glu | Glu | Lys |
| 133 | 6625 | 133 | | His | AIB | His | Gly | Thr | Phe | Thr | Ser | Asp | Tyr | Ser | Lys | Gln | Leu | Glu | Glu | Lys |
| 134 | 6626 | 134 | | His | AIB | His | Gly | Thr | Phe | Thr | Ser | Asp | Tyr | Ser | Lys | Gln | Leu | Glu | Glu | Lys |
| 135 | 6627 | 135 | | His | AIB | His | Gly | Thr | Phe | Thr | Ser | Asp | Tyr | Ser | Lys | Gln | Leu | Glu | Glu | Lys |
| 136 | 6628 | 136 | | His | AIB | His | Gly | Thr | Phe | Thr | Ser | Asp | Tyr | Ser | Lys | Gln | Leu | Glu | Glu | Lys |
| 137 | 6629 | 137 | dupl 6873 | His | AIB | His | Gly | Thr | Phe | Thr | Ser | Asp | Leu | Ser | Lys | Gln | Leu | Glu | Glu | Glu |
| 138 | 6630 | 138 | | His | AIB | His | Gly | Thr | Phe | Thr | Ser | Asp | Leu | Ser | Lys | Gln | Leu | Glu | Glu | Glu |
| 139 | 6633 | 139 | dupl 6870 | His | AIB | His | Gly | Thr | Phe | Thr | Ser | Asp | Leu | Ser | Lys | Gln | Leu | Glu | Glu | Lys |
| 140 | 6634 | 140 | | His | AIB | His | Gly | Thr | Phe | Thr | Ser | Asp | Leu | Ser | Lys | Gln | Leu | Glu | Glu | Lys |
| 141 | 6635 | 141 | | His | AIB | His | Gly | Thr | Phe | Thr | Ser | Asp | Tyr | Ser | Lys | Gln | Leu | Glu | Glu | Lys |
| 142 | 6636 | 142 | | His | AIB | His | Gly | Thr | Phe | Thr | Ser | Asp | Tyr | Ser | Lys | Gln | Leu | Glu | Glu | Lys |
| 143 | 6637 | 143 | | His | AIB | His | Gly | Thr | Phe | Thr | Ser | Asp | Tyr | Ser | Lys | Gln | Leu | Glu | Glu | Lys |
| 144 | 6638 | 144 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | Arg | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Leu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | His | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | His | | Pro | Pro | Pro | | Lys | Lys | | |
| Arg | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Ala | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Ala | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Ala | Val | His | Glu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | His | Glu | Phe | Ile | Glu | Trp | Leu | Lys | Ala | Gly | Gly | Pro | Ser | Ser | Gly | Lys | | Pro | Pro | Pro | | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 16 | 121 | 1 | 13 | 2 | 0.9 | | |
| 18 | 122 | 1 | 11 | 3 | 3.7 | 1 | 60 |
| 18 | 123 | 1 | 7 | 2 | 3.1 | | |
| 18 | 124 | 1 | 10 | 2 | 3.3 | 1 | 71 |
| 16 | 125 | 1 | 16 | 2 | 0.9 | | |
| 16 | 126 | 2 | 15 | 4 | 1 | 1 | 56 |
| 16 | 127 | 2 | 13 | 3 | 0.9 | 1 | 42 |
| 16 | 128 | 2 | 15 | 3 | 0.7 | | |
| 16 | 129 | 2 | 15 | 4 | 0.9 | 1 | 35 |
| 16 | 130 | 1 | 13 | 2 | 0.6 | | |
| 16 | 131 | 2 | 15 | 3 | 0.8 | | |
| 16 | 132 | 2 | 16 | 3 | 0.7 | | |
| 16 | 133 | 2 | 12 | 4 | 0.9 | 1 | 24 |
| 18 | 134 | 3 | 10 | 4 | 3.1 | 1 | 65 |
| 18 | 135 | 3 | 5 | 2 | 2.7 | 1 | 80 |
| 18 | 136 | 1 | 3 | 2 | 3 | | |
| 18 | 137 | 2 | 7 | 5 | 3.3 | 2 | 97 |
| 18 | 138 | 1 | 5 | 2 | 3.7 | | |
| 18 | 139 | 2 | 8 | 5 | 3.7 | 3 | 98 |
| 16 | 140 | 1 | 11 | 2 | 1 | | |
| 18 | 141 | 1 | 6 | 2 | 3 | | |
| 16 | 142 | 2 | 16 | 2 | 0.6 | 1 | 70 |
| 18 | 143 | 2 | 10 | 4 | 1.8 | 1 | 85 |
| 16 | 144 | 1 | 12 | 2 | 0.43 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 145 | 6639 | 145 | | His | AIB | His | Gly | Thr | Phe | Thr | Ser | Asp | Tyr | Ser | Lys | Gln | Leu | Glu | Glu | Lys |
| 146 | 6640 | 146 | | His | AIB | His | Gly | Thr | Phe | Thr | Ser | Asp | Tyr | Ser | Lys | Gln | Leu | Glu | Glu | Lys |
| 147 | 6641 | 147 | | His | AIB | His | Gly | Thr | Phe | Thr | Ser | Asp | Tyr | Ser | Lys | Gln | Leu | Glu | Glu | Lys |
| 148 | 6642 | 148 | | His | AIB | His | Gly | Thr | Phe | Thr | Ser | Asp | Tyr | Ser | Lys | Gln | Leu | Glu | Glu | Lys |
| 149 | 6643 | 149 | | His | AIB | His | Gly | Thr | Phe | Thr | Ser | Asp | Tyr | Ser | Lys | Gln | Leu | Glu | Glu | Glu |
| 150 | 6644 | 150 | | His | AIB | His | Gly | Thr | Phe | Thr | Ser | Asp | Tyr | Ser | Lys | Gln | Leu | Glu | Glu | Glu |
| 151 | 6645 | 151 | | His | AIB | His | Gly | Thr | Phe | Thr | Ser | Asp | Tyr | Ser | Lys | Gln | Leu | Glu | Glu | Glu |
| 152 | 6646 | 152 | | His | AIB | His | Gly | Thr | Phe | Thr | Ser | Asp | Tyr | Ser | Lys | Gln | Leu | Glu | Glu | Glu |
| 153 | 6647 | 153 | | His | AIB | His | Gly | Thr | Phe | Thr | Ser | Asp | Tyr | Ser | Lys | Gln | Leu | Glu | Glu | Glu |
| 154 | 6648 | 154 | | His | AIB | His | Gly | Thr | Phe | Thr | Ser | Asp | Tyr | Ser | Lys | Gln | Leu | Glu | Glu | Glu |
| 155 | 6649 | 155 | | His | AIB | His | Gly | Thr | Phe | Thr | Ser | Asp | Leu | Ser | Lys | Gln | Leu | Glu | Glu | Glu |
| 156 | 6653 | 156 | | His | AIB | His | Gly | Thr | Phe | Thr | Ser | Asp | Leu | Ser | Lys | Gln | Leu | Glu | Glu | Glu |
| 157 | 6655 | 157 | | His | AIB | His | Gly | Thr | Phe | Thr | Ser | Asp | Leu | Ser | Lys | Gln | Leu | Glu | Glu | Glu |
| 158 | 6656 | 158 | | His | AIB | His | Gly | Thr | Phe | Thr | Ser | Asp | Leu | Ser | Lys | Gln | Leu | Glu | Glu | Glu |
| 159 | 6657 | 159 | | His | AIB | His | Gly | Thr | Phe | Thr | Ser | Asp | Tyr | Ser | Lys | Gln | Leu | Glu | Glu | Glu |
| 160 | 6658 | 160 | | His | AIB | His | Gly | Thr | Phe | Thr | Ser | Asp | Leu | Ser | Lys | Gln | Leu | Glu | Glu | Glu |
| 161 | 6659 | 161 | | His | AIB | His | Gly | Thr | Phe | Thr | Ser | Asp | Leu | Ser | Lys | Gln | Leu | Glu | Glu | Glu |
| 162 | 6660 | 162 | | His | AIB | His | Gly | Thr | Phe | Thr | Ser | Asp | Tyr | Ser | Lys | Gln | Leu | Glu | Glu | Glu |
| 163 | 6661 | 163 | | His | AIB | His | Gly | Thr | Phe | Thr | Ser | Asp | Tyr | Ser | Lys | Gln | Leu | Glu | Glu | Glu |
| 164 | 6662 | 164 | | His | AIB | His | Gly | Thr | Phe | Thr | Ser | Asp | Tyr | Ser | Lys | Gln | Leu | Glu | Glu | Glu |
| 165 | 6663 | 165 | | His | AIB | His | Gly | Thr | Phe | Thr | Ser | Asp | Leu | Ser | Lys | Gln | Leu | Glu | Glu | Glu |
| 166 | 6665 | 166 | | His | AIB | His | Gly | Thr | Phe | Thr | Ser | Asp | Tyr | Ser | Lys | Gln | Leu | Glu | Glu | Glu |
| 167 | 6666 | 167 | | His | AIB | His | Gly | Thr | Phe | Thr | Ser | Asp | Tyr | Ser | Lys | Gln | Leu | Glu | Glu | Glu |
| 168 | 6667 | 168 | | His | AIB | His | Gly | Thr | Phe | Thr | Ser | Asp | Tyr | Ser | Lys | Gln | Leu | Glu | Glu | Glu |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Asn | Ala | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Gly | | | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Gly | | | Lys | | |
| Arg | Val | Arg | Leu | Phe | Ile | Glu | Trp | Leu | Lys | Asn | Ala | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Gly | | | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Gly | | | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | Arg | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | Arg | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Asn | Ala | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | His | | Pro | Pro | Pro | Gly | | Lys | Asn | His |
| Arg | Val | Arg | Leu | Phe | Ile | Glu | Trp | Leu | Lys | Ala | Gly | Gly | Pro | Ser | Ser | Gly | His | | Pro | Pro | Pro | Gly | | Lys | Asn | His |
| Arg | Val | Arg | Leu | Phe | Ile | Glu | Trp | Leu | Lys | Ala | Gly | Gly | Pro | Ser | Ser | Gly | His | | Pro | Pro | Pro | | Lys | Lys | Asn | His |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 145 | 1 | 8 | 2 | 4.6 | | |
| 18 | 146 | 1 | 13 | 2 | 3 | | |
| 18 | 147 | 1 | 4 | 2 | 2.8 | | |
| 16 | 148 | 1 | 9 | 3 | 1.5 | | |
| 18 | 149 | 1 | 1 | 2 | 2.3 | | |
| 18 | 150 | 1 | 12 | 2 | 2.2 | | |
| 18 | 151 | 1 | 12 | 2 | 2.5 | 1 | 65 |
| 16 | 152 | 1 | 8 | 2 | 0.8 | | |
| 18 | 153 | 2 | 10 | 2 | 2.2 | 1 | 61 |
| 16 | 154 | 1 | 9 | 2 | 0.7 | | |
| 16 | 155 | 1 | 12 | 2 | 1.1 | | |
| 18 | 156 | 1 | 3 | 2 | 3.5 | | |
| 18 | 157 | 1 | 8 | 2 | 3.7 | | |
| 16 | 158 | 1 | 12 | 3 | 1 | | |
| 18 | 159 | 1 | 2 | 2 | 1.7 | | |
| 18 | 160 | 1 | 7 | 2 | 2.6 | 1 | 57 |
| 16 | 161 | 1 | 10 | 3 | 0.9 | | |
| 18 | 162 | 2 | 11 | 2 | 2.5 | 1 | 81 |
| 16 | 163 | 1 | 12 | 4 | 0.56 | | |
| 18 | 164 | 2 | 7 | 2 | 2.4 | 1 | 64 |
| 18 | 165 | 1 | 5 | 2 | 2.6 | | |
| 16 | 166 | 1 | 8 | 3 | 0.6 | | |
| 18 | 167 | 1 | 4 | 2 | 2 | | |
| 16 | 168 | 1 | 9 | 3 | 0.6 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 169 | 6668 | 169 | | His | AIB | His | Gly | Thr | Phe | Thr | Ser | Asp | Tyr | Ser | Lys | Gln | Leu | Glu | Glu | Glu |
| 170 | 6669 | 170 | | His | AIB | His | Gly | Thr | Phe | Thr | Ser | Asp | Tyr | Ser | Lys | Gln | Leu | Glu | Glu | Glu |
| 171 | 6670 | 171 | | His | AIB | His | Gly | Thr | Phe | Thr | Ser | Asp | Tyr | Ser | Lys | Gln | Leu | Glu | Glu | Glu |
| 172 | 6671 | 172 | | His | AIB | His | Gly | Thr | Phe | Thr | Ser | Asp | Tyr | Ser | Lys | Gln | Leu | Glu | Glu | Glu |
| 173 | 6672 | 173 | | His | AIB | His | Gly | Thr | Phe | Thr | Ser | Asp | Tyr | Ser | Lys | Gln | Leu | Glu | Glu | Glu |
| 174 | 6673 | 174 | | His | AIB | His | Gly | Thr | Phe | Thr | Ser | Asp | Tyr | Ser | Lys | Gln | Leu | Glu | Glu | Glu |
| 175 | 6677 | 175 | | His | AIB | His | Gly | Thr | Phe | Thr | Ser | Asp | Tyr | Ser | Lys | Gln | Leu | Glu | Glu | Glu |
| 176 | 6680 | 176 | | His | AIB | His | Gly | Thr | Phe | Thr | Ser | Asp | Tyr | Ser | Lys | Gln | Leu | Glu | Glu | Glu |
| 177 | 6681 | 177 | | His | AIB | His | Gly | Thr | Phe | Thr | Ser | Asp | Tyr | Ser | Lys | Gln | Leu | Glu | Glu | Glu |
| 178 | 6682 | 178 | | His | AIB | His | Gly | Thr | Phe | Thr | Ser | Asp | Tyr | Ser | Lys | Gln | Leu | Glu | Glu | Glu |
| 179 | 6683 | 179 | | His | AIB | His | Gly | Thr | Phe | Thr | Ser | Asp | Tyr | Ser | Lys | Gln | Leu | Glu | Glu | Glu |
| 180 | 6684 | 180 | | His | AIB | His | Gly | Thr | Phe | Thr | Ser | Asp | Tyr | Ser | Lys | Gln | Leu | Glu | Glu | Glu |
| 181 | 6685 | 181 | | His | AIB | His | Gly | Thr | Phe | Thr | Ser | Asp | Tyr | Ser | Lys | Gln | Leu | Glu | Glu | Glu |
| 182 | 6686 | 182 | | His | AIB | His | Gly | Thr | Phe | Thr | Ser | Asp | Tyr | Ser | Lys | Gln | Leu | Glu | Glu | Glu |
| 183 | 6688 | 183 | | His | AIB | His | Gly | Thr | Phe | Thr | Ser | Asp | Tyr | Ser | Lys | Gln | Leu | Glu | Glu | Glu |
| 184 | 6690 | 184 | | His | AIB | His | Gly | Thr | Phe | Thr | Ser | Asp | Tyr | Ser | Lys | Gln | Leu | Glu | Glu | Glu |
| 185 | 6691 | 185 | | His | AIB | His | Gly | Thr | Phe | Thr | Ser | Asp | Tyr | Ser | Lys | Gln | Leu | Glu | Glu | Glu |
| 186 | 6692 | 186 | | His | AIB | His | Gly | Thr | Phe | Thr | Ser | Asp | Tyr | Ser | Lys | Gln | Leu | Glu | Glu | Glu |
| 187 | 6693 | 187 | | His | AIB | His | Gly | Thr | Phe | Thr | Ser | Asp | Tyr | Ser | Lys | Gln | Leu | Glu | Glu | Lys |
| 188 | 6694 | 188 | | His | AIB | His | Gly | Thr | Phe | Thr | Ser | Asp | Tyr | Ser | Lys | Gln | Leu | Glu | Glu | Glu |
| 189 | 6695 | 189 | | His | AIB | His | Gly | Thr | Phe | Thr | Ser | Asp | Tyr | Ser | Lys | Gln | Leu | Glu | Glu | Glu |
| 190 | 6696 | 190 | | His | AIB | His | Gly | Thr | Phe | Thr | Ser | Asp | Tyr | Ser | Lys | Gln | Leu | Glu | Glu | Glu |
| 191 | 6697 | 191 | | His | AIB | His | Gly | Thr | Phe | Thr | Ser | Asp | Tyr | Ser | Lys | Gln | Leu | Glu | Glu | Glu |
| 192 | 6698 | 192 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Ala | Gly | Gly | Pro | Ser | Ser | Gly | His | | Pro | Pro | Pro | | Lys | Lys | Asn | His |
| Arg | Val | Arg | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Ala | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | | Lys | Lys | Asn | His |
| Arg | Val | Arg | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Ala | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Asn | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Glu | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Gln | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Ser | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | Gly | Lys | Lys | Asn | His |
| Arg | Val | Arg | Leu | Phe | Ile | Glu | Trp | Leu | Lys | His | Gly | Gly | Pro | Ser | Ser | Gly | His | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | His | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | His | | Pro | Pro | Pro | Gly | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 169 | 1 | 2 | 2 | 1.8 | | |
| 18 | 170 | 1 | 0 | 3 | 2.3 | | |
| 18 | 171 | 1 | 5 | 2 | 2 | | |
| 18 | 172 | 1 | 9 | 2 | 1.7 | | |
| 16 | 173 | 1 | 11 | 2 | 0.7 | | |
| 16 | 174 | 1 | 9 | 2 | 0.8 | | |
| 18 | 175 | 1 | 5 | 3 | 3.5 | | |
| 18 | 176 | 1 | 7 | 3 | 4.1 | | |
| 16 | 177 | 1 | 7 | 2 | 1.7 | | |
| 16 | 178 | 1 | 6 | 2 | 0.9 | | |
| 16 | 179 | 1 | 13 | 2 | 0.55 | | |
| 16 | 180 | 1 | 8 | 2 | 0.49 | | |
| 16 | 181 | 1 | 8 | 2 | 0.52 | | |
| 16 | 182 | 1 | 8 | 2 | 0.33 | | |
| 16 | 183 | 1 | 10 | 2 | 0.51 | | |
| 16 | 184 | 1 | 9 | 2 | 0.61 | | |
| 16 | 185 | 1 | 6 | 2 | 0.6 | | |
| 16 | 186 | 1 | 9 | 2 | 0.6 | | |
| 18 | 187 | 1 | 8 | 2 | 2.3 | | |
| 18 | 188 | 2 | 9 | 2 | 1.9 | 1 | 72 |
| 16 | 189 | 1 | 10 | 2 | 0.6 | | |
| 18 | 190 | 2 | 7 | 4 | 2.2 | 1 | 100 |
| 16 | 191 | 1 | 11 | 2 | 0.6 | | |
| 16 | 192 | 1 | 15 | 2 | 0.5 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 193 | 6699 | 193 | dupl 6868 | His | AIB | His | Gly | Thr | Phe | Thr | Ser | Asp | Tyr | Ser | Lys | Gln | Leu | Glu | Glu | Glu |
| 194 | 6700 | 194 | | His | AIB | His | Gly | Thr | Phe | Thr | Ser | Asp | Tyr | Ser | Lys | Gln | Leu | Glu | Glu | Lys |
| 195 | 6701 | 195 | | His | AIB | His | Gly | Thr | Phe | Thr | Ser | Asp | Tyr | Ser | Lys | Gln | Leu | Glu | Glu | Glu |
| 196 | 6702 | 196 | dupl 6913 | His | AIB | His | Gly | Thr | Phe | Thr | Ser | Asp | Tyr | Ser | Lys | Gln | Leu | Glu | Glu | Glu |
| 197 | 6703 | 197 | | His | AIB | His | Gly | Thr | Phe | Thr | Ser | Asp | Tyr | Ser | Lys | Gln | Leu | Glu | Glu | Glu |
| 198 | 6704 | 198 | | His | AIB | His | Gly | Thr | Phe | Thr | Ser | Asp | Tyr | Ser | Lys | Gln | Leu | Glu | Glu | Glu |
| 199 | 6705 | 199 | | His | AIB | His | Gly | Thr | Phe | Thr | Ser | Asp | Tyr | Ser | Lys | Gln | Leu | Glu | Glu | Glu |
| 200 | 6706 | 200 | | His | AIB | His | Gly | Thr | Phe | Thr | Ser | Asp | Tyr | Ser | Lys | Gln | Leu | Glu | Glu | Lys |
| 201 | 6707 | 201 | | His | AIB | His | Gly | Thr | Phe | Thr | Ser | Asp | Tyr | Ser | Lys | Gln | Leu | Glu | Glu | Lys |
| 202 | 6708 | 202 | | His | AIB | His | Gly | Thr | Phe | Thr | Ser | Asp | Tyr | Ser | Lys | Gln | Leu | Glu | Glu | Lys |
| 203 | 6709 | 203 | | His | AIB | His | Gly | Thr | Phe | Thr | Ser | Asp | Tyr | Ser | Lys | Gln | Leu | Glu | Glu | Glu |
| 204 | 6710 | 204 | | His | AIB | His | Gly | Thr | Phe | Thr | Ser | Asp | Tyr | Ser | Lys | Gln | Leu | Glu | Glu | Glu |
| 205 | 6711 | 205 | | His | AIB | His | Gly | Thr | Phe | Thr | Ser | Asp | Tyr | Ser | Lys | Gln | Leu | Glu | Glu | Glu |
| 206 | 6712 | 206 | | His | AIB | His | Gly | Thr | Phe | Thr | Ser | Asp | Tyr | Ser | Lys | Gln | Leu | Glu | Glu | Glu |
| 207 | 6713 | 207 | | His | AIB | His | Gly | Thr | Phe | Thr | Ser | Asp | Tyr | Ser | Lys | Gln | Leu | Glu | Glu | Glu |
| 208 | 6714 | 208 | | His | AIB | His | Gly | Thr | Phe | Thr | Ser | Asp | Tyr | Ser | Lys | Gln | Leu | Glu | Glu | Glu |
| 209 | 6715 | 209 | | His | AIB | His | Gly | Thr | Phe | Thr | Ser | Asp | Tyr | Ser | Lys | Gln | Leu | Glu | Glu | Glu |
| 210 | 6716 | 210 | | His | AIB | His | Gly | Thr | Phe | Thr | Ser | Asp | Tyr | Ser | Lys | Gln | Leu | Glu | Glu | Glu |
| 211 | 6717 | 211 | | His | AIB | His | Gly | Thr | Phe | Thr | Ser | Asp | Tyr | Ser | Lys | Gln | Leu | Glu | Glu | Glu |
| 212 | 6718 | 212 | | His | AIB | His | Gly | Thr | Phe | Thr | Ser | Asp | Tyr | Ser | Lys | Gln | Leu | Glu | Glu | Glu |
| 213 | 6719 | 213 | | His | AIB | His | Gly | Thr | Phe | Thr | Ser | Asp | Tyr | Ser | Lys | Gln | Leu | Glu | Glu | Glu |
| 214 | 6720 | 214 | | His | AIB | His | Gly | Thr | Phe | Thr | Ser | Asp | Tyr | Ser | Lys | Gln | Leu | Glu | Glu | Glu |
| 215 | 6721 | 215 | | His | AIB | His | Gly | Thr | Phe | Thr | Ser | Asp | Tyr | Ser | Lys | Gln | Leu | Glu | Glu | Glu |
| 216 | 6723 | 216 | | His | AIB | His | Gly | Thr | Phe | Thr | Ser | Asp | Tyr | Ser | Lys | Gln | Leu | Glu | Glu | Glu |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | | Lys | Lys | | |
| Arg | Val | Arg | Leu | Phe | Ile | Glu | Trp | Leu | Lys | Asn | Ala | Gly | Pro | Ser | Ser | Gly | His | | Pro | Pro | Pro | Gly | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Leu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | His | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | His | Leu | Phe | Ile | Glu | Trp | Leu | Lys | His | Gly | Gly | Pro | Ser | Ser | Gly | His | | Pro | Pro | Pro | Gly | | Lys | | |
| Arg | Val | His | Leu | Phe | Ile | Glu | Trp | Leu | Lys | Ala | Gly | Gly | Pro | Ser | Ser | Gly | His | | Pro | Pro | Pro | Gly | | Lys | | |
| Arg | Val | His | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Leu | Phe | Ile | Glu | Trp | Leu | Lys | His | Gly | Gly | Pro | Ser | Ser | Gly | His | | Pro | Pro | Pro | | Lys | Lys | | |
| Arg | Val | His | Leu | Phe | Ile | Glu | Trp | Leu | Lys | His | Gly | Gly | Pro | Ser | Ser | Gly | His | | Pro | Pro | Pro | | Lys | Lys | | |
| Arg | Val | His | Leu | Phe | Ile | Glu | Trp | Leu | Lys | Asn | Ala | Gly | Pro | Ser | Ser | Gly | His | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | His | | Pro | Pro | Pro | | | Lys | | |
| Arg | Val | His | Leu | Phe | Ile | Glu | Trp | Leu | Lys | His | Gly | Gly | Pro | Ser | Ser | Gly | His | | Pro | Pro | Pro | Gly | Lys | Lys | | |
| Arg | Val | His | Leu | Phe | Ile | Glu | Trp | Leu | Lys | His | Gly | Gly | Pro | Ser | Ser | Gly | His | | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | His | Glu | Phe | Ile | Glu | Trp | Leu | Lys | Gln | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | Ala | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | His | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | Gln | Gly | Gly | Pro | Ser | Ser | Gly | His | | Pro | Pro | Pro | Gly | Lys | Lys | | |
| Arg | Val | Arg | Glu | Phe | Ile | Glu | Trp | Leu | Lys | Asn | Ala | Gly | Pro | Ser | Ser | Gly | Ala | | Pro | Pro | Pro | Gly | | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 193 | 4 | 9 | 6 | 3.2 | 2 | 122 |
| 16 | 194 | 1 | 2 | 2 | 1.7 | | |
| 16 | 195 | | | 2 | 1.4 | | |
| 18 | 196 | 2 | 10 | 4 | 1.5 | 2 | 55 |
| 16 | 197 | 1 | 13 | 2 | 0.6 | | |
| 16 | 198 | | | 2 | 0.8 | | |
| 18 | 199 | 2 | 4 | 2 | 1.6 | 1 | 73 |
| 18 | 200 | 1 | 8 | 2 | 2.4 | | |
| 18 | 201 | 2 | 8 | 2 | 2.1 | | |
| 18 | 202 | 1 | 6 | 2 | 3.7 | | |
| 18 | 203 | 1 | 6 | 2 | 2.9 | | |
| 18 | 204 | 1 | 3 | 2 | 2.9 | | |
| 16 | 205 | | | 2 | 0.7 | | |
| 16 | 206 | | | 2 | 1.5 | | |
| 18 | 207 | 2 | 6 | 2 | 2 | 1 | 89 |
| 16 | 208 | 1 | 4 | 2 | 0.7 | | |
| 18 | 209 | 1 | 6 | 2 | 2.5 | | |
| 18 | 210 | 1 | 8 | 2 | 2 | | |
| 18 | 211 | 2 | 6 | 2 | 1.7 | | |
| 18 | 212 | 1 | 0 | 2 | 1.7 | | |
| 18 | 213 | 1 | 9 | 2 | 1.7 | | |
| 18 | 214 | 1 | -3 | 2 | 1.9 | | |
| 18 | 215 | 1 | 0 | 2 | 2.4 | | |
| 18 | 216 | 1 | 2 | 2 | 3.8 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| 217 | 6724 | 217 | | His | AIB | His | Gly | Thr | Phe | Thr | Ser | Asp | Tyr | Ser | Lys | Gln | Leu | Glu | Glu | Lys |
| 218 | 6725 | 218 | | His | AIB | His | Gly | Thr | Phe | Thr | Ser | Asp | Tyr | Ser | Lys | Gln | Leu | Glu | Glu | Lys |
| 219 | 6726 | 219 | | His | AIB | His | Gly | Thr | Phe | Thr | Ser | Asp | Tyr | Ser | Lys | Gln | Leu | Glu | Glu | Glu |
| 220 | 6727 | 220 | | His | AIB | His | Gly | Thr | Phe | Thr | Ser | Asp | Tyr | Ser | Lys | Gln | Leu | Glu | Glu | Glu |
| 221 | 6728 | 221 | | His | AIB | His | Gly | Thr | Phe | Thr | Ser | Asp | Tyr | Ser | Lys | Gln | Leu | Glu | Glu | Glu |
| 222 | 6729 | 222 | | His | AIB | His | Gly | Thr | Phe | Thr | Ser | Asp | Tyr | Ser | Lys | Gln | Leu | Glu | Glu | Glu |
| 223 | 6730 | 223 | | His | AIB | His | Gly | Thr | Phe | Thr | Ser | Asp | Tyr | Ser | Lys | Gln | Leu | Glu | Glu | Glu |
| 224 | 6731 | 224 | dupl 6920 | His | AIB | His | Gly | Thr | Phe | Thr | Ser | Asp | Tyr | Ser | Lys | Gln | Leu | Glu | Glu | Glu |
| 225 | 6732 | 225 | dupl 6872 | His | AIB | His | Gly | Thr | Phe | Thr | Ser | Asp | Tyr | Ser | Lys | Gln | Leu | Glu | Glu | Glu |
| 226 | 6733 | 226 | | His | AIB | His | Gly | Thr | Phe | Thr | Ser | Asp | Tyr | Ser | Lys | Gln | Leu | Glu | Glu | Lys |
| 227 | 6734 | 227 | | His | AIB | His | Gly | Thr | Phe | Thr | Ser | Asp | Tyr | Ser | Lys | Gln | Leu | Glu | Glu | Lys |
| 228 | 6735 | 228 | dupl 6869 | His | AIB | His | Gly | Thr | Phe | Thr | Ser | Asp | Tyr | Ser | Lys | Gln | Leu | Glu | Glu | Glu |
| 229 | 6736 | 229 | | His | AIB | His | Gly | Thr | Phe | Thr | Ser | Asp | Tyr | Ser | Lys | Gln | Leu | Glu | Glu | Glu |
| 230 | 6737 | 230 | dupl 6915 | His | AIB | His | Gly | Thr | Phe | Thr | Ser | Asp | Tyr | Ser | Lys | Gln | Leu | Glu | Glu | Glu |
| 231 | 6738 | 231 | | His | AIB | His | Gly | Thr | Phe | Thr | Ser | Asp | Tyr | Ser | Lys | Gln | Leu | Glu | Glu | Glu |
| 232 | 6739 | 232 | | His | AIB | His | Gly | Thr | Phe | Thr | Ser | Asp | Tyr | Ser | Lys | Gln | Leu | Glu | Glu | Glu |
| 233 | 6740 | 233 | | His | AIB | His | Gly | Thr | Phe | Thr | Ser | Asp | Tyr | Ser | Lys | Gln | Leu | Glu | Glu | Glu |
| 234 | 6741 | 234 | | His | AIB | His | Gly | Thr | Phe | Thr | Ser | Asp | Tyr | Ser | Lys | Gln | Leu | Glu | Glu | Glu |
| 235 | 6742 | 235 | | His | AIB | His | Gly | Thr | Phe | Thr | Ser | Asp | Tyr | Ser | Lys | Gln | Leu | Glu | Glu | Glu |
| 236 | 6743 | 236 | | His | AIB | His | Gly | Thr | Phe | Thr | Ser | Asp | Tyr | Ser | Lys | Gln | Leu | Glu | Glu | Glu |
| 237 | 6744 | 237 | | His | AIB | His | Gly | Thr | Phe | Thr | Ser | Asp | Tyr | Ser | Lys | Gln | Leu | Glu | Glu | Glu |
| 238 | 6745 | 238 | | His | AIB | His | Gly | Thr | Phe | Thr | Ser | Asp | Tyr | Ser | Lys | Gln | Leu | Glu | Glu | Glu |
| 239 | 6746 | 239 | | His | AIB | His | Gly | Thr | Phe | Thr | Ser | Asp | Tyr | Ser | Lys | Gln | Leu | Glu | Glu | Lys |
| 240 | 6747 | 240 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | His | Glu | Phe | Ile | Glu | Trp | Leu | Lys | His | Gly | Gly | Pro | Ser | Ser | Gly | His | | Pro | Pro | Pro | | Lys | Lys | | |
| Ala | Val | His | Glu | Phe | Ile | Glu | Trp | Leu | Lys | His | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | His | Gly | Gly | Pro | Ser | Ser | Gly | His | | Pro | Pro | Pro | | Lys | Lys | | |
| Arg | Val | His | Glu | Phe | Ile | Glu | Trp | Leu | Lys | His | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | His | Leu | Phe | Ile | Glu | Trp | Leu | Lys | His | Gly | Gly | Pro | Ser | Ser | Gly | Ala | | Pro | Pro | Pro | Gly | | Lys | | |
| Arg | Val | His | Leu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Asn | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Glu | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Gln | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | Lys | | Pro | Pro | Pro | Gly | | Lys | | |
| Arg | Val | His | Leu | Phe | Ile | Glu | Trp | Leu | Lys | Ala | Gly | Gly | Pro | Ser | Ser | Gly | Asn | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | Glu | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | Gln | | Pro | Pro | Pro | | Lys | Lys | | |
| Ala | Val | His | Leu | Phe | Ile | Glu | Trp | Leu | Lys | Ala | Gly | Gly | Pro | Ser | Ser | Gly | Glu | | Pro | Pro | Pro | Gly | | Lys | | |
| Ala | Val | His | Leu | Phe | Ile | Glu | Trp | Leu | Lys | Ala | Gly | Gly | Pro | Ser | Ser | Gly | Gln | | Pro | Pro | Pro | Gly | | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 16 | 217 | | | 2 | 1.2 | | |
| 16 | 218 | | | 2 | 0.9 | | |
| 16 | 219 | | | 2 | 1.1 | | |
| 16 | 220 | | | 2 | 1.3 | | |
| 16 | 221 | 1 | -1 | 2 | 0.9 | | |
| 18 | 222 | 2 | 5 | 2 | 1.6 | 1 | 60 |
| 18 | 223 | 1 | 2 | 2 | 2.2 | | |
| 18 | 224 | 1 | 5 | 2 | 2.5 | | |
| 18 | 225 | 2 | 4 | 4 | 2.3 | 1 | 100 |
| 18 | 226 | 2 | 6 | 2 | 2.6 | | |
| 18 | 227 | 2 | 10 | 2 | 3 | 1 | 74 |
| 18 | 228 | 2 | 5 | 6 | 2.6 | 1 | 106 |
| 18 | 229 | 1 | 1 | 2 | 2.1 | | |
| 18 | 230 | 1 | 4 | 2 | 3.4 | | |
| 18 | 231 | 1 | 5 | 5 | 2.3 | 1 | 101 |
| 18 | 232 | 1 | 2 | 2 | 1.8 | | |
| 18 | 233 | 1 | 4 | 2 | 2.4 | | |
| 18 | 234 | 2 | 6 | 2 | 2.8 | 1 | 89 |
| 18 | 235 | 1 | 6 | 2 | 1.2 | | |
| 18 | 236 | 1 | 5 | 2 | 2.5 | | |
| 18 | 237 | 1 | 4 | 2 | 2.1 | | |
| 18 | 238 | 1 | 6 | 2 | 2.2 | 1 | 90 |
| 18 | 239 | 2 | 13 | 2 | 1.9 | 1 | 55 |
| 18 | 240 | 1 | 11 | 2 | 1.9 | 1 | 60 |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 241 | 6748 | 241 | | His | AIB | His | Gly | Thr | Phe | Thr | Ser | Asp | Tyr | Ser | Lys | Gln | Leu | Glu | Glu | Glu |
| 242 | 6749 | 242 | | His | AIB | His | Gly | Thr | Phe | Thr | Ser | Asp | Tyr | Ser | Lys | Gln | Leu | Glu | Glu | Glu |
| 243 | 6750 | 243 | | His | AIB | His | Gly | Thr | Phe | Thr | Ser | Asp | Tyr | Ser | Lys | Gln | Leu | Glu | Glu | Lys |
| 244 | 6751 | 244 | | His | AIB | His | Gly | Thr | Phe | Thr | Ser | Asp | Tyr | Ser | Lys | Gln | Leu | Glu | Glu | Lys |
| 245 | 6752 | 245 | | His | AIB | His | Gly | Thr | Phe | Thr | Ser | Asp | Tyr | Ser | Lys | Gln | Leu | Glu | Glu | Lys |
| 246 | 6753 | 246 | | His | AIB | His | Gly | Thr | Phe | Thr | Ser | Asp | Tyr | Ser | Lys | Gln | Leu | Glu | Glu | Lys |
| 247 | 6754 | 247 | | His | AIB | His | Gly | Thr | Phe | Thr | Ser | Asp | Tyr | Ser | Lys | Gln | Leu | Glu | Glu | Lys |
| 248 | 6755 | 248 | | His | AIB | His | Gly | Thr | Phe | Thr | Ser | Asp | Tyr | Ser | Lys | Gln | Leu | Glu | Glu | Lys |
| 249 | 6756 | 249 | | His | AIB | His | Gly | Thr | Phe | Thr | Ser | Asp | Tyr | Ser | Lys | Gln | Leu | Glu | Glu | Glu |
| 250 | 6757 | 250 | | His | AIB | His | Gly | Thr | Phe | Thr | Ser | Asp | Tyr | Ser | Lys | Gln | Leu | Glu | Glu | Glu |
| 251 | 6758 | 251 | | His | AIB | His | Gly | Thr | Phe | Thr | Ser | Asp | Tyr | Ser | Lys | Gln | Leu | Glu | Glu | Glu |
| 252 | 6759 | 252 | | His | AIB | His | Gly | Thr | Phe | Thr | Ser | Asp | Tyr | Ser | Lys | Gln | Leu | Glu | Glu | Glu |
| 253 | 6760 | 253 | | His | AIB | His | Gly | Thr | Phe | Thr | Ser | Asp | Tyr | Ser | Lys | Gln | Leu | Glu | Glu | Glu |
| 254 | 6761 | 254 | | His | AIB | His | Gly | Thr | Phe | Thr | Ser | Asp | Leu | Ser | Lys | Gln | Leu | Glu | Glu | Glu |
| 255 | 6762 | 255 | | His | AIB | His | Gly | Thr | Phe | Thr | Ser | Asp | Tyr | Ser | Lys | Gln | Leu | Glu | Glu | Glu |
| 256 | 6763 | 256 | | His | AIB | His | Gly | Thr | Phe | Thr | Ser | Asp | Leu | Ser | Lys | Gln | Leu | Glu | Glu | Glu |
| 257 | 6764 | 257 | | His | AIB | His | Gly | Thr | Phe | Thr | Ser | Asp | Tyr | Ser | Lys | Gln | Leu | Glu | Glu | Glu |
| 258 | 6765 | 258 | | His | AIB | His | Gly | Thr | Phe | Thr | Ser | Asp | Tyr | Ser | Lys | Gln | Leu | Glu | Glu | Lys |
| 259 | 6766 | 259 | | His | AIB | His | Gly | Thr | Phe | Thr | Ser | Asp | Tyr | Ser | Lys | Gln | Leu | Glu | Glu | Lys |
| 260 | 6767 | 260 | | His | AIB | His | Gly | Thr | Phe | Thr | Ser | Asp | Tyr | Ser | Lys | Gln | Leu | Glu | Glu | Lys |
| 261 | 6768 | 261 | dupl 6861 | His | AIB | His | Gly | Thr | Phe | Thr | Ser | Asp | Tyr | Ser | Lys | Gln | Leu | Glu | Glu | Lys |
| 262 | 6769 | 262 | | His | AIB | His | Gly | Thr | Phe | Thr | Ser | Asp | Tyr | Ser | Lys | Gln | Leu | Glu | Glu | Glu |
| 263 | 6770 | 263 | | His | AIB | His | Gly | Thr | Phe | Thr | Ser | Asp | Tyr | Ser | Lys | Gln | Leu | Glu | Glu | Glu |
| 264 | 6771 | 264 | | His | AIB | His | Gly | Thr | Phe | Thr | Ser | Asp | Tyr | Ser | Lys | Gln | Leu | Glu | Glu | Glu |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Asn | Gly | Gly | Pro | Ser | Ser | Gly | Ala | | Pro | Pro | Pro | Gly | | Lys | | |
| Arg | Val | Arg | Leu | Phe | Ile | Glu | Trp | Leu | Lys | Asn | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Gln | Gly | Gly | Pro | Ser | Ser | Gly | Ala | | Pro | Pro | Pro | Gly | | Lys | | |
| Arg | Val | Arg | Glu | Phe | Ile | Glu | Trp | Leu | Lys | Gln | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | His | Gly | Gly | Pro | Ser | Ser | Gly | His | | Pro | Pro | Pro | Gly | | Lys | | |
| Arg | Val | His | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | His | Glu | Phe | Ile | Glu | Trp | Leu | Lys | Ala | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | His | | Pro | Pro | Pro | Gly | | Lys | | |
| Arg | Val | Arg | Leu | Phe | Ile | Glu | Trp | Leu | Lys | His | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | His | Glu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | His | Gly | Gly | Pro | Ser | Ser | Gly | Lys | | Pro | Pro | Pro | | Lys | Lys | | |
| Arg | Val | Arg | Glu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Leu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | Lys | Ser | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | Gln | Ser | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | His | Ser | Pro | Pro | Pro | Gly | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 241 | 2 | 11 | 2 | 1.7 | 1 | 60 |
| 18 | 242 | 2 | 9 | 2 | 1.5 | 1 | 39 |
| 18 | 243 | 2 | 12 | 2 | 1.5 | 1 | 55 |
| 18 | 244 | 2 | 13 | 3 | 2.5 | 1 | 80 |
| 18 | 245 | 1 | 5 | 2 | 2 | | |
| 18 | 246 | 2 | 12 | 3 | 1.7 | 1 | 32 |
| 18 | 247 | 2 | 9 | 2 | 1.1 | 1 | 59 |
| 18 | 248 | 2 | 10 | 2 | 2.6 | 1 | 48 |
| 18 | 249 | 2 | 10 | 2 | 1.2 | 1 | 60 |
| 18 | 250 | 1 | 8 | 2 | 1.5 | | |
| 18 | 251 | 2 | 10 | 6 | 1.7 | 1 | 105 |
| 18 | 252 | 1 | 6 | 3 | 2.5 | | |
| 18 | 253 | 2 | 5 | 3 | 2 | | |
| 18 | 254 | 1 | 3 | 2 | 2.3 | | |
| 18 | 255 | 1 | 3 | 2 | 2.2 | | |
| 18 | 256 | 1 | 2 | 2 | 3.9 | | |
| 18 | 257 | 1 | 1 | 2 | 2.9 | | |
| 18 | 258 | 2 | 10 | 2 | 1.6 | | |
| 18 | 259 | 2 | 11 | 2 | 2.4 | | |
| 18 | 260 | 1 | 9 | 2 | 2.7 | 1 | 72 |
| 18 | 261 | 3 | 12 | 5 | 2.3 | 2 | 93 |
| 18 | 262 | 1 | 2 | 2 | 2.7 | | |
| 18 | 263 | 1 | 2 | 2 | 2.1 | | |
| 18 | 264 | 1 | 0 | 2 | 2.7 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 265 | 6774 | 265 | | His | AIB | His | Gly | Thr | Phe | Thr | Ser | Asp | Tyr | Ser | Lys | Gln | Leu | Glu | Glu | Glu |
| 266 | 6775 | 266 | | His | AIB | His | Gly | Thr | Phe | Thr | Ser | Asp | Tyr | Ser | Lys | Gln | Leu | Glu | Glu | Glu |
| 267 | 6776 | 267 | | His | AIB | His | Gly | Thr | Phe | Thr | Ser | Asp | Tyr | Ser | Lys | Gln | Leu | Glu | Glu | Glu |
| 268 | 6777 | 268 | | His | AIB | His | Gly | Thr | Phe | Thr | Ser | Asp | Tyr | Ser | Lys | Gln | Leu | Glu | Glu | Lys |
| 269 | 6778 | 269 | | His | AIB | His | Gly | Thr | Phe | Thr | Ser | Asp | Tyr | Ser | Lys | Gln | Leu | Glu | Glu | Lys |
| 270 | 6779 | 270 | | His | AIB | His | Gly | Thr | Phe | Thr | Ser | Asp | Tyr | Ser | Lys | Gln | Leu | Glu | Glu | Lys |
| 271 | 6780 | 271 | | His | AIB | His | Gly | Thr | Phe | Thr | Ser | Asp | Tyr | Ser | Lys | Gln | Leu | Glu | Glu | Lys |
| 272 | 6781 | 272 | | His | AIB | His | Gly | Thr | Phe | Thr | Ser | Asp | Tyr | Ser | Lys | Gln | Leu | Glu | Glu | Glu |
| 273 | 6782 | 273 | | His | AIB | His | Gly | Thr | Phe | Thr | Ser | Asp | Tyr | Ser | Lys | Gln | Leu | Glu | Glu | Lys |
| 274 | 6783 | 274 | | His | AIB | His | Gly | Thr | Phe | Thr | Ser | Asp | Tyr | Ser | Lys | Gln | Leu | Glu | Glu | Lys |
| 275 | 6787 | 275 | | His | AIB | His | Gly | Thr | Phe | Thr | Ser | Asp | Tyr | Ser | Lys | Gln | Leu | Glu | Glu | Lys |
| 276 | 6788 | 276 | | His | AIB | His | Gly | Thr | Phe | Thr | Ser | Asp | Tyr | Ser | Lys | Gln | Leu | Glu | Glu | Glu |
| 277 | 6790 | 277 | | His | AIB | His | Gly | Thr | Phe | Thr | Ser | Asp | Tyr | Ser | Lys | Gln | Leu | Glu | Glu | Lys |
| 278 | 6795 | 278 | | His | AIB | His | Gly | Thr | Phe | Thr | Ser | Asp | Tyr | Ser | Lys | Gln | Leu | Glu | Glu | Glu |
| 279 | 6796 | 279 | | His | AIB | His | Gly | Thr | Phe | Thr | Ser | Asp | Tyr | Ser | Lys | Gln | Leu | Glu | Glu | Glu |
| 280 | 6797 | 280 | | His | AIB | His | Gly | Thr | Phe | Thr | Ser | Asp | Tyr | Ser | Lys | Gln | Leu | Glu | Glu | Lys |
| 281 | 6798 | 281 | | His | AIB | His | Gly | Thr | Phe | Thr | Ser | Asp | Tyr | Ser | Lys | Gln | Leu | Glu | Glu | Glu |
| 282 | 6799 | 282 | | His | AIB | His | Gly | Thr | Phe | Thr | Ser | Asp | Tyr | Ser | Lys | Gln | Leu | Glu | Glu | Glu |
| 283 | 6800 | 283 | | His | AIB | His | Gly | Thr | Phe | Thr | Ser | Asp | Tyr | Ser | Lys | Gln | Leu | Glu | Glu | Lys |
| 284 | 6801 | 284 | | His | AIB | His | Gly | Thr | Phe | Thr | Ser | Asp | Tyr | Ser | Lys | Gln | Leu | Glu | Glu | Lys |
| 285 | 6802 | 285 | | His | AIB | His | Gly | Thr | Phe | Thr | Ser | Asp | Tyr | Ser | Lys | Gln | Leu | Glu | Glu | Lys |
| 286 | 6803 | 286 | | His | AIB | His | Gly | Thr | Phe | Thr | Ser | Asp | Tyr | Ser | Lys | Gln | Leu | Glu | Glu | Lys |
| 287 | 6804 | 287 | | His | AIB | His | Gly | Thr | Phe | Thr | Ser | Asp | Tyr | Ser | Lys | Gln | Leu | Glu | Glu | Lys |
| 288 | 6805 | 288 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Lys | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Lys | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Gln | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | Arg | Leu | Phe | Ile | Glu | Trp | Leu | Lys | Ala | Gly | Gly | Pro | Ser | Ser | Gly | His | | Pro | Pro | Pro | Gly | | Lys | | |
| Ala | Val | Arg | Leu | Phe | Ile | Glu | Trp | Leu | Lys | Ala | Gly | Gly | Pro | Ser | Ser | Gly | Lys | | Pro | Pro | Pro | Gly | | Lys | | |
| Ala | Val | His | Leu | Phe | Ile | Glu | Trp | Leu | Lys | Ala | Gly | Gly | Pro | Ser | Ser | Gly | Lys | | Pro | Pro | Pro | Gly | | Lys | | |
| Ala | Val | His | Leu | Phe | Ile | Glu | Trp | Leu | Lys | Ala | Gly | Gly | Pro | Ser | Ser | Gly | Glu | | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | His | | Pro | Pro | Pro | Gly | | Lys | | |
| Ala | Val | His | Leu | Phe | Ile | Glu | Trp | Leu | Lys | Ala | Gly | Gly | Pro | Ser | Ser | Gly | His | | Pro | Pro | Pro | Gly | | Lys | | |
| Ala | Val | His | Leu | Phe | Ile | Glu | Trp | Leu | Lys | Ala | Gly | Gly | Pro | Ser | Ser | Gly | Asn | | Pro | Pro | Pro | Gly | | Lys | | |
| Ala | Val | Arg | Leu | Phe | Ile | Glu | Trp | Leu | Lys | Ala | Gly | Gly | Pro | Ser | Ser | Gly | Glu | | Pro | Pro | Pro | Gly | | Lys | | |
| Arg | Val | Lys | Leu | Phe | Ile | Glu | Trp | Leu | Lys | Ala | Gly | Gly | Pro | Ser | Ser | Gly | Glu | | Pro | Pro | Pro | Gly | | Lys | | |
| Ala | Val | Lys | Leu | Phe | Ile | Glu | Trp | Leu | Lys | Ala | Gly | Gly | Pro | Ser | Ser | Gly | Glu | | Pro | Pro | Pro | Gly | | Lys | | |
| Arg | Val | Arg | Leu | Phe | Ile | Glu | Trp | Leu | Lys | Ala | Gly | Gly | Pro | Ser | His | Gly | His | | Pro | Pro | Pro | Gly | | Lys | | |
| Arg | Val | Arg | Leu | Phe | Ile | Glu | Trp | Leu | Lys | Ala | Gly | Gly | Pro | Ser | His | Gly | His | His | Pro | Pro | Pro | Gly | | Lys | | |
| Ala | Val | His | Leu | Phe | Ile | Glu | Trp | Leu | Lys | Ala | Gly | Gly | Pro | Ser | His | Gly | His | | Pro | Pro | Pro | Gly | | Lys | | |
| Arg | Val | His | Leu | Phe | Ile | Glu | Trp | Leu | Lys | Ala | Gly | Gly | Pro | Ser | Ser | Gly | Glu | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Glu | | Pro | Pro | Pro | Gly | | Lys | | |
| Arg | Val | Arg | Glu | Phe | Ile | Glu | Trp | Leu | Lys | Gln | Gly | Gly | Pro | Ser | Ser | Gly | Glu | | Pro | Pro | Pro | Gly | | Lys | | |
| Arg | Val | His | Leu | Phe | Ile | Glu | Trp | Leu | Lys | Gln | Gly | Gly | Pro | Ser | Ser | Gly | Glu | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | Glu | | Pro | Pro | Pro | Gly | | Lys | | |
| Arg | Val | His | Leu | Phe | Ile | Glu | Trp | Leu | Lys | Ala | Gly | Gly | Pro | Ser | Ser | Gly | Glu | | Pro | Pro | Pro | Gly | | Lys | | |
| Arg | Val | Arg | Glu | Phe | Ile | Glu | Trp | Leu | Lys | His | Gly | Gly | Pro | Ser | Ser | Gly | Glu | | Pro | Pro | Pro | Gly | | Lys | | |
| Arg | Val | His | Leu | Phe | Ile | Glu | Trp | Leu | Lys | His | Gly | Gly | Pro | Ser | Ser | Gly | Glu | | Pro | Pro | Pro | Gly | | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 265 | 1 | 7 | 2 | 1.5 | | |
| 18 | 266 | 1 | 3 | 2 | 1.6 | | |
| 18 | 267 | 1 | 7 | 2 | 1.1 | | |
| 18 | 268 | 1 | 11 | 2 | 2.5 | 1 | 40 |
| 18 | 269 | 2 | 15 | 4 | 2.6 | 1 | 99 |
| 18 | 270 | 1 | 11 | 6 | 2.1 | 1 | 93 |
| 18 | 271 | 2 | 10 | 2 | 1.8 | | |
| 18 | 272 | 2 | 5 | 2 | 1.5 | | |
| 18 | 273 | 2 | 10 | 2 | 2.5 | | |
| 18 | 274 | 2 | 14 | 2 | 1.8 | 1 | 44 |
| 18 | 275 | 2 | 11 | 3 | 2.3 | | |
| 18 | 276 | 2 | 5 | 2 | 1.2 | | |
| 18 | 277 | 2 | 11 | 2 | 1.5 | | |
| 18 | 278 | 2 | 7 | 3 | 2.9 | | |
| 18 | 279 | 2 | 5 | 3 | 3.4 | | |
| 18 | 280 | 2 | 9 | 3 | 3.9 | | |
| 18 | 281 | 1 | 7 | 2 | 2.1 | | |
| 18 | 282 | 1 | 11 | 2 | 2.7 | | |
| 18 | 283 | 1 | 13 | 2 | 2.4 | 1 | 58 |
| 18 | 284 | 1 | 13 | 2 | 2.2 | 1 | 50 |
| 18 | 285 | 2 | 15 | 2 | 2.5 | 1 | 55 |
| 18 | 286 | 1 | 13 | 2 | 2.6 | 1 | 80 |
| 18 | 287 | 1 | 13 | 2 | 4.1 | 1 | 74 |
| 18 | 288 | 1 | 8 | 2 | 2.5 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 289 | 6806 | 289 | | His | AIB | His | Gly | Thr | Phe | Thr | Ser | Asp | Tyr | Ser | Lys | Gln | Leu | Glu | Glu | Lys |
| 290 | 6807 | 290 | | His | AIB | His | Gly | Thr | Phe | Thr | Ser | Asp | Tyr | Ser | Lys | Gln | Leu | Glu | Glu | Lys |
| 291 | 6808 | 291 | | His | AIB | His | Gly | Thr | Phe | Thr | Ser | Asp | Tyr | Ser | Lys | Gln | Leu | Glu | Glu | Glu |
| 292 | 6809 | 292 | | His | AIB | His | Gly | Thr | Phe | Thr | Ser | Asp | Tyr | Ser | Lys | Gln | Leu | Glu | Glu | Glu |
| 293 | 6810 | 293 | | His | AIB | His | Gly | Thr | Phe | Thr | Ser | Asp | Tyr | Ser | Lys | Gln | Leu | Glu | Glu | Glu |
| 294 | 6811 | 294 | | His | AIB | His | Gly | Thr | Phe | Thr | Ser | Asp | Tyr | Ser | Lys | Gln | Leu | Glu | Glu | Glu |
| 295 | 6812 | 295 | dupl 6865 | His | AIB | His | Gly | Thr | Phe | Thr | Ser | Asp | Tyr | Ser | Lys | Gln | Leu | Glu | Glu | Lys |
| 296 | 6813 | 296 | | His | AIB | His | Gly | Thr | Phe | Thr | Ser | Asp | Tyr | Ser | Lys | Gln | Leu | Glu | Glu | Lys |
| 297 | 6814 | 297 | | His | AIB | His | Gly | Thr | Phe | Thr | Ser | Asp | Tyr | Ser | Lys | Gln | Leu | Glu | Glu | Lys |
| 298 | 6815 | 298 | | His | AIB | His | Gly | Thr | Phe | Thr | Ser | Asp | Tyr | Ser | Lys | Gln | Leu | Glu | Glu | Lys |
| 299 | 6816 | 299 | dupl 7074 | His | AIB | His | Gly | Thr | Phe | Thr | Ser | Asp | Tyr | Ser | Lys | Gln | Leu | Glu | Glu | Lys |
| 300 | 6817 | 300 | | His | AIB | His | Gly | Thr | Phe | Thr | Ser | Asp | Tyr | Ser | Lys | Gln | Leu | Glu | Glu | Lys |
| 301 | 6818 | 301 | dupl 7034 | His | AIB | His | Gly | Thr | Phe | Thr | Ser | Asp | Tyr | Ser | Lys | Gln | Leu | Glu | Glu | Lys |
| 302 | 6819 | 302 | | His | AIB | His | Gly | Thr | Phe | Thr | Ser | Asp | Tyr | Ser | Lys | Gln | Leu | Glu | Glu | Lys |
| 303 | 6820 | 303 | | His | AIB | His | Gly | Thr | Phe | Thr | Ser | Asp | Tyr | Ser | Lys | Gln | Leu | Glu | Glu | Lys |
| 304 | 6821 | 304 | | His | AIB | His | Gly | Thr | Phe | Thr | Ser | Asp | Tyr | Ser | Lys | Gln | Leu | Glu | Glu | Lys |
| 305 | 6822 | 305 | | His | AIB | His | Gly | Thr | Phe | Thr | Ser | Asp | Tyr | Ser | Lys | Gln | Leu | Glu | Glu | Lys |
| 306 | 6823 | 306 | | His | AIB | His | Gly | Thr | Phe | Thr | Ser | Asp | Tyr | Ser | Lys | Gln | Leu | Glu | Glu | Lys |
| 307 | 6824 | 307 | | His | AIB | His | Gly | Thr | Phe | Thr | Ser | Asp | Tyr | Ser | Lys | Gln | Leu | Glu | Glu | Lys |
| 308 | 6825 | 308 | | His | AIB | His | Gly | Thr | Phe | Thr | Ser | Asp | Tyr | Ser | Lys | Gln | Leu | Glu | Glu | Lys |
| 309 | 6826 | 309 | | His | AIB | His | Gly | Thr | Phe | Thr | Ser | Asp | Tyr | Ser | Lys | Gln | Leu | Glu | Glu | Lys |
| 310 | 6827 | 310 | | His | AIB | His | Gly | Thr | Phe | Thr | Ser | Asp | Tyr | Ser | Lys | Gln | Leu | Glu | Glu | Lys |
| 311 | 6828 | 311 | | His | AIB | His | Gly | Thr | Phe | Thr | Ser | Asp | Tyr | Ser | Lys | Gln | Leu | Glu | Glu | Lys |
| 312 | 6829 | 312 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Glu | Phe | Ile | Glu | Trp | Leu | Lys | Ala | Gly | Gly | Pro | Ser | His | Gly | His | | Pro | Pro | Pro | Gly | | Lys | | |
| Arg | Val | His | Leu | Phe | Ile | Glu | Trp | Leu | Lys | Ala | Gly | Gly | Pro | Ser | His | Gly | His | | Pro | Pro | Pro | Gly | | Lys | | |
| Arg | Val | His | Glu | Phe | Ile | Glu | Trp | Leu | Lys | Ala | Gly | Gly | Pro | Ser | Ser | Gly | Glu | | Pro | Pro | Pro | Gly | | Lys | | |
| Arg | Val | His | Glu | Phe | Ile | Glu | Trp | Leu | Lys | Ala | Gly | Gly | Pro | Ser | His | Gly | His | | Pro | Pro | Pro | Gly | | Lys | | |
| Arg | Val | His | Glu | Phe | Ile | Glu | Trp | Leu | Lys | His | Gly | Gly | Pro | Ser | Ser | Gly | Ala | | Pro | Pro | Pro | Gly | | Lys | | |
| Arg | Val | His | Leu | Phe | Ile | Glu | Trp | Leu | Lys | His | Gly | Gly | Pro | Ser | Ser | Gly | His | | Pro | Pro | Pro | Gly | | Lys | | |
| Ala | Val | His | Glu | Phe | Ile | Glu | Trp | Leu | Lys | Ala | Gly | Gly | Pro | Ser | Ser | Gly | Glu | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | His | | Pro | Pro | Pro | Gly | Lys | Lys | | |
| Ala | Val | His | Glu | Phe | Ile | Glu | Trp | Leu | Lys | His | Gly | Gly | Pro | Ser | Ser | Gly | Lys | | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Leu | Phe | Ile | Glu | Trp | Leu | Lys | Ala | Gly | Gly | Pro | Ser | Ser | Gly | His | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | His | Leu | Phe | Ile | Glu | Trp | Leu | Lys | Ala | Gly | Gly | Pro | Ser | Ser | Gly | Glu | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Glu | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Ala | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | Gln | | Pro | Pro | Pro | Gly | | Lys | | |
| Arg | Val | Arg | Glu | Phe | Ile | Glu | Trp | Leu | Lys | Gln | Gly | Gly | Pro | Ser | Ser | Gly | Glu | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | His | | Pro | Pro | Pro | Gly | Lys | Lys | | |
| Arg | Val | Arg | Glu | Phe | Ile | Glu | Trp | Leu | Lys | His | Gly | Gly | Pro | Ser | Ser | Gly | His | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Leu | Phe | Ile | Glu | Trp | Leu | Lys | Ala | Gly | Gly | Pro | Ser | Ser | Gly | Asn | | Pro | Pro | Pro | | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 289 | 2 | 12 | 2 | 4.1 | 1 | 85 |
| 18 | 290 | 1 | 9 | 2 | 4.3 | | |
| 18 | 291 | 1 | 2 | 2 | 2.8 | | |
| 18 | 292 | 1 | 1 | 2 | 5.1 | | |
| 18 | 293 | 1 | 2 | 2 | 3.5 | | |
| 18 | 294 | 1 | 5 | 2 | 2.7 | | |
| 18 | 295 | 2 | 11 | 2 | 3.4 | 1 | 85 |
| 18 | 296 | 2 | 10 | 4 | 3.5 | 2 | 82 |
| 18 | 297 | 2 | 12 | 2 | 4.7 | | |
| 18 | 298 | 1 | 12 | 2 | 3.3 | 1 | 90 |
| 18 | 299 | 2 | 8 | 3 | 2.8 | 1 | 110 |
| 18 | 300 | 1 | 12 | 2 | 3.7 | | |
| 18 | 301 | 8 | 15 | 11 | 1.9 | 3 | 120 |
| 18 | 302 | 1 | 8 | 2 | 4.3 | | |
| 18 | 303 | 2 | 11 | 4 | 3.6 | 2 | 97 |
| 18 | 304 | 2 | 13 | 2 | 3 | | |
| 18 | 305 | 1 | 13 | 2 | 2.7 | 1 | 73 |
| 18 | 306 | 1 | 18 | 4 | 2.3 | 2 | 93 |
| 18 | 307 | 1 | 17 | 2 | 2.4 | 1 | 59 |
| 18 | 308 | 3 | 14 | 6 | 1.9 | 2 | 97 |
| 18 | 309 | 2 | 13 | 6 | 2.3 | 2 | 98 |
| 18 | 310 | 1 | 11 | 2 | 2.7 | 1 | 100 |
| 18 | 311 | 6 | 14 | 6 | 1.4 | 5 | 137 |
| 18 | 312 | 1 | 12 | 2 | 4.2 | 1 | 40 |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 313 | 6830 | 313 | | His | AIB | His | Gly | Thr | Phe | Thr | Ser | Asp | Tyr | Ser | Lys | Gln | Leu | Glu | Glu | Glu |
| 314 | 6831 | 314 | | His | AIB | His | Gly | Thr | Phe | Thr | Ser | Asp | Tyr | Ser | Lys | Gln | Leu | Glu | Glu | Lys |
| 315 | 6833 | 315 | | His | AIB | His | Gly | Thr | Phe | Thr | Ser | Asp | Tyr | Ser | Lys | Gln | Leu | Glu | Glu | Glu |
| 316 | 6834 | 316 | | His | AIB | His | Gly | Thr | Phe | Thr | Ser | Asp | Tyr | Ser | Lys | Gln | Leu | Glu | Glu | Lys |
| 317 | 6835 | 317 | | His | AIB | His | Gly | Thr | Phe | Thr | Ser | Asp | Tyr | Ser | Lys | Gln | Leu | Glu | Glu | Lys |
| 318 | 6836 | 318 | | His | AIB | His | Gly | Thr | Phe | Thr | Ser | Asp | Tyr | Ser | Lys | Gln | Leu | Glu | Glu | Lys |
| 319 | 6837 | 319 | | His | AIB | His | Gly | Thr | Phe | Thr | Ser | Asp | Tyr | Ser | Lys | Gln | Leu | Glu | Glu | Glu |
| 320 | 6838 | 320 | | His | AIB | His | Gly | Thr | Phe | Thr | Ser | Asp | Tyr | Ser | Lys | Gln | Leu | Glu | Glu | Lys |
| 321 | 6839 | 321 | | His | AIB | His | Gly | Thr | Phe | Thr | Ser | Asp | Tyr | Ser | Lys | Gln | Leu | Glu | Glu | Glu |
| 322 | 6840 | 322 | | His | AIB | His | Gly | Thr | Phe | Thr | Ser | Asp | Tyr | Ser | Lys | Gln | Leu | Glu | Glu | Lys |
| 323 | 6841 | 323 | | His | AIB | His | Gly | Thr | Phe | Thr | Ser | Asp | Tyr | Ser | Lys | Gln | Leu | Glu | Glu | Lys |
| 324 | 6860 | 324 | | His | AIB | His | Gly | Thr | Phe | Thr | Ser | Asp | Tyr | Ser | Lys | Gln | Leu | Glu | Glu | Lys |
| 325 | 6861 | 325 | dupl 6768 | His | AIB | His | Gly | Thr | Phe | Thr | Ser | Asp | Tyr | Ser | Lys | Gln | Leu | Glu | Glu | Lys |
| 326 | 6862 | 326 | | His | AIB | His | Gly | Thr | Phe | Thr | Ser | Asp | Tyr | Ser | Lys | Gln | Leu | Glu | Glu | Lys |
| 327 | 6863 | 327 | | His | AIB | His | Gly | Thr | Phe | Thr | Ser | Asp | Tyr | Ser | Lys | Gln | Leu | Glu | Glu | Lys |
| 328 | 6864 | 328 | | His | AIB | His | Gly | Thr | Phe | Thr | Ser | Asp | Tyr | Ser | Lys | Gln | Leu | Glu | Glu | Lys |
| 329 | 6865 | 329 | dupl 6812 | His | AIB | His | Gly | Thr | Phe | Thr | Ser | Asp | Tyr | Ser | Lys | Gln | Leu | Glu | Glu | Lys |
| 330 | 6867 | 330 | dupl 6609 | His | AIB | His | Gly | Thr | Phe | Thr | Ser | Asp | Tyr | Ser | Lys | Gln | Leu | Glu | Glu | Lys |
| 331 | 6868 | 331 | dupl 6699 | His | AIB | His | Gly | Thr | Phe | Thr | Ser | Asp | Tyr | Ser | Lys | Gln | Leu | Glu | Glu | Glu |
| 332 | 6869 | 332 | dupl 6735 | His | AIB | His | Gly | Thr | Phe | Thr | Ser | Asp | Tyr | Ser | Lys | Gln | Leu | Glu | Glu | Glu |
| 333 | 6870 | 333 | dupl 6633 | His | AIB | His | Gly | Thr | Phe | Thr | Ser | Asp | Leu | Ser | Lys | Gln | Leu | Glu | Glu | Lys |
| 334 | 6872 | 334 | dupl 6732 | His | AIB | His | Gly | Thr | Phe | Thr | Ser | Asp | Tyr | Ser | Lys | Gln | Leu | Glu | Glu | Glu |
| 335 | 6873 | 335 | dupl 6629 | His | AIB | His | Gly | Thr | Phe | Thr | Ser | Asp | Leu | Ser | Lys | Gln | Leu | Glu | Glu | Glu |
| 336 | 6887 | 336 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | His | Glu | Phe | Ile | Glu | Trp | Leu | Lys | Ala | Gly | Gly | Pro | Ser | Ser | Gly | Asn | | Pro | Pro | Pro | | Lys | Lys | | |
| Arg | Val | His | Glu | Phe | Ile | Glu | Trp | Leu | Lys | His | Gly | Gly | Pro | Ser | Ser | Gly | Asn | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Asn | | Pro | Pro | Pro | | Lys | Lys | | |
| Arg | Val | Arg | Leu | Phe | Ile | Glu | Trp | Leu | Lys | Gln | Gly | Gly | Pro | Ser | His | Gly | Asn | | Pro | Pro | Pro | Gly | | Lys | | |
| Ala | Val | His | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Asn | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | Asn | | Pro | Pro | Pro | Gly | | Lys | | |
| Arg | Val | His | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Arg | Leu | Phe | Ile | Glu | Trp | Leu | Lys | His | Gly | Gly | Pro | Ser | Ser | Gly | Asn | | Pro | Pro | Pro | Gly | Lys | Lys | | |
| Ala | Val | Lys | Leu | Phe | Ile | Glu | Trp | Leu | Lys | Ala | Gly | Gly | Pro | Ser | Ser | Gly | Asn | | Pro | Pro | Pro | Gly | | Lys | | |
| Arg | Val | Arg | Leu | Phe | Ile | Glu | Trp | Leu | Lys | Ala | Gly | Gly | Pro | Ser | Ser | Gly | Asn | | Pro | Pro | Pro | Gly | | Lys | | |
| Ala | Val | Lys | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Leu | Phe | Ile | Glu | Trp | Leu | Lys | Ala | Gly | Gly | Pro | Ser | Ser | Gly | Asn | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | Asn | | Pro | Pro | Pro | | Lys | Lys | | |
| Ala | Val | His | Glu | Phe | Ile | Glu | Trp | Leu | Lys | Ala | Gly | Gly | Pro | Ser | Ser | Gly | Glu | | Pro | Pro | Pro | | Lys | Lys | | |
| Ala | Val | His | Glu | Phe | Ile | Glu | Trp | Leu | Lys | Ala | Gly | Gly | Pro | Ser | Ser | Gly | Glu | | Pro | Pro | Pro | Gly | Lys | Lys | | |
| Ala | Val | Arg | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | Ala | Gly | Gly | Pro | Ser | Ser | Gly | His | | Pro | Pro | Pro | | Lys | Lys | | |
| Arg | Val | His | Glu | Phe | Ile | Glu | Trp | Leu | Lys | His | Gly | Gly | Pro | Ser | Ser | Gly | Lys | | Pro | Pro | Pro | | Lys | Lys | | |
| Arg | Val | His | Glu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | His | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 313 | 1 | 3 | 2 | 3.8 | | |
| 18 | 314 | 1 | 4 | 2 | 3 | | |
| 18 | 315 | 1 | 7 | 2 | 3.6 | | |
| 18 | 316 | 1 | 7 | 2 | 5.5 | | |
| 18 | 317 | 1 | 7 | 2 | 3 | | |
| 18 | 318 | 1 | 7 | 2 | 2.3 | | |
| 18 | 319 | 1 | 5 | 2 | 2 | | |
| 18 | 320 | 1 | 6 | 2 | 2.9 | | |
| 18 | 321 | 1 | 7 | 2 | 2.1 | | |
| 18 | 322 | 1 | 8 | 2 | 2.3 | | |
| 18 | 323 | 1 | 10 | 2 | 2.5 | | |
| 18 | 324 | 1 | 14 | 6 | 1.9 | 1 | 83 |
| 18 | 325 | 2 | 12 | 6 | 2.2 | 1 | 93 |
| 18 | 326 | 1 | 10 | 2 | 2.4 | | |
| 18 | 327 | 1 | 8 | 2 | 2.2 | | |
| 18 | 328 | 1 | 9 | 2 | 2 | | |
| 18 | 329 | 1 | 10 | 2 | 1.9 | | |
| 18 | 330 | 1 | 15 | 6 | 4.2 | | |
| 18 | 331 | 1 | 9 | 2 | 4 | | |
| 18 | 332 | 1 | 4 | 2 | 3 | | |
| 18 | 333 | 1 | 7 | 2 | 5.1 | | |
| 18 | 334 | 1 | 5 | 2 | 3.5 | | |
| 18 | 335 | 1 | 11 | 2 | 5 | | |
| 18 | 336 | 1 | 10 | 2 | 4 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 337 | 6888 | 337 | | His | AIB | His | Gly | Thr | Phe | Thr | Ser | Asp | Tyr | Ser | Lys | Gln | Leu | Glu | Glu | Lys |
| 338 | 6889 | 338 | | His | AIB | His | Gly | Thr | Phe | Thr | Ser | Asp | Tyr | Ser | Lys | Gln | Leu | Glu | Glu | Lys |
| 339 | 6890 | 339 | | His | AIB | His | Gly | Thr | Phe | Thr | Ser | Asp | Tyr | Ser | Lys | Gln | Leu | Glu | Glu | Lys |
| 340 | 6891 | 340 | | His | AIB | His | Gly | Thr | Phe | Thr | Ser | Asp | Tyr | Ser | Lys | Gln | Leu | Glu | Glu | Lys |
| 341 | 6895 | 341 | | His | AIB | His | Gly | Thr | Phe | Thr | Ser | Asp | Tyr | Ser | Lys | Gln | Leu | Glu | Glu | Lys |
| 342 | 6897 | 342 | | His | AIB | His | Gly | Thr | Phe | Thr | Ser | Asp | Tyr | Ser | Lys | Gln | Leu | Glu | Glu | Lys |
| 343 | 6898 | 343 | | His | AIB | His | Gly | Thr | Phe | Thr | Ser | Asp | Tyr | Ser | Lys | Gln | Leu | Glu | Glu | Lys |
| 344 | 6901 | 344 | | His | AIB | His | Gly | Thr | Phe | Thr | Ser | Asp | Tyr | Ser | Lys | Gln | Leu | Glu | Glu | Lys |
| 345 | 6902 | 345 | | His | AIB | His | Gly | Thr | Phe | Thr | Ser | Asp | Tyr | Ser | Lys | Gln | Leu | Glu | Glu | Lys |
| 346 | 6903 | 346 | | His | AIB | His | Gly | Thr | Phe | Thr | Ser | Asp | Tyr | Ser | Lys | Gln | Leu | Glu | Glu | Lys |
| 347 | 6904 | 347 | | His | AIB | His | Gly | Thr | Phe | Thr | Ser | Asp | Tyr | Ser | Lys | Gln | Leu | Glu | Glu | Lys |
| 348 | 6906 | 348 | | His | AIB | His | Gly | Thr | Phe | Thr | Ser | Asp | Tyr | Ser | Lys | Gln | Leu | Glu | Glu | Lys |
| 349 | 6910 | 349 | | His | AIB | His | Gly | Thr | Phe | Thr | Ser | Asp | Leu | Ser | Lys | Gln | Leu | Glu | Glu | Lys |
| 350 | 6911 | 350 | | His | AIB | His | Gly | Thr | Phe | Thr | Ser | Asp | Leu | Ser | Lys | Gln | Leu | Glu | Glu | Lys |
| 351 | 6912 | 351 | | His | AIB | His | Gly | Thr | Phe | Thr | Ser | Asp | Leu | Ser | Lys | Gln | Leu | Glu | Glu | Glu |
| 352 | 6913 | 352 | dupl 6702 | His | AIB | His | Gly | Thr | Phe | Thr | Ser | Asp | Tyr | Ser | Lys | Gln | Leu | Glu | Glu | Glu |
| 353 | 6914 | 353 | | His | AIB | His | Gly | Thr | Phe | Thr | Ser | Asp | Tyr | Ser | Lys | Gln | Leu | Glu | Glu | Lys |
| 354 | 6915 | 354 | dupl 6737 | His | AIB | His | Gly | Thr | Phe | Thr | Ser | Asp | Tyr | Ser | Lys | Gln | Leu | Glu | Glu | Glu |
| 355 | 6916 | 355 | | His | AIB | His | Gly | Thr | Phe | Thr | Ser | Asp | Tyr | Ser | Lys | Gln | Leu | Glu | Glu | Glu |
| 356 | 6917 | 356 | | His | AIB | His | Gly | Thr | Phe | Thr | Ser | Asp | Tyr | Ser | Lys | Gln | Leu | Glu | Glu | Lys |
| 357 | 6918 | 357 | | His | AIB | His | Gly | Thr | Phe | Thr | Ser | Asp | Tyr | Ser | Lys | Gln | Leu | Glu | Glu | Glu |
| 358 | 6919 | 358 | | His | AIB | His | Gly | Thr | Phe | Thr | Ser | Asp | Tyr | Ser | Lys | Gln | Leu | Glu | Glu | Lys |
| 359 | 6920 | 359 | dupl 6731 | His | AIB | His | Gly | Thr | Phe | Thr | Ser | Asp | Tyr | Ser | Lys | Gln | Leu | Glu | Glu | Glu |
| 360 | 6921 | 360 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | His | Glu | Phe | Ile | Glu | Trp | Leu | Lys | Ala | Gly | Gly | Pro | Ser | His | Gly | Lys | | Pro | Pro | Pro | Gly | Lys | Lys | | |
| Ala | Val | His | Glu | Phe | Ile | Glu | Trp | Leu | Lys | Ala | Gly | Gly | Pro | Ser | His | Gly | Glu | | Pro | Pro | Pro | Gly | Lys | Lys | | |
| Ala | Val | His | Glu | Phe | Ile | Glu | Trp | Leu | Lys | Ala | Gly | Gly | Pro | Ser | His | Gly | Asn | | Pro | Pro | Pro | Gly | Lys | Lys | | |
| Ala | Val | His | Glu | Phe | Ile | Glu | Trp | Leu | Lys | Ala | Gly | Gly | Pro | Ser | His | Gly | His | | Pro | Pro | Pro | Gly | Lys | Lys | | |
| Ala | Val | Arg | Leu | Phe | Ile | Glu | Trp | Leu | Lys | Ala | Gly | Gly | Pro | Ser | Ser | Gly | His | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | His | | Pro | Pro | Pro | Gly | Lys | Lys | | |
| Ala | Val | His | Glu | Phe | Ile | Glu | Trp | Leu | Lys | Ala | Gly | Gly | Pro | Ser | His | Gly | Lys | His | Pro | Pro | Pro | Gly | Lys | Lys | | |
| Arg | Val | Arg | Glu | Phe | Ile | Glu | Trp | Leu | Lys | Ala | Gly | Gly | Pro | Ser | His | Gly | His | His | Pro | Pro | Pro | Gly | Lys | Lys | | |
| Ala | Val | His | Glu | Phe | Ile | Glu | Trp | Leu | Lys | Ala | Gly | Gly | Pro | Ser | His | Gly | His | Lys | Pro | Pro | Pro | Gly | Lys | Lys | | |
| Ala | Val | His | Glu | Phe | Ile | Glu | Trp | Leu | Lys | Ala | Gly | Gly | Pro | Ser | His | Gly | His | Glu | Pro | Pro | Pro | Gly | Lys | Lys | | |
| Arg | Val | Arg | Glu | Phe | Ile | Glu | Trp | Leu | Lys | Ala | Gly | Gly | Pro | Ser | His | Gly | Asn | | Pro | Pro | Pro | Gly | | Lys | | |
| Ala | Val | His | Glu | Phe | Ile | Glu | Trp | Leu | Lys | Ala | Gly | Gly | Pro | Ser | His | Gly | Asn | | Pro | Pro | Pro | Gly | | Lys | | |
| Ala | Val | His | Glu | Phe | Ile | Glu | Trp | Leu | Lys | Ala | Gly | Gly | Pro | Ser | His | Gly | Asn | | Pro | Pro | Pro | Gly | | Lys | | |
| Ala | Val | Arg | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Lys | Glu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | Lys | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Lys | Leu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | His | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | His | Leu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | His | Glu | Phe | Ile | Glu | Trp | Leu | Lys | Ala | Gly | Gly | Pro | Ser | Ser | Gly | His | | Pro | Pro | Pro | | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 337 | 1 | 6 | 2 | 6.3 | | |
| 18 | 338 | 1 | 5 | 2 | 4.5 | | |
| 18 | 339 | 1 | 6 | 2 | 8 | | |
| 18 | 340 | 1 | 5 | 2 | 5.3 | | |
| 18 | 341 | 1 | 13 | 2 | 3.7 | | |
| 18 | 342 | 2 | 14 | 2 | 3.5 | 1 | 85 |
| 18 | 343 | 1 | 6 | 2 | 6.9 | | |
| 18 | 344 | 1 | 2 | 2 | 4 | | |
| 18 | 345 | 1 | 7 | 2 | 5.4 | | |
| 18 | 346 | 1 | 3 | 2 | 5.3 | | |
| 18 | 347 | 1 | 12 | 2 | 2.7 | | |
| 18 | 348 | 1 | 11 | 2 | 3.3 | | |
| 18 | 349 | 1 | 9 | 2 | 5.7 | | |
| 18 | 350 | 1 | 13 | 2 | 7.7 | 1 | 65 |
| 18 | 351 | 2 | 12 | 4 | 3.9 | 1 | 105 |
| 18 | 352 | 2 | 10 | 2 | 2 | | |
| 18 | 353 | 2 | 11 | 2 | 3.6 | 1 | 79 |
| 18 | 354 | 1 | 6 | 2 | 3.6 | | |
| 18 | 355 | 1 | 3 | 2 | 4.5 | | |
| 18 | 356 | 1 | 11 | 2 | 3.8 | 1 | 71 |
| 18 | 357 | 1 | 8 | 2 | 3.9 | | |
| 18 | 358 | 1 | 12 | 2 | 5.2 | 1 | 69 |
| 18 | 359 | 1 | 9 | 2 | 2.7 | | |
| 18 | 360 | 1 | 11 | 2 | 4 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 361 | 6922 | 361 | | His | AIB | His | Gly | Thr | Phe | Thr | Ser | Asp | Val | Ser | Lys | Gln | Leu | Glu | Glu | Lys |
| 362 | 6923 | 362 | | His | AIB | His | Gly | Thr | Phe | Thr | Ser | Asp | Val | Ser | Lys | Gln | Leu | Glu | Glu | Glu |
| 363 | 6924 | 363 | | His | AIB | His | Gly | Thr | Phe | Thr | Ser | Asp | Tyr | Ser | Lys | Gln | Leu | Glu | Glu | Lys |
| 364 | 6925 | 364 | | His | AIB | His | Gly | Thr | Phe | Thr | Ser | Asp | Tyr | Ser | Lys | Gln | Leu | Glu | Glu | Lys |
| 365 | 6926 | 365 | | His | AIB | His | Gly | Thr | Phe | Thr | Ser | Asp | Leu | Ser | Lys | Gln | Leu | Glu | Glu | Lys |
| 366 | 6927 | 366 | | His | AIB | His | Gly | Thr | Phe | Thr | Ser | Asp | Leu | Ser | Lys | Gln | Leu | Glu | Glu | Lys |
| 367 | 6929 | 367 | | His | AIB | His | Gly | Thr | Phe | Thr | Ser | Asp | Tyr | Ser | Lys | Gln | Leu | Glu | Glu | Lys |
| 368 | 6930 | 368 | | His | AIB | His | Gly | Thr | Phe | Thr | Ser | Asp | Tyr | Ser | Lys | Gln | Leu | Glu | Glu | Lys |
| 369 | 6931 | 369 | | His | AIB | His | Gly | Thr | Phe | Thr | Ser | Asp | Tyr | Ser | Lys | Gln | Leu | Glu | Glu | Lys |
| 370 | 6932 | 370 | | His | AIB | His | Gly | Thr | Phe | Thr | Ser | Asp | Tyr | Ser | Lys | Gln | Leu | Glu | Glu | Lys |
| 371 | 6934 | 371 | | His | AIB | His | Gly | Thr | Phe | Thr | Ser | Asp | Tyr | Ser | Lys | Gln | Leu | Glu | Glu | Lys |
| 372 | 6935 | 372 | dupl 6584 | His | AIB | His | Gly | Thr | Phe | Thr | Ser | Asp | Leu | Ser | Lys | Gln | Leu | Glu | Glu | Lys |
| 373 | 6937 | 373 | | His | AIB | His | Gly | Thr | Phe | Thr | Ser | Asp | Tyr | Ser | Lys | Gln | Leu | Glu | Glu | Lys |
| 374 | 6938 | 374 | | His | AIB | His | Gly | Thr | Phe | Thr | Ser | Asp | Tyr | Ser | Lys | Gln | Leu | Glu | Glu | Lys |
| 375 | 6940 | 375 | | His | AIB | His | Gly | Thr | Phe | Thr | Ser | Asp | Tyr | Ser | Lys | Gln | Leu | Glu | Glu | Lys |
| 376 | 6941 | 376 | | His | AIB | His | Gly | Thr | Phe | Thr | Ser | Asp | Tyr | Ser | Lys | Gln | Leu | Glu | Glu | Lys |
| 377 | 6943 | 377 | | His | AIB | His | Gly | Thr | Phe | Thr | Ser | Asp | Tyr | Ser | Lys | Gln | Leu | Glu | Glu | Lys |
| 378 | 6944 | 378 | | His | AIB | His | Gly | Thr | Phe | Thr | Ser | Asp | Tyr | Ser | Lys | Gln | Leu | Glu | Glu | Lys |
| 379 | 6945 | 379 | | His | AIB | His | Gly | Thr | Phe | Thr | Ser | Asp | Tyr | Ser | Lys | Gln | Leu | Glu | Glu | Lys |
| 380 | 6946 | 380 | | His | AIB | His | Gly | Thr | Phe | Thr | Ser | Asp | Tyr | Ser | Lys | Gln | Leu | Glu | Glu | Lys |
| 381 | 6947 | 381 | | His | AIB | His | Gly | Thr | Phe | Thr | Ser | Asp | Tyr | Ser | Lys | Gln | Leu | Glu | Glu | Lys |
| 382 | 6949 | 382 | | His | AIB | His | Gly | Thr | Phe | Thr | Ser | Asp | Tyr | Ser | Lys | Gln | Leu | Glu | Glu | Lys |
| 383 | 6950 | 383 | | His | AIB | His | Gly | Thr | Phe | Thr | Ser | Asp | Tyr | Ser | Lys | Gln | Leu | Glu | Glu | Lys |
| 384 | 6951 | 384 | | His | AIB | His | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | Arg | Leu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | Arg | Leu | Phe | Ile | Glu | Trp | Leu | Lys | Ala | Gly | Gly | Pro | Ser | Ser | Gly | Lys | | Pro | Pro | Pro | | Lys | Lys | Asn | His |
| Ala | Val | Arg | Leu | Phe | Ile | Glu | Trp | Leu | Lys | Ala | Gly | Gly | Pro | Ser | Ser | Gly | His | | Pro | Pro | Pro | | Lys | Lys | Asn | His |
| Ala | Val | Arg | Leu | Phe | Ile | Glu | Trp | Leu | Lys | Ala | Gly | Gly | Pro | Ser | Ser | Gly | Asn | | Pro | Pro | Pro | | Lys | Lys | | |
| Ala | Val | Arg | Leu | Phe | Ile | Glu | Trp | Leu | Lys | Ala | Gly | Gly | Pro | Ser | Ser | Gly | Glu | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | His | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Asn | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Glu | | Pro | Pro | Pro | | Lys | Lys | | |
| Arg | Val | Arg | Glu | Phe | Ile | Glu | Trp | Leu | Lys | Ala | Gly | Gly | Pro | Ser | Ser | Gly | Gln | | Pro | Pro | Pro | | Lys | Lys | | |
| Arg | Val | His | Leu | Phe | Ile | Glu | Trp | Leu | Lys | Gln | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Asn | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | | Lys | | |
| Ala | Val | Arg | Glu | Phe | Ile | Glu | Trp | Leu | Lys | Ala | Gly | Gly | Pro | Ser | Ser | Gly | Asn | | Pro | Pro | Pro | Gly | | Lys | | |
| Ala | Val | Arg | Glu | Phe | Ile | Glu | Trp | Leu | Lys | Ala | Gly | Gly | Pro | Ser | Ser | Gly | Glu | | Pro | Pro | Pro | Gly | | Lys | | |
| Ala | Val | Arg | Glu | Phe | Ile | Glu | Trp | Leu | Lys | Ala | Gly | Gly | Pro | Ser | Ser | Gly | Gln | | Pro | Pro | Pro | Gly | | Lys | | |
| Ala | Val | Arg | Glu | Phe | Ile | Glu | Trp | Leu | Lys | Ala | Gly | Gly | Pro | Ser | Ser | Gly | His | | Pro | Pro | Pro | Gly | | Lys | | |
| Ala | Val | Arg | Glu | Phe | Ile | Glu | Trp | Leu | Lys | Ala | Gly | Gly | Pro | Ser | Ser | Gly | Lys | | Pro | Pro | Pro | Gly | | Lys | | |
| Ala | Val | His | Glu | Phe | Ile | Glu | Trp | Leu | Lys | Ala | Gly | Gly | Pro | Ser | Ser | Gly | Asn | | Pro | Pro | Pro | Gly | | Lys | | |
| Ala | Val | His | Glu | Phe | Ile | Glu | Trp | Leu | Lys | Ala | Gly | Gly | Pro | Ser | Ser | Gly | Glu | | Pro | Pro | Pro | Gly | | Lys | | |
| Ala | Val | His | Glu | Phe | Ile | Glu | Trp | Leu | Lys | Ala | Gly | Gly | Pro | Ser | Ser | Gly | Gln | | Pro | Pro | Pro | Gly | | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 361 | 1 | 14 | 2 | 5.3 | 1 | 50 |
| 18 | 362 | 1 | 10 | 2 | 4.7 | | |
| 18 | 363 | 2 | 13 | 2 | 3.9 | 1 | 49 |
| 18 | 364 | 1 | 11 | 2 | 5.1 | | |
| 18 | 365 | 1 | 11 | 2 | 5.6 | | |
| 18 | 366 | 1 | 13 | 2 | 5.3 | 1 | 72 |
| 18 | 367 | 1 | 8 | 2 | 4.7 | | |
| 18 | 368 | 1 | 10 | 2 | 3.6 | | |
| 18 | 369 | 1 | 10 | 2 | 5.3 | | |
| 18 | 370 | 1 | 4 | 2 | 3.8 | | |
| 18 | 371 | 1 | 7 | 2 | 5 | | |
| 18 | 372 | 1 | 11 | 2 | 3.9 | | |
| 18 | 373 | 2 | 14 | 2 | 2.9 | 1 | 80 |
| 18 | 374 | 2 | 15 | 6 | 2.1 | 1 | 112 |
| 18 | 375 | 2 | 16 | 4 | 2.1 | 1 | 105 |
| 18 | 376 | 2 | 14 | 6 | 2.1 | 1 | 100 |
| 18 | 377 | 2 | 15 | 2 | 1.9 | | |
| 18 | 378 | 2 | 12 | 2 | 1.9 | | |
| 18 | 379 | 2 | 12 | 2 | 1.6 | 1 | 55 |
| 18 | 380 | 1 | 12 | 2 | 1.5 | | |
| 18 | 381 | 2 | 18 | 2 | 1.5 | 1 | 78 |
| 18 | 382 | 1 | 10 | 2 | 1.9 | | |
| 18 | 383 | 1 | 10 | 2 | 1.8 | | |
| 18 | 384 | 1 | 11 | 2 | 1.5 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 385 | 6952 | 385 | | His | AIB | His | Gly | Thr | Phe | Thr | Ser | Asp | Tyr | Ser | Lys | Gln | Leu | Glu | Glu | Lys |
| 386 | 6953 | 386 | | His | AIB | His | Gly | Thr | Phe | Thr | Ser | Asp | Tyr | Ser | Lys | Gln | Leu | Glu | Glu | Lys |
| 387 | 6955 | 387 | | His | AIB | His | Gly | Thr | Phe | Thr | Ser | Asp | Leu | Ser | Lys | Gln | Leu | Glu | Glu | Lys |
| 388 | 6956 | 388 | | His | AIB | His | Gly | Thr | Phe | Thr | Ser | Asp | Tyr | Ser | Lys | Gln | Leu | Glu | Glu | Lys |
| 389 | 6957 | 389 | | His | AIB | His | Gly | Thr | Phe | Thr | Ser | Asp | Tyr | Ser | Lys | Gln | Leu | Glu | Glu | Lys |
| 390 | 6958 | 390 | | His | AIB | His | Gly | Thr | Phe | Thr | Ser | Asp | Leu | Ser | Lys | Gln | Leu | Glu | Glu | Lys |
| 391 | 6959 | 391 | | His | AIB | His | Gly | Thr | Phe | Thr | Ser | Asp | Tyr | Ser | Lys | Gln | Leu | Glu | Glu | Lys |
| 392 | 6960 | 392 | | His | AIB | His | Gly | Thr | Phe | Thr | Ser | Asp | Tyr | Ser | Lys | Gln | Leu | Glu | Glu | Lys |
| 393 | 6961 | 393 | | His | AIB | His | Gly | Thr | Phe | Thr | Ser | Asp | Tyr | Ser | Lys | Gln | Leu | Glu | Glu | Lys |
| 394 | 6962 | 394 | | His | AIB | His | Gly | Thr | Phe | Thr | Ser | Asp | Tyr | Ser | Lys | Gln | Leu | Glu | Glu | Glu |
| 395 | 6964 | 395 | | His | AIB | His | Gly | Thr | Phe | Thr | Ser | Asp | Tyr | Ser | Lys | Gln | Leu | Glu | Glu | Glu |
| 396 | 6965 | 396 | | His | AIB | His | Gly | Thr | Phe | Thr | Ser | Asp | Tyr | Ser | Lys | Gln | Leu | Glu | Glu | Glu |
| 397 | 6966 | 397 | | His | AIB | His | Gly | Thr | Phe | Thr | Ser | Asp | Tyr | Ser | Lys | Gln | Leu | Glu | Glu | Glu |
| 398 | 6967 | 398 | dupl 7022 | His | AIB | His | Gly | Thr | Phe | Thr | Ser | Asp | Tyr | Ser | Lys | Gln | Leu | Glu | Glu | Lys |
| 399 | 6968 | 399 | | His | AIB | His | Gly | Thr | Phe | Thr | Ser | Asp | Tyr | Ser | Lys | Gln | Leu | Glu | Glu | Lys |
| 400 | 6969 | 400 | | His | AIB | His | Gly | Thr | Phe | Thr | Ser | Asp | Tyr | Ser | Lys | Gln | Leu | Glu | Glu | Glu |
| 401 | 6970 | 401 | | His | AIB | His | Gly | Thr | Phe | Thr | Ser | Asp | Tyr | Ser | Lys | Gln | Leu | Glu | Glu | Lys |
| 402 | 6971 | 402 | | His | AIB | His | Gly | Thr | Phe | Thr | Ser | Asp | Tyr | Ser | Lys | Gln | Leu | Glu | Glu | Glu |
| 403 | 6972 | 403 | | His | AIB | His | Gly | Thr | Phe | Thr | Ser | Asp | Tyr | Ser | Lys | Gln | Leu | Glu | Glu | Lys |
| 404 | 6973 | 404 | | His | AIB | His | Gly | Thr | Phe | Thr | Ser | Asp | Tyr | Ser | Lys | Gln | Leu | Glu | Glu | Lys |
| 405 | 6974 | 405 | | His | AIB | His | Gly | Thr | Phe | Thr | Ser | Asp | Tyr | Ser | Lys | Gln | Leu | Glu | Glu | Glu |
| 406 | 6976 | 406 | | His | AIB | His | Gly | Thr | Phe | Thr | Ser | Asp | Tyr | Ser | Lys | Gln | Leu | Glu | Glu | Glu |
| 407 | 6977 | 407 | | His | AIB | His | Gly | Thr | Phe | Thr | Ser | Asp | Tyr | Ser | Lys | Gln | Leu | Glu | Glu | Glu |
| 408 | 6978 | 408 | | His | AIB | His | Gly | Thr | Phe | Thr | Ser | Asp | Tyr | Ser | Lys | Gln | Leu | Glu | Glu | Glu |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | His | Glu | Phe | Ile | Glu | Trp | Leu | Lys | Ala | Gly | Gly | Pro | Ser | Ser | Gly | His | | Pro | Pro | Pro | Gly | | Lys | | |
| Ala | Val | His | Glu | Phe | Ile | Glu | Trp | Leu | Lys | Ala | Gly | Gly | Pro | Ser | Ser | Gly | Lys | | Pro | Pro | Pro | Gly | | Lys | | |
| Arg | Val | Arg | Glu | Phe | Ile | Glu | Trp | Leu | Lys | His | Gly | Gly | Pro | Ser | Ser | Gly | Lys | | Pro | Pro | Pro | | Lys | Lys | | |
| Ala | Val | Arg | Glu | Phe | Ile | Glu | Trp | Leu | Lys | Ala | Gly | Gly | Pro | Ser | Ser | Gly | Lys | | Pro | Pro | Pro | | Lys | Lys | | |
| Ala | Val | Lys | Glu | Phe | Ile | Glu | Trp | Leu | Lys | Ala | Gly | Gly | Pro | Ser | Ser | Gly | Lys | | Pro | Pro | Pro | | Lys | Lys | | |
| Arg | Val | Arg | Glu | Phe | Ile | Glu | Trp | Leu | Lys | His | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | His | Gly | Gly | Pro | Ser | Ser | Gly | Lys | | Pro | Pro | Pro | Gly | Lys | Lys | | |
| Ala | Val | Lys | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Lys | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Arg | Val | Lys | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Lys | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Arg | Val | Lys | Glu | Phe | Ile | Glu | Trp | Leu | Lys | Ala | Gly | Gly | Pro | Ser | Ser | Gly | His | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Lys | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | Asn | His |
| Ala | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | Asn | His |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | Asn | His |
| Ala | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | Asn | His |
| Arg | Val | His | Glu | Phe | Ile | Glu | Trp | Leu | Lys | His | Gly | Gly | Pro | Ser | Ser | Gly | Lys | | Pro | Pro | Pro | Gly | Lys | Lys | | |
| Arg | Val | Arg | Leu | Phe | Ile | Glu | Trp | Leu | Lys | Ala | Gly | Gly | Pro | Ser | Ser | Gly | Gln | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Asn | | Pro | Pro | Pro | | Lys | Lys | | |
| Arg | Val | Arg | Leu | Phe | Ile | Glu | Trp | Leu | Lys | Ala | Gly | Gly | Pro | Ser | Ser | Gly | Glu | | Pro | Pro | Pro | | Lys | Lys | | |
| Arg | Val | Arg | Leu | Phe | Ile | Glu | Trp | Leu | Lys | Ala | Gly | Gly | Pro | Ser | His | Gly | Lys | | Pro | Pro | Pro | | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 385 | 1 | 16 | 2 | 2 | 1 | 83 |
| 18 | 386 | 1 | 16 | 3 | 1.7 | 1 | 99 |
| 18 | 387 | 1 | 10 | 2 | 6.3 | | |
| 18 | 388 | 2 | 14 | 6 | 3.2 | 1 | 70 |
| 18 | 389 | 1 | 6 | 2 | 2.9 | | |
| 18 | 390 | 2 | 16 | 2 | 4.7 | 1 | 61 |
| 18 | 391 | 2 | 15 | 6 | 3 | | |
| 18 | 392 | 2 | 11 | 2 | 2.8 | | |
| 18 | 393 | 1 | 11 | 2 | 2.7 | | |
| 18 | 394 | 1 | 8 | 2 | 2.5 | | |
| 18 | 395 | 1 | 1 | 2 | 3.3 | | |
| 18 | 396 | 1 | 0 | 2 | 2.4 | | |
| 18 | 397 | 1 | 2 | 2 | 2.4 | | |
| 18 | 398 | 4 | 18 | 6 | 2.7 | 3 | 110 |
| 18 | 399 | 3 | 11 | 3 | 2.5 | 1 | 110 |
| 18 | 400 | 1 | 5 | 2 | 2.9 | | |
| 18 | 401 | 1 | 12 | 2 | 2.9 | | |
| 16 | 402 | 1 | 8 | 2 | 0.7 | | |
| 16 | 403 | 1 | 18 | 2 | 1.1 | 1 | 58 |
| 18 | 404 | 1 | 8 | 2 | 3.8 | | |
| 18 | 405 | 1 | 8 | 2 | 6.1 | | |
| 18 | 406 | 1 | 8 | 2 | 5.5 | | |
| 18 | 407 | 1 | 2 | 2 | 5.3 | | |
| 18 | 408 | 1 | 7 | 2 | 6.8 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 409 | 6979 | 409 | | His | AIB | His | Gly | Thr | Phe | Thr | Ser | Asp | Tyr | Ser | Lys | Gln | Leu | Glu | Glu | Glu |
| 410 | 6980 | 410 | | His | AIB | His | Gly | Thr | Phe | Thr | Ser | Asp | Tyr | Ser | Lys | Gln | Leu | Glu | Glu | Glu |
| 411 | 6981 | 411 | | His | AIB | His | Gly | Thr | Phe | Thr | Ser | Asp | Tyr | Ser | Lys | Gln | Leu | Glu | Glu | Glu |
| 412 | 6982 | 412 | | His | AIB | His | Gly | Thr | Phe | Thr | Ser | Asp | Tyr | Ser | Lys | Gln | Leu | Glu | Glu | Lys |
| 413 | 6983 | 413 | | His | AIB | His | Gly | Thr | Phe | Thr | Ser | Asp | Leu | Ser | Lys | Gln | Leu | Glu | Glu | Lys |
| 414 | 6984 | 414 | | His | AIB | His | Gly | Thr | Phe | Thr | Ser | Asp | Tyr | Ser | Lys | Gln | Leu | Glu | Glu | Lys |
| 415 | 6985 | 415 | | His | AIB | His | Gly | Thr | Phe | Thr | Ser | Asp | Tyr | Ser | Lys | Gln | Leu | Glu | Glu | Lys |
| 416 | 6986 | 416 | | His | AIB | His | Gly | Thr | Phe | Thr | Ser | Asp | Tyr | Ser | Lys | Gln | Leu | Glu | Glu | Lys |
| 417 | 6988 | 417 | | His | AIB | His | Gly | Thr | Phe | Thr | Ser | Asp | Tyr | Ser | Lys | Gln | Leu | Glu | Glu | Lys |
| 418 | 6989 | 418 | | His | AIB | His | Gly | Thr | Phe | Thr | Ser | Asp | Tyr | Ser | Lys | Gln | Leu | Glu | Glu | Lys |
| 419 | 6990 | 419 | | His | AIB | His | Gly | Thr | Phe | Thr | Ser | Asp | Tyr | Ser | Lys | Gln | Leu | Glu | Glu | Lys |
| 420 | 6991 | 420 | | His | AIB | His | Gly | Thr | Phe | Thr | Ser | Asp | Tyr | Ser | Lys | Gln | Leu | Glu | Glu | Lys |
| 421 | 6992 | 421 | | His | AIB | His | Gly | Thr | Phe | Thr | Ser | Asp | Tyr | Ser | Lys | Gln | Leu | Glu | Glu | Lys |
| 422 | 6993 | 422 | | His | AIB | His | Gly | Thr | Phe | Thr | Ser | Asp | Tyr | Ser | Lys | Gln | Leu | Glu | Glu | Lys |
| 423 | 6995 | 423 | | His | AIB | His | Gly | Thr | Phe | Thr | Ser | Asp | Tyr | Ser | Lys | Gln | Leu | Glu | Glu | Lys |
| 424 | 6997 | 424 | | His | AIB | His | Gly | Thr | Phe | Thr | Ser | Asp | Tyr | Ser | Lys | Gln | Leu | Glu | Glu | Lys |
| 425 | 6999 | 425 | | His | AIB | His | Gly | Thr | Phe | Thr | Ser | Asp | Tyr | Ser | Lys | Gln | Leu | Glu | Glu | Lys |
| 426 | 7000 | 426 | | His | AIB | His | Gly | Thr | Phe | Thr | Ser | Asp | Tyr | Ser | Lys | Gln | Leu | Glu | Glu | Lys |
| 427 | 7001 | 427 | | His | AIB | His | Gly | Thr | Phe | Thr | Ser | Asp | Tyr | Ser | Lys | Gln | Leu | Glu | Glu | Lys |
| 428 | 7002 | 428 | | His | AIB | His | Gly | Thr | Phe | Thr | Ser | Asp | Leu | Ser | Lys | Gln | Leu | Glu | Glu | Lys |
| 429 | 7003 | 429 | | His | AIB | His | Gly | Thr | Phe | Thr | Ser | Asp | Leu | Ser | Lys | Gln | Leu | Glu | Glu | Lys |
| 430 | 7004 | 430 | | His | AIB | His | Gly | Thr | Phe | Thr | Ser | Asp | Leu | Ser | Lys | Gln | Leu | Glu | Glu | Glu |
| 431 | 7005 | 431 | | His | AIB | His | Gly | Thr | Phe | Thr | Ser | Asp | Val | Ser | Lys | Gln | Leu | Glu | Glu | Lys |
| 432 | 7006 | 432 | | His | AIB | His | Gly | Thr | Phe | Thr | Ser | Asp | Val | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Leu | Phe | Ile | Glu | Trp | Leu | Lys | Asn | Ala | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Asn | Ala | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Asn | Ala | Gly | Pro | Ser | Ser | Gly | Lys | | Pro | Pro | Pro | | Lys | Lys | | |
| Arg | Val | Lys | Glu | Phe | Ile | Glu | Trp | Leu | Lys | Ala | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Asn | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Asn | Ala | Gly | Pro | Ser | Ser | Gly | His | | Pro | Pro | Pro | Gly | | Lys | | |
| Arg | Val | Arg | Glu | Phe | Ile | Glu | Trp | Leu | Lys | His | Gly | Gly | Pro | Ser | Ser | Gly | His | | Pro | Pro | Pro | Gly | | Lys | | |
| Arg | Val | Arg | Glu | Phe | Ile | Glu | Trp | Leu | Lys | Ala | Gly | Gly | Pro | Ser | Ser | Gly | His | Gln | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Gln | His | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | Gln | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Gln | Gln | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Glu | Phe | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | Phe | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | Phe | Pro | Pro | Gly | | Lys | Lys | | |
| Arg | Val | Arg | Glu | Phe | Ile | Glu | Trp | Leu | Lys | Ala | Gly | Gly | Pro | Ser | Ser | Gly | Lys | Gln | Pro | Pro | Gly | | Lys | Lys | | |
| Arg | Val | Arg | Glu | Phe | Ile | Glu | Trp | Leu | Lys | Ala | Gly | Gly | Pro | Ser | Ser | Gly | Pro | Ser | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | Ser | Pro | Pro | Pro | Gly | Lys | Lys | | |
| Arg | Val | Gln | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 409 | 1 | 5 | 2 | 3.8 | | |
| 18 | 410 | 1 | 5 | 2 | 4.5 | | |
| 18 | 411 | 1 | 1 | 2 | 4.9 | | |
| 18 | 412 | 1 | 3 | 2 | 2.9 | | |
| 18 | 413 | 1 | 10 | 2 | 2.6 | | |
| 18 | 414 | 1 | 11 | 3 | 3.8 | | |
| 18 | 415 | 1 | 7 | 3 | 3.6 | | |
| 18 | 416 | 1 | 7 | 3 | 2.7 | | |
| 18 | 417 | 1 | 7 | 3 | 2.8 | | |
| 18 | 418 | 1 | 6 | 2 | 3.5 | | |
| 18 | 419 | 1 | 10 | 2 | 2.8 | | |
| 18 | 420 | 2 | 13 | 2 | 2.6 | | |
| 18 | 421 | 1 | 9 | 2 | 3.4 | | |
| 18 | 422 | 1 | 8 | 2 | 3 | | |
| 18 | 423 | 1 | 13 | 3 | 3 | | |
| 18 | 424 | 1 | 12 | 2 | 3.8 | | |
| 18 | 425 | 1 | 5 | 3 | 5.4 | | |
| 18 | 426 | 1 | 9 | 3 | 3.8 | | |
| 18 | 427 | 1 | 6 | 3 | 1.9 | | |
| 18 | 428 | 3 | 18 | 6 | 2.9 | | |
| 18 | 429 | 4 | 18 | 6 | 2.5 | 2 | 120 |
| 18 | 430 | 1 | 12 | 3 | 2.3 | | |
| 18 | 431 | 3 | 21 | 6 | 2.4 | 2 | 78 |
| 18 | 432 | 2 | 15 | 6 | 2.1 | 2 | 96 |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 433 | 7007 | 433 | | His | AIB | His | Gly | Thr | Phe | Thr | Ser | Asp | Val | Ser | Lys | Gln | Leu | Glu | Glu | Glu |
| 434 | 7008 | 434 | | His | AIB | His | Gly | Thr | Phe | Thr | Ser | Asp | Tyr | Ser | Lys | Gln | Leu | Glu | Glu | Lys |
| 435 | 7009 | 435 | | His | AIB | His | Gly | Thr | Phe | Thr | Ser | Asp | Tyr | Ser | Lys | Gln | Leu | Glu | Glu | Lys |
| 436 | 7010 | 436 | | His | AIB | His | Gly | Thr | Phe | Thr | Ser | Asp | Tyr | Ser | Lys | Gln | Leu | Glu | Glu | Lys |
| 437 | 7011 | 437 | | His | AIB | His | Gly | Thr | Phe | Thr | Ser | Asp | Tyr | Ser | Lys | Gln | Leu | Glu | Glu | Lys |
| 438 | 7012 | 438 | | His | AIB | His | Gly | Thr | Phe | Thr | Ser | Asp | Tyr | Ser | Lys | Gln | Leu | Glu | Glu | Lys |
| 439 | 7013 | 439 | | His | AIB | His | Gly | Thr | Phe | Thr | Ser | Asp | Tyr | Ser | Lys | Gln | Leu | Glu | Glu | Lys |
| 440 | 7014 | 440 | | His | AIB | His | Gly | Thr | Phe | Thr | Ser | Asp | Tyr | Ser | Lys | Gln | Leu | Glu | Glu | Lys |
| 441 | 7016 | 441 | | His | AIB | His | Gly | Thr | Phe | Thr | Ser | Asp | Tyr | Ser | Lys | Gln | Leu | Glu | Glu | Lys |
| 442 | 7017 | 442 | | His | AIB | His | Gly | Thr | Phe | Thr | Ser | Asp | Tyr | Ser | Lys | Gln | Leu | Glu | Glu | Lys |
| 443 | 7018 | 443 | | His | AIB | His | Gly | Thr | Phe | Thr | Ser | Asp | Tyr | Ser | Lys | Gln | Leu | Glu | Glu | Lys |
| 444 | 7019 | 444 | | His | AIB | His | Gly | Thr | Phe | Thr | Ser | Asp | Tyr | Ser | Lys | Gln | Leu | Glu | Glu | Lys |
| 445 | 7020 | 445 | | His | AIB | His | Gly | Thr | Phe | Thr | Ser | Asp | Tyr | Ser | Lys | Gln | Leu | Glu | Glu | Lys |
| 446 | 7022 | 446 | dupl 6967 | His | AIB | His | Gly | Thr | Phe | Thr | Ser | Asp | Tyr | Ser | Lys | Gln | Leu | Glu | Glu | Lys |
| 447 | 7023 | 447 | | His | AIB | His | Gly | Thr | Phe | Thr | Ser | Asp | Tyr | Ser | Lys | Gln | Leu | Glu | Glu | Lys |
| 448 | 7024 | 448 | | His | AIB | His | Gly | Thr | Phe | Thr | Ser | Asp | Tyr | Ser | Lys | Gln | Leu | Glu | Glu | Lys |
| 449 | 7025 | 449 | | His | AIB | His | Gly | Thr | Phe | Thr | Ser | Asp | Tyr | Ser | Lys | Gln | Leu | Glu | Glu | Lys |
| 450 | 7026 | 450 | | His | AIB | His | Gly | Thr | Phe | Thr | Ser | Asp | Tyr | Ser | Lys | Gln | Leu | Glu | Glu | Lys |
| 451 | 7030 | 451 | dupl 7032 | His | AIB | His | Gly | Thr | Phe | Thr | Ser | Asp | Val | Ser | Lys | Gln | Leu | Glu | Glu | Lys |
| 452 | 7031 | 452 | | His | AIB | His | Gly | Thr | Phe | Thr | Ser | Asp | Leu | Ser | Lys | Gln | Leu | Glu | Glu | Lys |
| 453 | 7032 | 453 | dupl 7030 | His | AIB | His | Gly | Thr | Phe | Thr | Ser | Asp | Val | Ser | Lys | Gln | Leu | Glu | Glu | Lys |
| 454 | 7033 | 454 | dupl 7073 | His | AIB | His | Gly | Thr | Phe | Thr | Ser | Asp | Val | Ser | Lys | Gln | Leu | Glu | Glu | Lys |
| 455 | 7034 | 455 | dupl 6818 | His | AIB | His | Gly | Thr | Phe | Thr | Ser | Asp | Tyr | Ser | Lys | Gln | Leu | Glu | Glu | Lys |
| 456 | 7036 | 456 | | His | AIB | His | Gly | Thr | Phe | Thr | Ser | Asp | Leu | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | Lys | Pro | Pro | Gly | | Lys | Lys | | |
| Ala | Val | Arg | Glu | Phe | Ile | Glu | Trp | Leu | Lys | Ala | Gly | Gly | Pro | Ser | Ser | Gly | Lys | Arg | Pro | Pro | Gly | | Lys | Lys | | |
| Ala | Val | Arg | Glu | Phe | Ile | Glu | Trp | Leu | Lys | Ala | Gly | Gly | Pro | Ser | Ser | Gly | Lys | Lys | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | Arg | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Arg | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | Glu | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Glu | | Pro | Pro | Pro | Gly | Lys | Lys | | |
| Ala | Val | Arg | Glu | Phe | Ile | Glu | Trp | Leu | Lys | Asn | Ala | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | His | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Asn | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Glu | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | His | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Asn | | Pro | Pro | Pro | Gly | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 433 | 1 | 12 | 3 | 1.9 | | |
| 18 | 434 | 3 | 15 | 6 | 1.9 | | |
| 18 | 435 | 2 | 15 | 6 | 2.1 | 1 | 48 |
| 18 | 436 | 5 | 16 | 5 | 2.5 | 1 | 90 |
| 18 | 437 | 1 | 10 | 2 | 2.6 | | |
| 18 | 438 | 1 | 10 | 2 | 2.4 | | |
| 18 | 439 | 1 | 13 | 2 | 4.5 | | |
| 18 | 440 | 2 | 16 | 3 | 2.1 | 1 | 91 |
| 18 | 441 | 1 | 13 | 2 | 2.5 | 1 | 68 |
| 18 | 442 | 1 | 11 | 2 | 2.5 | | |
| 18 | 443 | 1 | 13 | 2 | 3 | 1 | 92 |
| 18 | 444 | 1 | 12 | 2 | 4.9 | | |
| 18 | 445 | 1 | 8 | 2 | 2.5 | | |
| 18 | 446 | 3 | 13 | 5 | 2 | 1 | 106 |
| 18 | 447 | 1 | 12 | 2 | 2.3 | | |
| 18 | 448 | 1 | 9 | 2 | 3.1 | | |
| 18 | 449 | 2 | 13 | 3 | 2.7 | 1 | 100 |
| 18 | 450 | 1 | 13 | 2 | 2.9 | | |
| 18 | 451 | 3 | 19 | 6 | 2.9 | 2 | 115 |
| 18 | 452 | 4 | 19 | 2 | 2.9 | 1 | 62 |
| 18 | 453 | 3 | 19 | 7 | 3.2 | | |
| 18 | 454 | 7 | 21 | 6 | 2.5 | 3 | 101 |
| 18 | 455 | 5 | 19 | 6 | 2 | | |
| 18 | 456 | 2 | 17 | 2 | 3.7 | 1 | 100 |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 457 | 7037 | 457 | | His | AIB | His | Gly | Thr | Phe | Thr | Ser | Asp | Leu | Ser | Lys | Gln | Leu | Glu | Glu | Lys |
| 458 | 7038 | 458 | | His | AIB | His | Gly | Thr | Phe | Thr | Ser | Asp | Leu | Ser | Lys | Gln | Leu | Glu | Glu | Lys |
| 459 | 7039 | 459 | | His | AIB | His | Gly | Thr | Phe | Thr | Ser | Asp | Leu | Ser | Lys | Gln | Leu | Glu | Glu | Lys |
| 460 | 7040 | 460 | | His | AIB | His | Gly | Thr | Phe | Thr | Ser | Asp | Leu | Ser | Lys | Gln | Leu | Glu | Glu | Lys |
| 461 | 7041 | 461 | | His | AIB | His | Gly | Thr | Phe | Thr | Ser | Asp | Leu | Ser | Lys | Gln | Leu | Glu | Glu | Lys |
| 462 | 7042 | 462 | | His | AIB | His | Gly | Thr | Phe | Thr | Ser | Asp | Leu | Ser | Lys | Gln | Leu | Glu | Glu | Lys |
| 463 | 7043 | 463 | | His | AIB | His | Gly | Thr | Phe | Thr | Ser | Asp | Val | Ser | Lys | Gln | Leu | Glu | Glu | Lys |
| 464 | 7044 | 464 | | His | AIB | His | Gly | Thr | Phe | Thr | Ser | Asp | Val | Ser | Lys | Gln | Leu | Glu | Glu | Lys |
| 465 | 7045 | 465 | | His | AIB | His | Gly | Thr | Phe | Thr | Ser | Asp | Leu | Ser | Lys | Gln | Leu | Glu | Glu | Lys |
| 466 | 7046 | 466 | | His | AIB | His | Gly | Thr | Phe | Thr | Ser | Asp | Leu | Ser | Lys | Gln | Leu | Glu | Glu | Lys |
| 467 | 7047 | 467 | | His | AIB | His | Gly | Thr | Phe | Thr | Ser | Asp | Leu | Ser | Lys | Gln | Leu | Glu | Glu | Lys |
| 468 | 7048 | 468 | | His | AIB | His | Gly | Thr | Phe | Thr | Ser | Asp | Leu | Ser | Lys | Gln | Leu | Glu | Glu | Lys |
| 469 | 7049 | 469 | | His | AIB | His | Gly | Thr | Phe | Thr | Ser | Asp | Leu | Ser | Lys | Gln | Leu | Glu | Glu | Lys |
| 470 | 7050 | 470 | | His | AIB | His | Gly | Thr | Phe | Thr | Ser | Asp | Tyr | Ser | Lys | Gln | Leu | Glu | Glu | Lys |
| 471 | 7051 | 471 | | His | AIB | His | Gly | Thr | Phe | Thr | Ser | Asp | Val | Ser | Lys | Gln | Leu | Glu | Glu | Lys |
| 472 | 7052 | 472 | | His | AIB | His | Gly | Thr | Phe | Thr | Ser | Asp | Val | Ser | Lys | Gln | Leu | Glu | Glu | Lys |
| 473 | 7053 | 473 | | His | AIB | His | Gly | Thr | Phe | Thr | Ser | Asp | Val | Ser | Lys | Gln | Leu | Glu | Glu | Lys |
| 474 | 7054 | 474 | | His | AIB | His | Gly | Thr | Phe | Thr | Ser | Asp | Val | Ser | Lys | Gln | Leu | Glu | Glu | Lys |
| 475 | 7055 | 475 | | His | AIB | His | Gly | Thr | Phe | Thr | Ser | Asp | Val | Ser | Lys | Gln | Leu | Glu | Glu | Lys |
| 476 | 7056 | 476 | | His | AIB | His | Gly | Thr | Phe | Thr | Ser | Asp | Val | Ser | Lys | Gln | Leu | Glu | Glu | Lys |
| 477 | 7057 | 477 | | His | AIB | His | Gly | Thr | Phe | Thr | Ser | Asp | Val | Ser | Lys | Gln | Leu | Glu | Glu | Lys |
| 478 | 7062 | 478 | | His | AIB | His | Gly | Thr | Phe | Thr | Ser | Asp | Val | Ser | Lys | Gln | Leu | Glu | Glu | Lys |
| 479 | 7063 | 479 | | His | AIB | His | Gly | Thr | Phe | Thr | Ser | Asp | Tyr | Ser | Lys | Gln | Leu | Glu | Glu | Lys |
| 480 | 7064 | 480 | | His | AIB | His | Gly | Thr | Phe | Thr | Ser | Asp | Leu | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | Arg | Glu | Phe | Ile | Glu | Trp | Leu | Lys | Gln | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | His | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Asn | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Asn | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Glu | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | His | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | His | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | His | Glu | Phe | Ile | Glu | Trp | Leu | Lys | Gln | Gly | Gly | Pro | Ser | Ser | Gly | His | | Pro | Pro | Pro | Gly | Lys | Lys | | |
| Ala | Val | His | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | His | | Pro | Pro | Pro | Gly | Lys | Lys | | |
| Ala | Val | His | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Ala | Val | His | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | His | Glu | Phe | Ile | Glu | Trp | Leu | Lys | Gln | Gly | Gly | Pro | Ser | Ser | Gly | Lys | | Pro | Pro | Pro | Gly | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 457 | 1 | 14 | 3 | 3.2 | | |
| 18 | 458 | 2 | 17 | 2 | 3.6 | 1 | 86 |
| 18 | 459 | 1 | 12 | 2 | 3.6 | | |
| 18 | 460 | 2 | 13 | 2 | 3.3 | | |
| 18 | 461 | 3 | 14 | 2 | 3.6 | 1 | 130 |
| 18 | 462 | 1 | 13 | 2 | 4.2 | | |
| 18 | 463 | 1 | 15 | 2 | 2.9 | | |
| 18 | 464 | 1 | 12 | 2 | 3.5 | | |
| 18 | 465 | 4 | 17 | 4 | 2.2 | 2 | 106 |
| 18 | 466 | 2 | 13 | 2 | 3.9 | | |
| 18 | 467 | 2 | 10 | 2 | 3.6 | | |
| 18 | 468 | 2 | 16 | 2 | 2.9 | | |
| 18 | 469 | 2 | 16 | 2 | 2.9 | | |
| 18 | 470 | 3 | 18 | 2 | 2.3 | 1 | 73 |
| 18 | 471 | 1 | 14 | 2 | 2.5 | | |
| 18 | 472 | 2 | 18 | 3 | 2 | | |
| 18 | 473 | 2 | 16 | 2 | 3 | | |
| 18 | 474 | 1 | 8 | 2 | 3.6 | | |
| 18 | 475 | 1 | 6 | 2 | 2.6 | | |
| 18 | 476 | 1 | 9 | 2 | 3.2 | | |
| 18 | 477 | 1 | 11 | 2 | 2.5 | | |
| 18 | 478 | 2 | 17 | 3 | 2.6 | 1 | 85 |
| 18 | 479 | 1 | 13 | 2 | 2.1 | | |
| 18 | 480 | 1 | 12 | 2 | 2.9 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 481 | 7065 | 481 | | His | AIB | His | Gly | Thr | Phe | Thr | Ser | Asp | Val | Ser | Lys | Gln | Leu | Glu | Glu | Lys |
| 482 | 7066 | 482 | | His | AIB | His | Gly | Thr | Phe | Thr | Ser | Asp | Val | Ser | Lys | Gln | Leu | Glu | Glu | Lys |
| 483 | 7067 | 483 | | His | AIB | His | Gly | Thr | Phe | Thr | Ser | Asp | Tyr | Ser | Lys | Gln | Leu | Glu | Glu | Lys |
| 484 | 7068 | 484 | | His | AIB | His | Gly | Thr | Phe | Thr | Ser | Asp | Val | Ser | Lys | Gln | Leu | Glu | Glu | Lys |
| 485 | 7069 | 485 | | His | AIB | His | Gly | Thr | Phe | Thr | Ser | Asp | Val | Ser | Lys | Gln | Leu | Glu | Glu | Lys |
| 486 | 7070 | 486 | | His | AIB | His | Gly | Thr | Phe | Thr | Ser | Asp | Val | Ser | Lys | Gln | Leu | Glu | Glu | Lys |
| 487 | 7071 | 487 | | His | AIB | His | Gly | Thr | Phe | Thr | Ser | Asp | Val | Ser | Lys | Gln | Leu | Glu | Glu | Lys |
| 488 | 7072 | 488 | | His | AIB | His | Gly | Thr | Phe | Thr | Ser | Asp | Val | Ser | Lys | Gln | Leu | Glu | Glu | Lys |
| 489 | 7073 | 489 | dupl 7033 | His | AIB | His | Gly | Thr | Phe | Thr | Ser | Asp | Val | Ser | Lys | Gln | Leu | Glu | Glu | Lys |
| 490 | 7074 | 490 | dupl 6816 | His | AIB | His | Gly | Thr | Phe | Thr | Ser | Asp | Tyr | Ser | Lys | Gln | Leu | Glu | Glu | Lys |
| 491 | 7075 | 491 | | Tyr | AIB | His | Gly | Thr | Phe | Thr | Ser | Asp | Val | Ser | Lys | Gln | Leu | Glu | Glu | Lys |
| 492 | 7076 | 492 | | Phe | AIB | His | Gly | Thr | Phe | Thr | Ser | Asp | Val | Ser | Lys | Gln | Leu | Glu | Glu | Lys |
| 493 | 7077 | 493 | | Tyr | AIB | Glu | Gly | Thr | Phe | Thr | Ser | Asp | Val | Ser | Lys | Gln | Leu | Glu | Glu | Lys |
| 494 | 7078 | 494 | | Tyr | AIB | His | Gly | Thr | Phe | Thr | Ser | Asp | Tyr | Ser | Lys | Gln | Leu | Glu | Glu | Lys |
| 495 | 7079 | 495 | | Phe | AIB | His | Gly | Thr | Phe | Thr | Ser | Asp | Tyr | Ser | Lys | Gln | Leu | Glu | Glu | Lys |
| 496 | 7080 | 496 | | Tyr | AIB | Glu | Gly | Thr | Phe | Thr | Ser | Asp | Tyr | Ser | Lys | Gln | Leu | Glu | Glu | Lys |
| 497 | 7092 | 497 | | His | AIB | His | Gly | Thr | Phe | Thr | Ser | Asp | Tyr | Ser | Lys | Gln | Leu | Glu | Glu | Lys |
| 498 | 7093 | 498 | | Tyr | AIB | His | Gly | Thr | Phe | Thr | Ser | Asp | Tyr | Ser | Lys | Gln | Leu | Glu | Glu | Lys |
| 499 | 7094 | 499 | | Phe | AIB | His | Gly | Thr | Phe | Thr | Ser | Asp | Tyr | Ser | Lys | Gln | Leu | Glu | Glu | Lys |
| 500 | 7095 | 500 | | Tyr | AIB | Glu | Gly | Thr | Phe | Thr | Ser | Asp | Tyr | Ser | Lys | Gln | Leu | Glu | Glu | Lys |
| 501 | 7096 | 501 | | Phe | AIB | Glu | Gly | Thr | Phe | Thr | Ser | Asp | Tyr | Ser | Lys | Gln | Leu | Glu | Glu | Lys |
| 502 | 7097 | 502 | | Phe | AIB | Glu | Gly | Thr | Phe | Thr | Ser | Asp | Val | Ser | Lys | Gln | Leu | Glu | Glu | Lys |
| 503 | 7098 | 503 | | Phe | AIB | Glu | Gly | Thr | Phe | Thr | Ser | Asp | Leu | Ser | Lys | Gln | Leu | Glu | Glu | Lys |
| 504 | 7099 | 504 | | Phe | AIB | Glu | Gly | Thr | Phe | Thr | Ser | Asp | Tyr | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Arg | Val | Arg | Glu | Phe | Ile | Glu | Trp | Leu | Lys | Ala | Gly | Gly | Pro | Ser | Ser | Gly | Gln | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | Lys | Pro | Pro | Gly | | Lys | Lys | | |
| Ala | Val | Arg | Glu | Phe | Ile | Glu | Trp | Leu | Lys | Gln | Gly | Gly | Pro | Ser | Ser | Gly | Lys | Lys | Pro | Pro | Gly | | Lys | Lys | | |
| Ala | Val | Arg | Glu | Phe | Ile | Glu | Trp | Leu | Lys | Ala | Gly | Gly | Pro | Ser | Ser | Gly | Lys | Lys | Pro | Pro | Gly | | Lys | Lys | | |
| Ala | Val | Arg | Glu | Phe | Ile | Glu | Trp | Leu | Lys | Ala | Gly | Gly | Pro | Ser | Ser | Gly | Lys | Lys | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | Lys | Pro | Pro | Gly | | Lys | Lys | | |
| Arg | Val | Arg | Glu | Phe | Ile | Glu | Trp | Leu | Lys | Ala | Gly | Gly | Pro | Ser | Ser | Gly | Lys | Lys | Pro | Pro | Gly | | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 481 | 2 | 18 | 4 | 2 | 1 | 80 |
| 18 | 482 | 4 | 18 | 5 | 2.9 | 1 | 88 |
| 18 | 483 | 1 | 6 | 2 | 4 | | |
| 18 | 484 | 1 | 11 | 2 | 4.2 | | |
| 18 | 485 | 2 | 13 | 2 | 4.3 | 1 | 87 |
| 18 | 486 | 3 | 17 | 7 | 4.4 | | |
| 18 | 487 | 1 | 13 | 2 | 3.9 | | |
| 18 | 488 | 1 | 14 | 2 | 4.9 | | |
| 18 | 489 | 2 | 24 | 4 | 1.8 | | |
| 18 | 490 | 2 | 18 | 2 | 2.2 | | |
| 18 | 491 | 1 | 3 | 2 | 6.9 | | |
| 18 | 492 | 1 | 4 | 2 | 3.9 | | |
| 18 | 493 | 7 | 16 | 6 | 5.1 | 3 | 112 |
| 18 | 494 | | | 2 | 39.3 | | |
| 18 | 495 | | | 2 | 13.6 | | |
| 18 | 496 | | | 3 | 9.2 | | |
| 18 | 497 | 3 | 14 | 5 | 1.6 | 1 | 97 |
| 18 | 498 | | | 2 | 60.5 | | |
| 18 | 499 | | | 2 | 25.1 | | |
| 18 | 500 | 1 | 4 | 2 | 52.2 | | |
| 18 | 501 | 1 | 9 | 4 | 14.4 | | |
| 18 | 502 | 7 | 15 | 9 | 5.7 | 6 | 125 |
| 18 | 503 | 1 | 10 | 2 | 22.8 | | |
| 18 | 504 | 1 | 6 | 2 | 12.2 | | |

Figure 1 (Continued)

| Ex | G ref | SEQ ID | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|---|---|
| | | | | | | | | | | | | | | | | | | | | |
| 505 | 7100 | 505 | | Phe | AIB | Glu | Gly | Thr | Phe | Thr | Ser | Asp | Val | Ser | Lys | Gln | Leu | Glu | Glu | Lys |
| 506 | 7101 | 506 | | Phe | AIB | Glu | Gly | Thr | Phe | Thr | Ser | Asp | Leu | Ser | Lys | Gln | Leu | Glu | Glu | Lys |
| 507 | 7102 | 507 | | His | AIB | Glu | Gly | Thr | Phe | Thr | Ser | Asp | Tyr | Ser | Lys | Gln | Leu | Glu | Glu | Lys |
| 508 | 7103 | 508 | | His | AIB | Glu | Gly | Thr | Phe | Thr | Ser | Asp | Tyr | Ser | Lys | Gln | Leu | Glu | Glu | Lys |
| 509 | 7104 | 509 | | His | AIB | Glu | Gly | Thr | Phe | Thr | Ser | Asp | Val | Ser | Lys | Gln | Leu | Glu | Glu | Lys |
| 510 | 7105 | 510 | | His | AIB | Glu | Gly | Thr | Phe | Thr | Ser | Asp | Tyr | Ser | Lys | Gln | Leu | Glu | Glu | Lys |
| 511 | 7107 | 511 | | His | AIB | Glu | Gly | Thr | Phe | Thr | Ser | Asp | Leu | Ser | Lys | Gln | Leu | Glu | Glu | Lys |
| 512 | 7122 | 512 | | Phe | AIB | Gln | Gly | Thr | Phe | Thr | Ser | Asp | Val | Ser | Lys | Gln | Leu | Glu | Glu | Lys |
| 513 | 7123 | 513 | | Phe | AIB | Gln | Gly | Thr | Phe | Thr | Ser | Asp | Val | Ser | Lys | Gln | Leu | Glu | Glu | Lys |
| 514 | 7124 | 514 | | His | AIB | Gln | Gly | Thr | Phe | Thr | Ser | Asp | Val | Ser | Lys | Gln | Leu | Glu | Glu | Lys |
| 515 | 7125 | 515 | | His | AIB | Glu | Gly | Thr | Phe | Thr | Ser | Asp | Val | Ser | Lys | Gln | Leu | Glu | Glu | Lys |
| 516 | 7130 | 516 | | Tyr | AIB | Glu | Gly | Thr | Phe | Thr | Ser | Asp | Val | Ser | Lys | Gln | Leu | Glu | Glu | Lys |
| 517 | 7131 | 517 | | Tyr | AIB | Glu | Gly | Thr | Phe | Thr | Ser | Asp | Val | Ser | Lys | Gln | Leu | Glu | Glu | Lys |
| 518 | 7134 | 518 | | Tyr | AIB | Gln | Gly | Thr | Phe | Thr | Ser | Asp | Val | Ser | Lys | Gln | Leu | Glu | Glu | Lys |
| 519 | 7135 | 519 | | His | AIB | Gln | Gly | Thr | Phe | Thr | Ser | Asp | Val | Ser | Lys | Gln | Leu | Glu | Glu | Lys |
| 520 | 7136 | 520 | | His | AIB | Gln | Gly | Thr | Phe | Thr | Ser | Asp | Val | Ser | Lys | Gln | Leu | Glu | Glu | Lys |
| 521 | 7137 | 521 | | His | AIB | Gln | Gly | Thr | Phe | Thr | Ser | Asp | Val | Ser | Lys | Gln | Leu | Glu | Glu | Lys |
| 522 | 7138 | 522 | | His | AIB | Gln | Gly | Thr | Phe | Thr | Ser | Asp | Val | Ser | Lys | Gln | Leu | Glu | Glu | Lys |
| 523 | 7145 | 523 | | Phe | AIB | Glu | Gly | Thr | Phe | Thr | Ser | Asp | Val | Ser | Lys | Gln | Leu | Glu | Glu | Lys |
| 524 | 7146 | 524 | | Phe | AIB | Glu | Gly | Thr | Phe | Thr | Ser | Asp | Val | Ser | Lys | Gln | Leu | Glu | Glu | Lys |
| 525 | 7147 | 525 | | Phe | AIB | Glu | Gly | Thr | Phe | Thr | Ser | Asp | Val | Ser | Lys | Gln | Leu | Glu | Glu | Lys |
| 526 | 7148 | 526 | | Phe | AIB | Glu | Gly | Thr | Phe | Thr | Ser | Asp | Val | Ser | Lys | Gln | Leu | Glu | Glu | Lys |
| 527 | 7150 | 527 | | Phe | AIB | Glu | Gly | Thr | Phe | Thr | Ser | Asp | Val | Ser | Lys | Gln | Leu | Glu | Glu | Lys |

Figure 1 (Continued)

| 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 | 43 | 44 |
|---|---|---|---|---|---|---|---|---|---|---|---|---|---|---|---|---|---|---|---|---|---|---|---|---|---|---|
| | | | | | | | | | | | | | | | | | | | | | | | | | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Ala | Val | Arg | Glu | Phe | Ile | Glu | Trp | Leu | Lys | Ala | Gly | Gly | Pro | Ser | Ser | Gly | Lys | Lys | Pro | Pro | Pro | Gly | Lys | Lys | | |
| Ala | Val | Arg | Glu | Phe | Ile | Glu | Trp | Leu | Lys | Gln | Gly | Gly | Pro | Ser | Ser | Gly | Lys | Lys | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | Lys | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Ala | Gly | Gly | Pro | Ser | Ser | Gly | Lys | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Glu | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Gln | | Pro | Pro | Pro | Gly | Lys | Lys | | |
| Arg | Val | Arg | Glu | Phe | Ile | Glu | Trp | Leu | Lys | Gln | Gly | Gly | Pro | Ser | Ser | Gly | Lys | | Pro | Pro | Pro | Gly | Lys | Lys | | |

Figure 1 (Continued)

| n (R = Cn) | Ex | Feeding study scores | | Receptor binding results | | Half life | |
|---|---|---|---|---|---|---|---|
| | | n | potency | n | human GLP1R cAMP CHO cells | n | t1/2 (h) |
| 18 | 505 | 1 | 13 | 2 | 6 | 1 | 88 |
| 18 | 506 | 6 | 14 | 4 | 8.5 | 3 | 102 |
| 18 | 507 | 6 | 15 | 4 | 2.1 | 5 | 118 |
| 18 | 508 | 2 | 17 | 2 | 2.5 | 1 | 107 |
| 18 | 509 | 4 | 18 | 3 | 2.4 | 1 | 62 |
| 18 | 510 | 3 | 16 | 4 | 2.5 | 2 | 110 |
| 18 | 511 | 3 | 19 | 4 | 1.6 | 2 | 111 |
| 18 | 512 | 2 | 22 | 4 | 6.1 | 1 | 88 |
| 18 | 513 | 1 | 7 | 2 | 10 | | |
| 18 | 514 | 6 | 20 | 7 | 6.6 | 6 | 121 |
| 18 | 515 | 2 | 15 | 2 | 2.1 | | |
| 18 | 516 | 3 | 17 | 4 | 4.6 | | |
| 18 | 517 | 3 | 16 | 5 | 6.3 | 2 | 134 |
| 18 | 518 | 1 | 14 | 2 | 4.3 | | |
| 18 | 519 | 3 | 19 | 2 | 5 | 1 | 94 |
| 18 | 520 | 2 | 19 | 2 | 6.7 | 1 | 63 |
| 18 | 521 | 1 | 18 | 2 | 12.7 | | |
| 18 | 522 | 1 | 15 | 2 | 10 | | |
| 18 | 523 | 3 | 18 | 7 | 3.3 | 1 | 97 |
| 18 | 524 | 2 | 16 | 2 | 4.3 | 1 | 98 |
| 18 | 525 | 2 | 14 | 2 | 4.7 | | |
| 18 | 526 | 2 | 12 | 2 | 5.5 | | |
| 18 | 527 | | | | | | |

COMPOUNDS

CROSS-REFERENCE TO RELATED APPLICATIONS

The present application is a continuation of U.S. patent application Ser. No. 18/266,571, filed Jun. 9, 2023, which is a U.S. National Stage Entry of International Application No. PCT/GB2021/053249, filed Dec. 10, 2021, which claims the benefit of and priority to Great Britain Patent Application No. 2019588.9, filed on Dec. 11, 2020, and Great Britain Patent Application No. 2110809.7, filed on Jul. 27, 2021, the contents of each of which are incorporated herein by reference in their entireties.

REFERENCE TO THE ELECTRONIC SEQUENCE FILE

The contents of the electronic sequence listing (METS_019_03US_SeqList_ST26.xml; Size: 1,130,227 bytes; and Date of Creation: Aug. 21, 2025) are herein incorporated by reference in its entirety.

FIELD OF THE INVENTION

The present disclosure relates to compounds which are peptide hormone analogues, and which are useful in treating disorders such as diabetes and obesity.

BACKGROUND

According to the National Health and Nutrition Examination Survey (NHANES, 2009-2010), 33.0% of adults in the United States aged 20 and over are overweight, 35.7% are obese, and 6.3% are extremely obese. In addition, a large percentage of children in the United States are overweight or obese.

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type-2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., *N. Engl. J. Med.* 347:305, 2002; Massie, *N. Engl. J. Med.* 347:358, 2002).

Diabetes is a chronic syndrome of impaired carbohydrate, protein, and fat metabolism owing to insufficient secretion of insulin or to target tissue insulin resistance. It occurs in two major forms: insulin-dependent diabetes mellitus (type 1 diabetes) and non-insulin dependent diabetes mellitus (type 2 diabetes). Diabetes type 1, or insulin dependent diabetes mellitus (IDDM) is caused by the destruction of R cells, which results in insufficient levels of endogenous insulin. Diabetes type 2, or non-insulin dependent diabetes, results from a defect in both the body's sensitivity to insulin, and a relative deficiency in insulin production. According to the National Diabetes Statistics Report, 2014 around 28.9 million adults in the United States aged 20 and over have diabetes (2009-2012 National Health and Nutrition Examination Survey estimates applied to 2012 U.S. Census data). In adults 90 to 95% of the diabetes is type 2 diabetes.

There is substantial evidence that weight loss in obese persons reduces important disease risk factors. Even a small weight loss, such as 10% of the initial body weight in both overweight and obese adults has been associated with a decrease in risk factors such as hypertension, hyperlipidemia, and hyperglycemia. It has been shown that considerable weight loss can effectively cure type 2 diabetes (Lim et al., *Diabetologia* June 2011).

Although diet and exercise provide a simple process to decrease weight gain, overweight and obese individuals often cannot sufficiently control these factors to effectively lose weight. Pharmacotherapy is available; several weight loss drugs have been approved by the Food and Drug Administration that can be used as part of a comprehensive weight loss program. However, many of these drugs have serious adverse side effects. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients. It is not only obese subjects who wish to lose weight. People with weight within the recommended range, for example, in the upper part of the recommended range, may wish to reduce their weight, to bring it closer to the ideal weight. Thus, a need remains for agents that can be used to effect weight loss in overweight and obese subjects as well as in subjects who are of normal weight.

A number of approaches to the development of agents useful in effecting weight loss have involved gastrointestinal peptide hormones and their analogues. For example, derivatives of peptides deriving from the preproglucagon molecule have been proposed for use in treatment of obesity and/or diabetes. Preproglucagon is a precursor peptide of glucagon-like peptide 1 (GLP-1), as well as other hormones including glucagon GLP-1 is produced in vivo in the intestinal L cell in response to the presence of nutrients in the lumen of the gut. GLP-1 possesses a number of physiological functions including increasing insulin secretion from the pancreas in a glucose-dependent manner, decreasing glucagon secretion from the pancreas, inhibiting gastric emptying and decreasing food intake by increasing satiety. Increased insulin secretion leads to a decrease in circulating glucose concentration.

Examples of research into analogues of such peptides are described in, for example, WO2013/004983 which describes peptide molecules containing sequence from both the GLP-1 and glucagon peptides. WO2015/132599 also discloses peptide hormone analogues, which are derivable from preproglucagon and which are useful in the therapy of disorders such as obesity and diabetes. WO2017/178829 discloses compounds that are analogues of exendin-4, GLP-1 and oxyntomodulin which have a modified ligand bias and therapeutically useful characteristics. Another example is the peptide liraglutide, a GLP-1 agonist which has the sequence of GLP-1(7-37) with an arginine residue substituted for the native lysine at position 34, and with the sidechain of the lysine residue at position 26 being acylated by a hexadecanoyl group (palmitic acid) attached to the lysine though a glutamic acid spacer. Liraglutide has been developed for use as a once daily injectable drug for the treatment of type II diabetes. The same active ingredient as in liraglutide is marketed as Saxenda for the treatment of obesity (once daily injection). Semaglutide, a once weekly injectable analogue of GLP-1, has two amino acid substitutions compared to human GLP-1 (AIB8, Arg34) and is derivatized at lysine 26 with a linker and a C18 diacid fatty acid.

However, despite significant advances, the process of identifying substances useful as drugs remains a complex and, in many cases, unpredictable field. In order to be useful as therapeutic agents, compounds must possess a suitable range of properties. In addition to having good efficacy at the biological target of interest, compounds must have good in vivo pharmacokinetic properties, low toxicity and an acceptable side effect profile. For example, even with commercial agents such as liraglutide, side effects can include nausea and vomiting, and concerns have also been raised with regard to thyroid cancer and pancreatitis.

Thus, there remains a need for further compounds which are useful for the treatment of disorders and diseases such as diabetes and obesity. For example, it would be desirable to identify peptides having beneficial properties such as an improved activity profile, and/or which have reduced side effects. For example, it would be desirable for a peptide to be identified that reduces appetite and/or reduces food intake. Alternatively, or additionally, it would be desirable for a peptide to be identified that has these and other biological effects (for example the therapeutically useful biological effects described herein) for a sustained period. A compound that has a longer period of activity can be administered less frequently and at lower dose, which contributes to improved convenience for the subject, to fewer side effects and to lower cost.

SUMMARY OF THE INVENTION

In a first aspect there is provided a compound of Formula (I):

Xaa1-AIB2-Xaa3-Gly4-Thr5-Phe6-Thr7-Ser8-Asp9-Xaa10-Ser11-Lys12-Gln13-Leu14-Glu15-Glu16-Xaa17-Xaa18-Val19-Xaa20-Xaa21-Phe22-Ile23-Glu24-Trp25-Leu26-Lys27-Xaa28-Xaa29-Gly30-Pro31-Ser32-Xaa33-Gly34-Xaa35-Xaa36-Pro37-Pro38-Xaa39-Xaa40-Xaa41-Lys42 (I) [SEQ ID NO: 528]

wherein:

Xaa1 is His, Tyr or Phe;
Xaa3 is His, Gln or Glu;
Xaa10 is Leu, Tyr or Val;
Xaa17 is Glu or Lys;
Xaa18 is Ala or Arg;
Xaa20 is Arg, Gln, Lys or His;
Xaa21 is Leu, Ala, Arg, Lys or Glu;
Xaa28 is Ala, Asn, Gln or His;
Xaa29 is Gly or Ala;
Xaa33 is Ser, His or Gln;
Xaa35 is Lys, Pro, His, Arg, Asn, Gln, Glu, Ser or Ala;
Xaa36 is Phe, His, Gln, Glu, Lys, Ser, Arg or absent
Xaa39 is Pro or Gly;
Xaa40 is Gly or absent;
Xaa41 is Lys or absent;

and the lysine residue at position 42 is substituted at its F-amino group with a group Y and Y is:

Z-Xaa43-Xaa44- wherein:

Xaa43 is Asn or absent;
Xaa44 is His or absent;

and Z is a group of formula:

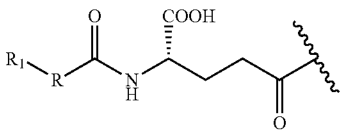

wherein R is a $C_{16}$-$C_{18}$ alkylene or alkenylene group; and $R^1$ is $CO_2H$;

or a derivative of the compound; or a salt or solvate of the compound or the derivative.

Also provided herein is a composition comprising a compound, derivative, salt or solvate of the invention together with a pharmaceutically acceptable carrier and optionally a further therapeutic agent.

Also provided herein is a compound, derivative, salt or solvate of the invention, or a composition comprising such a compound, derivative, salt or solvate and a pharmaceutically acceptable carrier, for use as a medicament, e.g. for use in the prevention or treatment of diabetes, obesity, heart disease, stroke or non-alcoholic fatty liver disease, improving insulin release in a subject, improving carbohydrate metabolism in a subject, improving the lipid profile of a subject, reducing appetite, reducing food intake, reducing calorie intake, improving carbohydrate tolerance in a subject, and/or for use as a cytoprotective agent, for example in the prevention or treatment of Parkinsonism, Alzheimer's disease and other types of neural and cellular degeneration.

Also provided herein is a method of treating or preventing a disease or disorder or other non-desired physiological state in a subject comprising administration of a therapeutically effective amount of a compound, derivative, salt or solvate of the invention, or of a composition comprising such a compound, derivative, salt or solvate and a pharmaceutically acceptable carrier, e.g. in a method of treating or preventing diabetes, obesity, heart disease, stroke or non-alcoholic fatty liver disease in a subject, improving insulin release in a subject, improving carbohydrate metabolism in a subject, improving the lipid profile of a subject, improving carbohydrate tolerance in a subject, reducing appetite, reducing food intake, reducing calorie intake, and/or providing cytoprotection in a subject.

Also provided herein is a use of a compound, derivative, salt or solvate of the invention for the manufacture of a medicament for the prevention or treatment of diabetes, obesity, heart disease, stroke or non-alcoholic fatty liver disease, improving insulin release in a subject, improving carbohydrate metabolism in a subject, improving the lipid profile of a subject, improving carbohydrate tolerance in a subject, reducing appetite, reducing food intake, reducing calorie intake, and/or for use as a cytoprotective agent, for example in the prevention or treatment of Parkinsonism, Alzheimer's disease and other types of neural and cellular degeneration.

Also provided herein is a method of causing weight loss or preventing weight gain in a subject for cosmetic purposes comprising administration of an effective amount of a compound, derivative, salt or solvate of the invention.

BRIEF DESCRIPTION OF THE DRAWINGS

FIG. 1 shows the amino acid sequences of example compounds of the invention. The compounds are presented with the N-terminal residue at the left-hand side of the table (signified by the column titled "1"). The amino acid sequence for each compound is set out over two horizontal pages. Results of feeding and receptor binding experiments are shown in the far right hand columns.

SEQUENCES

The amino acid sequences herein are shown with the N-terminus to the left, and where sequences are set out across multiple lines, the N-terminus is to the top left. Unless indicated otherwise, the amino acid residues in the sequences are L-amino acids.

The amino acid sequences listed in the application are shown using standard letter abbreviations for amino acids. The unnatural amino acid 2-aminoisobutyric acid has its usual abbreviation 'AIB'.

The specific sequences given herein relate to specific embodiments of the invention.

DETAILED DESCRIPTION

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects. In preferred embodiments of the invention, the subject is a human subject.

Appetite: A natural desire, or longing for food. In one embodiment, appetite is measured by a survey to assess the desire for food. Increased appetite generally leads to increased feeding behaviour.

Appetite Suppressants: Compounds that decrease the desire for food. Commercially available appetite suppressants include, but are not limited to, amfepramone (diethylpropion), phentermine, mazindol and phenylpropanolamine fenfluramine, dexfenfluramine, and fluoxetine.

Body Mass Index (BMI): A mathematical formula for measuring body mass, also sometimes called Quetelet's Index. BMI is calculated by dividing weight (in kg) by height$^2$ (in metres$^2$). The current standards for both men and women accepted as "normal" are a BMI of 20-24.9 kg/m$^2$. In one embodiment, a BMI of greater than 25 kg/m$^2$ can be used to identify an obese subject. Grade I obesity (which is sometimes referred to as being "overweight" rather than obesity) corresponds to a BMI of 25-29.9 kg/m$^2$. Grade II obesity corresponds to a BMI of 30-40 kg/m$^2$; and Grade III obesity corresponds to a BMI greater than 40 kg/m$^2$ (Jequier, *Am. J Clin. Nutr.* 45:1035-47, 1987). Ideal body weight will vary among species and individuals based on height, body build, bone structure, and sex.

Cardioprotection refers to the protection of cardiac cells (and especially the myocardial cells) from apoptosis, necrotic cell death or degeneration (loss of function). Cardioprotection is most often required following myocardial infarction, but may also be used in subjects suffering from ischemic heart disease (for example angina)

Cytoprotection refers to the protection of cells from apoptosis, necrotic cell death or degeneration (loss of function).

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterized by an inability to deliver insulin in an amount and with the precise timing that is needed for control of glucose homeostasis. Diabetes type I, or insulin dependent diabetes mellitus (IDDM) is caused by the destruction of R cells, which results in insufficient levels of endogenous insulin. Diabetes type II, or non-insulin dependent diabetes, results from a defect in both the body's sensitivity to insulin, and a relative deficiency in insulin production.

Energy Metabolism: The body has to expend a certain amount of energy to maintain normal metabolism. In civilized man this is often set at about 2,800 Calories daily. If food consumption does not provide this, weight loss results. However, energy metabolism is also regulated, and, for example, administration of glucagon is thought to increase the metabolic rate so that a greater food intake is required to achieve energy balance and maintain weight. Thus, if food intake is maintained at the usual level, but energy metabolism is increased, weight loss will result.

Food intake: The amount of food consumed by an individual. Food intake can be measured by volume or by weight. For example, food intake may be the total amount of food consumed by an individual. In a feeding experiment, 'Food Intake' is the weight of a standardised chow consumed by an animal in a 24 hour period. Or food intake may be the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

GLP-1: Glucagon-like peptide 1 (GLP-1) is derived from the transcription product of the proglucagon gene. The biologically active forms of GLP-1 are truncated forms known as GLP-1(7.37) and GLP-$1_{(7-36)}$-$NH_2$ (the designation —$NH_2$ designates an amino acid sequence in which the C-terminal amino acid has a —$C(O)NH_2$ group in place of a carboxylic acid group).

The sequence of human GLP-$1_{(7-37)}$ is His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly. [SEQ ID NO: 529]

The sequence of human GLP-$1_{(7-36)}$-$NH_2$ is His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-$CONH_2$. [SEQ ID NO: 530]

Glucagon: Glucagon is a peptide derived from the proglucagon gene. It is a 29-amino acid polypeptide in humans and has the sequence: His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr. [SEQ ID NO:531]

Neuroprotection refers to the protection of neurons within the nervous system (preferably within the central nervous system) from apoptosis, necrotic cell death or degeneration (loss of function). Neuroprotective treatments, including those relating to various aspects of the present invention may be required following a brain injury (for example those following physical trauma or non-traumatic injury such as stroke, brain tumours, infection, poisoning, hypoxia, ischemia, encephalopathy or substance abuse). Neuroprotective treatments, including those relating to various aspects of the present invention may also be indicated in subjects having a chronic neurodegenerative disease such as Alzheimer's disease, Parkinson's disease, Gehrig's disease or Huntington's disease.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/lb/day (18.2 cal/kg/day). About 30% to about 40% should be protein, about 7% to about 10% should be from carbohydrate, and about 50% to about 62.5% should be derived from fat intake. One of skill in the art can readily identify the normal daily diet of an individual of any species.

Obesity: A condition in which excess body fat may put a person at health risk (see Barlow and Dietz, *Pediatrics* 102:E29, 1998; National Institutes of Health, National Heart, Lung, and Blood Institute (NHLBI), *Obes. Res.* 6 (suppl. 2):51S-209S, 1998). Excess body fat is a result of an imbalance of energy intake and energy expenditure. For example, the Body Mass Index (BMI) may be used to assess obesity. In one commonly used convention, a BMI of 25.0 $kg/m^2$ to 29.9 $kg/m^2$ is overweight, while a BMI of 30 $kg/m^2$ or greater is obese.

In another convention, waist circumference is used to assess obesity. In this convention, in men a waist circumference of 102 cm or more is considered obese, while in women a waist circumference of 89 cm or more is considered obese. Strong evidence shows that obesity affects both the morbidity and mortality of individuals. For example, an obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al., *Am. Fam. Phys.* 63:2185, 2001).

Overweight: An individual who weighs more than their ideal body weight. An overweight individual can be obese but is not necessarily obese. For example, an overweight individual is any individual who desires to decrease their weight. In one convention, an overweight individual is an individual with a BMI of 25.0 $kg/m^2$ to 29.9 $kg/m^2$.

Oxyntomodulin (OXM): Oxyntomodulin is a 37 amino acid peptide member of the glucagon superfamily comprising the entire 29 amino acid sequence of glucagon, with an eight amino acid carboxy terminal extension, resulting from the tissue-specific processing of the pre-pro-glucagon precursor in the brain and gut. The human OXM sequence is as follows:

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala. [SEQ ID NO: 532]

PEGylation and PEGylated: PEGylation refers to the process of reacting a poly(alkylene glycol), preferably an activated poly(alkylene glycol) to form a covalent bond. A facilitator may be used, for example an amino acid, e.g. lysine. Although "PEGylation" is often carried out using poly(ethylene glycol) or derivatives thereof, such as methoxy poly(ethylene glycol), the term is not limited herein to the use of methoxy poly(ethylene glycol) but also includes the use of any other useful poly(alkylene glycol), for example poly(propylene glycol). The term PEGylated refers to a compound containing such a poly(alkylene glycol) group.

pI: pI is an abbreviation for isoelectric point. An alternative abbreviation sometimes used is IEP. It is the pH at which a particular molecule carries no net electric charge. At a pH below its pI a protein or peptide carries a net positive charge. At a pH above its pI a protein or peptide carries a net negative charge. Proteins and peptides can be separated according to their isoelectric points using a technique called isoelectric focusing which is an electrophoretic method that utilises a pH gradient contained within a polyacrylamide gel.

Peripheral administration: Administration outside of the central nervous system. Peripheral administration does not include direct administration to the brain. Peripheral administration includes, but is not limited to intravascular, intramuscular, subcutaneous, inhalation, oral, rectal, transdermal or intra-nasal administration.

Polypeptide: A polymer in which the monomers are amino acid residues which are joined together through amide bonds. Unless dictated otherwise by context, the terms "polypeptide", "peptide", or "protein" as used herein encompass any amino acid sequence and include modified sequences such as glycoproteins. The term "polypeptide" covers naturally occurring proteins, as well as those which are recombinantly or synthetically produced. The term "polypeptide fragment" refers to a portion of a polypeptide, for example a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Subcutaneous administration: Subcutaneous administration is administration of a substance to the subcutaneous layer of fat which is found between the dermis of the skin and the underlying tissue. Subcutaneous administration may be by an injection using a hypodermic needle fitted, for example, to a syringe or a "pen" type injection device. Other administration methods may be used for example microneedles. Injection with a hypodermic needle typically involves a degree of pain on behalf of the recipient. Such pain may be masked by use of a local anaesthetic or analgesic. However, the usual method used to reduce the perceived pain of injections is to merely distract the subject immediately prior to and during the injection. Pain may be minimised by using a relatively small gauge hypodermic needle, by injecting a relatively small volume of substance and by avoiding excessively acidic or alkali compositions which may cause the subject to experience a "stinging" sensation at the injection site. Compositions having a pH of between pH 4 and pH 10 are usually regarded as tolerably comfortable.

Therapeutically effective amount: A dose sufficient to prevent advancement, or to cause regression of a disorder, or which is capable of relieving a sign or symptom of a disorder, or which is capable of achieving a desired result. In some embodiments, a therapeutically effective amount of a compound of the invention is an amount sufficient to inhibit or halt weight gain, or an amount sufficient to decrease appetite.

Compounds of the Invention

The present inventors have found that example compounds of the invention have properties including causing weight loss in vivo. The compounds also have a long half-life in the blood, meaning that they can be administered at a conveniently low frequency. In these respects, the compounds of the invention have an improved profile in comparison to the known compound semaglutide.

Compared with GLP-1 and derivatives of GLP-1 that have gone before, the compounds of the invention are extended at the C-terminus with particular residues, including that there is a lysine residue at position 42 and including that that lysine residue is functionalised in a particular way, to include the group R—$R^1$ where $R^1$ is $CO_2H$. These are functionalisations that have not previously been investigated and the beneficial properties found by the current inventors have not previously been seen.

As described above, compounds of the invention have Formula (I):

Xaa1-AIB2-Xaa3-Gly4-Thr5-Phe6-Thr7-Ser8-Asp9-Xaa10-Ser11-Lys12-Gln13-Leu14-Glu15-Glu16-Xaa17-Xaa18-Val19-Xaa20-Xaa21-Phe22-Ile23-Glu24-Trp25-Leu26-Lys27-Xaa28-Xaa29-Gly30-Pro31-Ser32-Xaa33-Gly34-Xaa35-Xaa36-Pro37-Pro38-Xaa39-Xaa40-Xaa41-Lys42; (I) [SEQ ID NO: 528]

wherein

Xaa1 is His, Tyr or Phe;
Xaa3 is His, Gln or Glu;
Xaa10 is Leu, Tyr or Val;
Xaa17 is Glu or Lys;
Xaa18 is Ala or Arg;
Xaa20 is Arg, Gln, Lys or His;
Xaa21 is Leu, Ala, Arg, Lys or Glu;
Xaa28 is Ala, Asn, Gln or His;
Xaa29 is Gly or Ala;
Xaa33 is Ser, His or Gln;
Xaa35 is Lys, Pro, His, Arg, Asn, Gln, Glu, Ser or Ala;
Xaa36 is Phe, His, Gln, Glu, Lys, Ser, Arg or absent
Xaa39 is Pro or Gly;
Xaa40 is Gly or absent;
Xaa41 is Lys or absent;

and the lysine residue at position 42 is substituted at its ε-amino group with a group Y and Y is:

Z-Xaa43-Xaa44- wherein:

Xaa43 is Asn or absent;
Xaa44 is His or absent;

and Z is a group of formula:

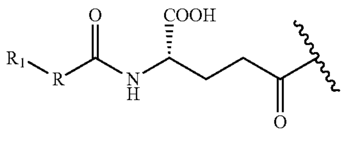

wherein R is a $C_{16}$-$C_{18}$ alkylene or alkenylene group; and $R^1$ is $CO_2H$.

Within the first portion of the molecule (Xaa1-Lys42), it is preferred that:

Xaa17 is Lys;
Xaa18 is Ala or Arg;
Xaa20 is Arg or His;
Xaa21 is Leu or Glu;
Xaa28 is Ala, Gln or His;
Xaa29 is Gly;
Xaa33 is Ser
Xaa35 is Lys, Glu, His, Gln or Asn;
Xaa36 is absent;
Xaa39 is Pro; and
Xaa41 is Lys.

In a more preferred embodiment, in the first portion of the molecule (Xaa1-Lys42):

Xaa1 is His or Phe;
Xaa3 is His or Glu;
Xaa10 is Tyr or Val;
Xaa17 is Lys;
Xaa18 is Ala or Arg;
Xaa20 is Arg or His;
Xaa21 is Glu;
Xaa28 is Ala or Gln;
Xaa29 is Gly;
Xaa33 is Ser
Xaa35 is Lys;
Xaa36 is absent;
Xaa39 is Pro;
Xaa40 is Gly; and
Xaa41 is Lys.

Considering the residues in turn, Xaa1 is selected from His, Tyr and Phe. For example, Xaa1 is selected from His and Tyr, or alternatively Xaa1 is selected from His and Phe. For example, Xaa1 is His. Alternatively, Xaa1 is Phe. In an especially preferred embodiment, Xaa1 is Phe. It has been found that compounds of the invention with Phe at the N-terminus (in particular ones that also have Xaa3=Glu) have a GLP-1 receptor bias. Compounds with Phe at the N-terminus have been seen to fully activate the intracellular cAMP system, in a manner similar to native GLP1, whilst being weaker than GLP1 at activating the intracellular beta arrestin messenger system, so there is a bias at the GLP1 receptor. In some circumstances, this GLP1 receptor bias is an advantage in prolonging the action at the GLP1 receptor and producing relative enhancement of the action on the beta cell in releasing insulin while not enhancing other dose limiting effects such as inhibition of food intake and food aversion.

Xaa3 is selected from His, Gln and Glu. Preferably, Xaa3 is selected from His and Glu. For example, Xaa3 is His. Alternatively, Xaa3 is Glu. In an especially preferred embodiment, Xaa3 is Glu.

Xaa10 is selected from Leu, Tyr and Val. Preferably, Xaa10 is Tyr or Val, for example Xaa10 is Tyr. Alternatively, Xaa10 is Val.

Xaa17 is selected from Glu or Lys. Preferably, Xaa17 is Lys.

Xaa18 is selected from Ala or Arg. For example, Xaa18 is Ala. Alternatively, Xaa18 is Arg. In an especially preferred embodiment, Xaa18 is Arg.

Xaa20 is selected from Arg, Gln, Lys and His. Preferably, Xaa20 is Arg or His, for example Xaa20 is Arg. Alternatively, Xaa20 is His. In an especially preferred embodiment, Xaa20 is Arg.

Xaa21 is selected from Leu, Ala, Arg, Lys and Glu. Preferably, Xaa21 is Leu or Glu, for example, Xaa21 is Glu. Alternatively, Xaa21 is Leu. In an especially preferred embodiment, Xaa21 is Glu.

Xaa28 is selected from Ala, Asn, Gln and His. Preferably, Xaa28 is selected from Ala, Gln and His. In an especially preferred embodiment, Xaa28 is Ala or Gln, for example Xaa28 is Ala. Alternatively, Xaa28 is Gln.

Xaa29 is selected from Gly and Ala. Preferably, Xaa29 is Gly.

Xaa33 is selected from Ser, His and Gln. For example, Xaa33 is selected from Ser and His, or alternatively Xaa33 is selected from Ser and Gln. Preferably, Xaa33 is Ser.

Xaa35 is selected from Lys, Pro, His, Arg, Asn, Gln, Glu, Ser and Ala. Preferably, Xaa35 is selected from Lys, Gln, Glu, His and Asn. In an especially preferred embodiment, Xaa35 is Lys.

Xaa36 is selected from Phe, His, Gln, Glu, Lys, Ser, Arg, or Xaa36 is absent. Preferably, Xaa36 is absent.

Xaa39 is selected from Pro or Gly. Preferably, Xaa39 is Pro.

Xaa40 is Gly, or Xaa40 is absent. Preferably, Xaa40 is Gly.

Xaa41 is Lys, or Xaa41 is absent. Preferably, Xaa41 is Lys.

In a preferred embodiment, Xaa36 is absent, and Xaa37-Xaa41 is Pro37-Pro38-Pro39-Gly40-Lys41 [SEQ ID NO: 533]. In an alternative preferred embodiment, Xaa36 is absent, Xaa40 is absent and Xaa37-Xaa41 is Pro37-Pro38-Pro39-Lys41 [SEQ ID NO: 534].

Group Y

In the compounds of the invention, the F-amino group on Lys42 is attached to the acid group of the Xaa44 residue of the Y portion of the molecule, such that the bond is an amide bond. If Xaa44 or Xaa43 is absent, then the F-amino group on Lys42 is attached to the acid group of the next residue that is present: the acid group of the Z group.

In a lysine residue, the F-amino group is the amino group that is attached to the 6-carbon. Following standard IUPAC nomenclature, the atoms in lysine are numbered as follows, indicating the carbon atom numbering and also the a to F positions:

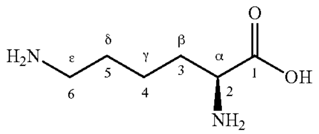

The F-amino group on Lys42 that is referred to herein is the amino group on the C-6 carbon atom as indicated.

Within the Y portion of the molecule:

Xaa43 may be Asn or absent; and

Xaa44 may be His or absent.

For example, Xaa43 is Asn and Xaa44 is His; or Xaa43 is Asn and Xaa44 is absent; or Xaa43 is absent and Xaa44 is His; or both Xaa43 and Xaa44 are absent. In a preferred embodiment, Xaa43 is absent and Xaa44 is absent.

For example, Y is:

Z-Asn-His-;

Z-Asn-;

Z-His-; or

Z—.

Group Z

Within the Z portion of the molecule, group R is an alkylene or alkenylene chain, which is linked at one end to residue Xaa43 (or, if Xaa43 is absent, Xaa44, or if both Xaa43 and Xaa44 are absent, Lys42) by the Glu residue through an amide bond. At its other end, the R alkylene or alkenylene chain is linked to the $R^1$ acid group ($CO_2H$).

Generally, R has an even number of carbon atoms. For example, R can be an alkylene or alkenylene chain that is found in naturally-occurring fatty acids. The root fatty acid has a chain length two higher than the number of carbon atoms in the R an alkylene or alkenylene chain.

R is a $C_{16}$-$C_{18}$ alkylene or alkenylene group. For example, R is straight chain alkylene or alkenylene group. For example, R is a $C_{16}$ or $C_{18}$ straight chain alkylene group. For example, when R is a $C_{16}$, group, it can be provided by a octadecanedioic acid moiety. For example, when R is a $C_{18}$, group, it can be provided by an eicosanedioic acid moiety.

In a preferred embodiment, R is a $C_{18}$ alkylene group.

In an embodiment, it is preferred that:

Xaa17 is Lys;

Xaa20 is Arg or His;

Xaa21 is Leu or Glu;

Xaa28 is Ala, Gln or His;

Xaa29 is Gly;

Xaa33 is Ser

Xaa35 is Lys, Glu, His, Gln or Asn;

Xaa36 is absent;

Xaa39 is Pro;

Xaa41 is Lys;

Xaa43 is absent;

Xaa44 is absent; and

R is a $C_{18}$ alkylene group.

In a more preferred embodiment:

Xaa1 is His or Phe;

Xaa3 is His or Glu;

Xaa10 is Tyr or Val;

Xaa17 is Lys;

Xaa18 is Ala or Arg;

Xaa20 is Arg or His;

Xaa21 is Glu;

Xaa28 is Ala or Gln;

Xaa35 is Lys; and

Xaa40 is Gly.

For example, in such an embodiment:

Xaa1 is Phe;

Xaa3 is Glu;

Xaa10 is Val;

Xaa18 is Arg;

Xaa20 is Arg; and

Xaa28 is Gln.

For example, such a compound can be a compound of SEQ ID No: 502.

In especially preferred embodiments, the compound is one of the compounds of the invention set out in the Table of FIG. 1.

Derivatives and Salts

The present invention provides compounds of formula (I), derivatives of such compounds, and salts or solvates of such compounds and derivatives.

The compounds, derivatives and salts may be produced by recombinant methods which are well-known in the art or alternatively they may be produced by synthetic methods, again which are well-known in the art.

Derivatives

Whilst in some embodiments, the invention relates to a compound of formula (I) and is not a derivative, in other embodiments the invention relates to a derivative of a compound of formula (I). The derivative may for example comprise one or more derivatisations selected from amidation, glycosylation, carbamylation, acylation, sulfation, phosphorylation, cyclization, lipidization, pegylation and fusion to another peptide or protein to form a fusion protein, for example the derivative may comprise one or more derivatisations selected from amidation, glycosylation, carbamylation, acylation, sulfation, phosphorylation, cyclization, lipidization and pegylation. The structure may be modified at random positions within the molecule, or at predetermined positions within the molecule and may include one, two, three or more attached chemical moieties.

In certain embodiments it is preferred that the primary peptide chain of compounds of the invention may be amidated at their C-terminal. Such a modification is very common in nature with approximately half of naturally occurring peptides, including certain gastrointestinal peptide hormones, being susceptible to amidation at their C-terminal. The present invention encompasses all of the generic and specific sequences disclosed herein, including in the sequence listing and drawings, in both amidated and non-amidated forms, the amidation, where present being especially preferred on the C-terminal of the primary peptide sequence.

The derivative may for example be a fusion protein, whereby the structure of formula (I) is fused to another protein or polypeptide (the fusion partner) using recombinant methods known in the art. Alternatively, such a fusion protein may be synthetically synthesized by any known method. Such a fusion protein comprises the structure of formula (I). Any suitable peptide or protein can be used as the fusion partner (e.g., serum albumin, carbonic anhydrase, glutathione-S-transferase or thioredoxin, etc.). Such fusion proteins may be made by linking the carboxy-terminus of the fusion partner to the amino-terminus of the structure of formula (I) or vice versa. Optionally, a cleavable linker may be used to link the structure of formula (I) to the fusion partner. A resulting cleavable fusion protein may be cleaved in vivo such that an active form of a compound of the invention is released. Examples of such cleavable linkers include, but are not limited to, the linkers Asp-Asp-Asp-Asp-Tyr [SEQ ID NO: 535], Gly-Pro-Arg, Ala-Gly-Gly and His-Pro-Phe-His-Leu [SEQ ID NO: 536], which can be cleaved by enterokinase, thrombin, ubiquitin cleaving enzyme and renin, respectively. For details, see for example U.S. Pat. No. 6,410,707, the contents of which are incorporated herein by reference.

A derivative of the invention may for example be a physiologically functional derivative of the structure of formula (I). The term "physiologically functional derivative" is used herein to denote a chemical derivative of a compound of formula (I) having the same physiological function as the corresponding unmodified compound. For example, a physiologically functionally derivative may be convertible in the body to a compound of formula (I). According to the present invention, examples of physiologically functional derivatives include esters, amides, and carbamates; preferably esters and amides.

In addition to the derivatisation at Lys42, compounds of the invention can be further derivatised at additional positions. For example, pharmaceutically acceptable esters and amides of the compounds of the invention may comprise a $C_{1-20}$ alkyl-, $C_{2-20}$ alkenyl-, $C_{5-10}$ aryl-, $C_{5-10}$ ar-$C_{1-20}$ alkyl-, or amino acid-ester group or amide group attached at an appropriate site, for example formed by reaction of an alkyl, alkenyl aryl, aralkyl or amino alkyl group containing an alcohol or amino moiety with an acid moiety present in the compound of formula (I), or formed by reaction of an alkyl, alkenyl aryl, aralkyl or amino alkyl group containing an activated acyl group with an alcohol or amine group present in the compound of formula (I). Examples of suitable moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H_{29}$) or stearyl ($C_{17}H_{35}$)) and bile acids (e.g. cholate or deoxycholate).

Methods for lipidization of sulfhydryl-containing compounds with fatty acid derivatives are disclosed in U.S. Pat. Nos. 5,936,092; 6,093,692; and 6,225,445, the contents of which are incorporated herein by reference. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds. Moreover, the disulfide linkage in a lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include fatty acids (e.g. lauroyl ($C_{12}H_{23}$), palmityl ($C_{15}H_{31}$), oleyl ($C_{15}H_{29}$) or stearyl ($C_{17}H_{35}$)) and bile acids (e.g. cholate or deoxycholate). Whilst lipid functionalised compounds of the invention may have benefits in certain situations, it is expected that in most cases, it will be simplest and preferred if a compound of the invention is not further derivatised, such that there are not additional lipid groups present.

Cyclization methods include cyclization through the formation of a disulfide bridge, and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

The derivative may for example be a PEGylated structure of formula (I). Derivatives which are PEGylated compounds of the invention may provide additional advantages such as increased solubility, stability and circulating time of the polypeptide, or decreased immunogenicity (see U.S. Pat. No. 4,179,337, the contents of which are incorporated herein by reference).

Chemical moieties for derivatisation of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any, on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 45,000, 50,000, 55,000, 60,000, 65,000, 70,000, 75,000, 80,000, 85,000, 90,000, 95,000, or 100,000 kDa.

Salts

Salt forms of compounds of formula (I) and of derivatives of such compounds also form part of the invention. In some embodiments the salt is a salt of a compound of formula (I). In other embodiments the salt is a salt of a derivative of a compound of formula (I).

Salts of compounds of the invention include those which are pharmaceutically acceptable, i.e. which are suitable for use in medicine. However, salts having non-pharmaceutically acceptable counterions are also within the scope of the present invention, for example, for use as intermediates in the preparation of the compounds.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycolic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic acid may be useful as intermediates in obtaining the compounds of the invention in final form.

Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Solvates

Those skilled in the art of organic and/or medicinal chemistry will appreciate that many organic compounds can form complexes with solvents in which they are reacted or from which they are precipitated or crystallized. Such complexes are known as "solvates". For example, a complex with water is known as a "hydrate". The invention also encompasses solvates of the compounds of formula (I), solvates of derivatives of the compounds, and solvates of salts of the derivatives.

Those skilled in the art of organic and/or medicinal chemistry will also appreciate than many organic compounds can exist in different forms, including as amorphous material and/or in one or more crystalline forms. Different physical forms of organic compounds are known as polymorphs. The invention also encompasses all such different physical forms of the compounds of formula (I), as well as different physical forms of their derivatives and salts.

Biological Activity

Compounds of the invention have activity at the human GLP-1 receptor and can be considered GLP-1 receptor agonists. This may be assessed by, for example, an in vitro or cellular binding assay or by a reporter assay. Preferred compounds of the invention exhibit an activity at the human GLP-1 receptor that is at least 1/50$^{th}$ that of human GLP-1, preferably an activity which is at least 1/30$^{th}$, 1/20$^{th}$, 1/10$^{th}$, 1/5$^{th}$, 1/3$^{rd}$ or 1/2 that of human GLP-1, for example when tested in accordance with the assay described in the examples section below.

Methods of assessing activity at the GLP-1 receptor are well known. For example, Jones et al., *Nat. Commun.,* 2018, 9(1), 1602 discloses a method of assaying for GLP-1 receptor binding. A specific method is described herein below.

Preferred compounds of the invention are effective in promoting insulin release/secretion. This may be assessed by, for example, an in vitro assay. Methods of assessing release of insulin from beta-cells are well known.

Compounds of the invention fulfil some, or more preferably all, of the following criteria:

1) Sustained bioactivity at the human GLP-1 receptor resulting in inhibition of appetite;
2) Activity in promoting insulin release from beta-cells;
3) High solubility in aqueous solution at pH 4.5 to allow an effective dose to be administered in a low volume injection (thereby resulting in lower pain of injection). Solubility may be easily assessed by simple in vitro tests;
4) Long period of activity in vivo (as assessed in humans or an animal model) so as to permit injections no more frequently than daily and preferably no more than twice, or more preferably no more than once a week, whilst still producing acceptable therapeutic or cosmetic benefits;
5) Good weight loss (as assessed in human subjects or an animal model);
6) Low antigenicity in humans. This may be assessed in humans or animal models (in particular mice which have been experimentally reconstituted with a human immune system so as to mimic human antibody repertoire) or predicted using predictive software such as that incorporating the "antigenic index" algorithm ((Jameson & Wolf (1988) *Comput. Appl. Biosci.* 4(1): 181-6), or the PREDITOP algorithm (Pellequer & Westhof, (1993) *J. Mol. Graph.* 11(3):204-10), or using the methods of Kolaskar & Tongaonkar (1990) FEBS Lett. 10:276(1-2):172-4, the contents of which are incorporated herein by reference).

According to certain embodiments of the invention, especially embodiments relating to weight loss, obesity, carbohydrate metabolism and diabetes, the compounds, derivatives and salts of the invention have one, several or all of the following features:

A. Sufficient solubility between pH 4 and pH 5 to permit an effective dose to be administered in a volume of less than 1 ml, less than 0.5 ml or less than 0.3 ml;
B. Activation of cAMP signalling in Chinese hamster ovary cells over-expressing the human GLP-1 Receptor;
C. One, several or all of the further 1 to 6 features listed above.

Pharmacokinetics, Duration of Action and Solubility

Compounds of the present invention exhibit potent and prolonged duration of action in vivo following subcutaneous administration. In order to achieve this, the compounds are required to have both good activity at the biological target, and excellent pharmacokinetic properties.

Compounds of the present invention have a therapeutically useful duration of action and that manifests itself in the beneficial effects being observed in the experiments described herein below over several days. The half-life of compounds of the invention was assessed in a pig PK model.

Preferred compounds of the invention were found to have a half-life significantly longer than semaglutide. As well as exhibiting a long in vivo half-life, the compounds of the invention have good storage stability, with no significant degradation seen on storage in solution for 4 weeks at 4° C.

Poor water solubility is a known problem for lipid containing molecules. In contrast, the compounds of the invention have very good solubility.

Certain compounds of the invention include His residues. Incorporation of His residue(s) into peptides having poor aqueous solubility typically leads to peptides having enhanced solubility at acidic pH (e.g. pH 5) due to the presence of charged His side-chain groups, but which are less soluble at physiological pH (pH 7.4). The pI of the side-chain group of histidine is about 6.0. Such properties enable formulation of His-containing peptides in weakly acidic media. Upon subcutaneous injection of such formulations, the solubility falls leading to subcutaneous precipitation of peptide which resolubilises over time. Zinc-containing formulations of His-containing peptides enhance this effect, because at pH 7.4 but not at pH 5 zinc ions coordinate with histidine residues and result in a further reduction in solubility which can contribute to increased precipitation at a subcutaneous injection site, or which can contribute to increased stability of the precipitate. However, where precipitation of peptide is not sufficiently rapid following subcutaneous administration, there may still be an initial "spike" or "burst" in blood concentration levels of the peptide. Such properties are undesirable since they increase the possibility of subjects experiencing side effects associated with high concentration levels of the peptides, such as nausea, even if only temporary. In contrast to peptides not having the multi-His containing C-terminal sequence of the invention, the present compounds either do not display initial "spikes" or "bursts" in plasma concentration levels following subcutaneous administration or any such "burst" is significantly reduced. This reduces the likelihood and/or severity of possible side effects associated with high circulating levels of the compounds.

Conditions

The invention also provides a compound, derivative or salt of the invention, or a composition comprising the compound, derivative or salt together with a pharmaceutically acceptable carrier and optionally a further therapeutic agent, for use as a medicament.

The invention also provides a method of treating or preventing a disease or disorder or other non-desired physiological state in a subject comprising administration of a therapeutically effective amount of a compound, derivative or salt of the invention, or of a composition comprising the compound, derivative or salt together with a pharmaceutically acceptable carrier and optionally a further therapeutic agent. Preferably the compound, derivative, salt or composition is administered subcutaneously.

According to certain embodiments, the disease or disorder or other non-desired physiological state is diabetes or obesity, and particularly diabetes (e.g. type II diabetes).

According to certain embodiments, the disease or disorder or other non-desired physiological state may be the physiological state of being overweight.

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes. The subject may be overweight, for example, obese and have diabetes mellitus, for example, Type II diabetes.

In addition, or alternatively, the subject may have, or may be at risk of having, a disorder in which obesity or being overweight is a risk factor. Such disorders include, but are not limited to, heart disease, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acanthosis *nigricans*; eczema; exercise intolerance; insulin resistance; hypertension hypercholesterolemia; cholithiasis; osteoarthritis; orthopedic injury; insulin resistance, for example, type 2 diabetes and syndrome X; and thromboembolic disease (see Kopelman, *Nature* 404: 635-43, 2000; Rissanen et al., *British Med. J.* 301, 835, 1990).

Other disorders associated with obesity include depression, anxiety, panic attacks, migraine headaches, PMS, chronic pain states, fibromyalgia, insomnia, impulsivity, obsessive compulsive disorder, and myoclonus. Certain neurological disorders and certain firms of neurological degeneration are also associated with obesity. Furthermore, obesity is a recognized risk factor for increased incidence of complications of general anesthesia (see e.g., Kopelman, *Nature* 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatitis; as well as abdominal hernias; acanthosis *nigricans*; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odours and infections in the skin folds under the breasts, etc.; large anterior abdominal wall masses, for example abdominal panniculitis with frequent panniculitis, impeding walking, causing frequent infections, odours, clothing difficulties, low back pain; musculoskeletal disease; pseudotumor cerebri (or benign intracranial hypertension), and sliding hiatal hernia.

In some embodiments, the disease or disorder may be non-alcoholic fatty liver disease.

According to certain embodiments the disease or disorder or other non-desired physiological state may be being of a non-desired weight despite not being obese or overweight. The subject may be of normal weight (this includes but is not limited to subjects who were previously overweight or obese and who wish to prevent a return to an unhealthy weight). A subject may be a subject who desires weight loss, for example female and/or male subjects who desire a change in their appearance. In some cases where the subject is of a normal weight, aspects of the invention may relate to cosmetic treatment rather than to therapeutic treatment.

The invention also provides a method of reducing appetite in a subject, reducing food intake in a subject, reducing calorie intake in a subject, improving insulin release in a subject, improving carbohydrate metabolism in a subject, and/or improving carbohydrate tolerance in a subject, comprising administration of a therapeutically effective amount of a compound, derivative, salt or composition of the invention. Such methods may relate to treating subjects having a pre-diabetic state such as insulin insensitivity or pre-diabetes.

The invention also provides a method for improving a lipid profile in a subject comprising administration of a therapeutically effective amount of a compound, derivative, salt or composition of the invention. The invention also provides a method for alleviating a condition or disorder that can be alleviated by reducing nutrient availability comprising administration of a therapeutically effective amount of a compound, derivative, salt or composition of the invention.

A compound, derivative, salt or composition of the invention may be used for weight control and treatment, for example reduction or prevention of obesity, in particular any one or more of the following: preventing and reducing weight gain; inducing and promoting weight loss; and reducing obesity as measured by the Body Mass Index. A compound, derivative, salt or composition of the invention may be used in maintaining any one or more of a desired body weight, a desired Body Mass Index, a desired appearance and good health.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

*J. Cereb. Blood Flow Metab.* 2011 Apr. 13 (Teramoto S et al.) discusses the use of both GLP-1 and exendin-4 to confer cardioprotection after myocardial infarction and demonstrates that exendin-4 may be used to provide neuroprotection against cerebral ischemia-reperfusion injury. The study showed that mice receiving a transvenous injection of exendin-4, after a 60-minute focal cerebral ischemia showed significantly reduced infarct volume and improved functional deficit as well as suppressed oxidative stress, inflammatory response, and cell death after reperfusion. The study provided evidence that the protective effect of exendin-4 is mediated through increased intracellular cAMP levels and suggested that exendin-4 is potentially useful in the treatment of acute ischemic stroke.

Accordingly, the invention also provides a method of providing cytoprotection in a subject, such as providing cardiac protection, providing neuroprotection and/or treating or preventing neurodegeneration, comprising administration of a therapeutically effective amount of a compound, derivative, salt or composition of the invention.

In certain embodiments the disease or disorder or other non-desired physiological state which the compound, derivative, salt or composition of the invention may be used to treat or prevent is neurodegeneration. Such neurodegeneration may be caused by apoptosis, necrosis or loss of function of neuronal cells, preferably in the CNS. Neurodegeneration treated or prevented may be that following a brain injury (for example following physical trauma or following a non-traumatic injury such a stroke, tumor, hypoxia, poisoning, infection, ischemia, encephalopathy or substance abuse). Alternatively or additionally, neurodegeneration may be prevented or treated in a subject having (or diagnosed as having a predisposition to) a neurodegenerative disease such as Alzheimer's disease, Parkinson's disease, Gehrig's disease (Amyotrophic Lateral Sclerosis), Huntington's disease, Multiple Sclerosis, other demyelination related disorders, senile dementia, subcortical dementia, arteriosclerotic dementia, AIDS-associated dementia, other dementias, cerebral vasculitis, epilepsy, Tourette's syndrome, Guillain Barre Syndrome, Wilson's disease, Pick's disease, neuroinflammatory disorders, encephalitis, encephalomyelitis, meningitis, other central nervous system infections, prion diseases, cerebellar ataxias, cerebellar degeneration, spinocerebellar degeneration syndromes, Friedrich's ataxia, ataxia teangiectasia, spinal dysmyotrophy, progressive supranuclear palsy, dystonia, muscle spasticity, tremor, retinitis pigmentosa, striatonigral degeneration, mitochondrial encephalomyopathies, neuronal ceroid lipofuscinosis. Preferably, the neurodegenerative disease is selected from the group consisting of Alzheimer's disease, Parkinson's disease, Gehrig's disease (Amyotrophic Lateral Sclerosis) and Huntington's disease. In such circumstances the treatment would be regarded as neuroprotective. According to certain preferred embodiments, the treatment is neuroprotective following cerebral ischemia or neuroprotective in a subject having a neurodegenerative disease or diagnosed as having a predisposition to a neurodegenerative disease.

According to other embodiments the disease or disorder or other non-desired physiological state is cardiac degeneration (in particular myocardial degeneration by apoptosis, necrosis or loss of function of myocardial cells), in which case the compound, derivative, salt or composition according to the invention provides cardiac protection. According to certain preferred embodiments that treatment is protective of myocardial function following myocardiac infarction.

The invention also provides a compound, derivative, salt or composition of the invention, for use in the treatment of obesity or diabetes.

The invention also provides a compound, derivative, salt or composition of the invention, for use in increasing energy expenditure of a subject, improving insulin release in a subject, improving carbohydrate tolerance in a subject and/or improving carbohydrate metabolism in a subject. Such use may relate to treating subjects having a pre-diabetic state such as insulin insensitivity or pre-diabetes.

The invention also provides a compound, derivative, salt or composition of the invention, for use in the reduction of appetite in a subject, use in the reduction of food intake in a subject, use in the reduction of calorie intake in a subject, use in improving insulin release in a subject, and/or use in improving carbohydrate tolerance in a subject. Such use may relate to treating subjects having a pre-diabetic state such as insulin insensitivity or pre-diabetes.

The invention also provides a compound, derivative, salt or composition of the invention, for use as a cytoprotective agent (e.g. in treating or preventing neurodegeneration, providing neuroprotection and/or providing cardiac protection). For example, the compound, derivative, salt or composition may be for use in myocardial protection in a subject following myocardial infarction, or for use in neuroprotection in a subject following cerebral ischemia or stroke, or for use in neuroprotection in a subject having a chronic neurodegenerative disease. Various features of neuroprotective or cardioprotective use of the compound, derivative, salt or composition may be as outlined above in relation to methods of the invention.

In the case of neuroprotection, the subject may have experienced previously a brain injury, stroke or other event causing cerebral ischemia. Alternatively, the subject may have or have been diagnosed with a predisposition to develop a chronic neurodegenerative disease. In the case of cardioprotection the subject may have experienced previously an event causing myocardial ischemia such as a myocardial infarction and angina. According to some embodiments a compound, derivative, salt or composition of the invention may be administered as soon as possible after the subject has experienced a suspected myocardial infarction. According to certain embodiments a compound, derivative, salt or composition of the invention may be administered as soon as possible after the subject has experienced as suspected stroke.

The invention also provides use of a compound, derivative, salt or composition of the invention for the manufacture of a medicament for the treatment of obesity or diabetes, of a subject, who may be as described above in reference to other aspects of the invention.

The invention also provides use of a compound, derivative or salt of the invention for the manufacture of a medicament for improving insulin release in a subject, for improving carbohydrate tolerance in a subject and/or improving carbohydrate metabolism in a subject. Such use may relate to treating subjects with a pre-diabetic state such as insulin insensitivity or pre-diabetes.

The invention also provides use of a compound, derivative or salt of the invention for the manufacture of a medicament for the reduction of appetite in a subject, reducing food intake in a subject, reducing calorie intake in a subject, improving insulin release in a subject, and/or use in improving carbohydrate tolerance in a subject.

The invention also provides use of a compound, derivative or salt of the invention for the manufacture of a medicament for providing cytoprotection (e.g. preventing or treating neurodegeneration, providing neuroprotection and/or providing cardiac protection) of a subject, who may be as described above in reference to other aspects of the invention.

According to certain embodiments the compound, derivative, salt or composition of the invention is to be administered parentally. According to other embodiments the compound, derivative, salt or composition of the invention is administered subcutaneously, intravenously, intramuscularly, intranasally, transdermally or sublingually. According to other embodiments the compound, derivative, salt or composition of the invention is administered orally. In one preferred embodiment compound, derivative, salt or composition of the invention is administered subcutaneously.

The compound, derivative, salt or composition of the invention is preferably used in the treatment of a human subject. However, while the compound, derivative, salt or composition of the invention will typically be used to treat human subjects they may also be used to treat similar or identical conditions in other vertebrates for example other primates; farm animals for example swine, cattle and poultry; sport animals for example horses; or companion animals for example dogs and cats.

Compositions

It is preferable for the compound of formula (I), or the derivative and/or the salt thereof, to be present in a pharmaceutical formulation or composition. Accordingly, the invention provides a composition comprising a compound, derivative or salt of the invention together with a pharmaceutically acceptable excipient and optionally another therapeutic ingredient. Compositions comprising the compound, derivative or salt are suitable for pharmaceutical use. According to certain preferred embodiments the composition is present in a syringe or other administration device for subcutaneous administration to humans. According to certain preferred embodiments the composition has a pH of less than 5. Compositions of the invention may take the form of a pharmaceutical formulation as described below.

The pharmaceutical formulations according to the invention include those suitable for oral, parenteral (including subcutaneous, intradermal, intramuscular, intravenous, and intra-articular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42:2S, 1988, the contents of which are incorporated herein by reference.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds or, particularly in the case of extended release, by the use of devices such as subcutaneous implants or osmotic pumps. The present compounds may also be administered liposomally.

Preferably, compositions according to the invention are suitable for subcutaneous administration, for example by injection. According to certain embodiments the composition may contain metal ions, for example copper, iron, aluminium, zinc, nickel or cobalt ions. The presence of such ions may limit solubility and thus delay absorption into the circulatory system from the site of subcutaneous administration.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. Such compositions may also include a permeation enhancer. The compounds of the invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include any compounds known to be deleterious to peptide compounds.

Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas.

In the case of a pressurized aerosol the dosage unit can be determined by providing a valve to deliver a metered amount. Capsules and cartridges of e.g. gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds, derivatives and salts of the invention may also be suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically, for example as a powder, ointment, gel, drop or transdermal patch; bucally; or as an oral or nasal spray.

Preparations for administration can be suitably formulated to give controlled release of compounds, derivatives and salts of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of particles of the compounds of the invention. These compositions exhibit certain biocompatibility features which allow a controlled release of the active substance, see U.S. Pat. No. 5,700,486, the contents of which are incorporated by reference.

The use of a controlled release composition is preferred for indications such as the treatment of obesity and/or diabetes, where maximising the time period between injections is desirable. However, for indications such as providing neuroprotection or cardiac protection (e.g. following suspected myocardial infarction or stroke), where it is desired to achieve a therapeutic plasma concentration of the active agent in as short a time period as possible, an immediate release formulation will be preferred. In such cases, a dosage regime comprising administration of a dose of an immediate release formulation of the active agent (i.e. as soon as possible after suspected myocardial infarction or stroke) and subsequent administration of a dose of a controlled release formulation of the active agent may be preferred.

A compound, derivative or salt of the invention may be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by a continuous subcutaneous infusion, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer (*Science* 249:1527-1533, 1990) which is incorporated herein by reference. In another aspect of the disclosure compounds of the invention are delivered by way of an implanted pump, described, for example, in U.S. Pat. Nos. 6,436,091; 5,939,380; 5,993,414, the contents of which are incorporated herein by reference.

Implantable drug infusion devices are used to provide patients with a constant and long-term dosage or infusion of a drug or any other therapeutic agent. Essentially such device may be categorized as either active or passive. A compound, derivative or salt of the present invention may be formulated as a depot preparation. Such a long acting depot formulation can be administered by implantation, for example subcutaneously or intramuscularly; or by intramuscular injection. Thus, for example, the active ingredient can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of the active agent of the invention may be administered as a single pulse dose, as a bolus dose, or as pulse doses administered over time. Thus, in pulse doses, a bolus administration of the active agent is provided, followed by a time period wherein no active agent is administered to the subject, followed by a second bolus administration. In specific, non-limiting examples, pulse doses are administered during the course of a day, during the course of a week, or during the course of a month.

Combination Treatments

In certain embodiments, a therapeutically effective amount of a compound, derivative, salt or composition of the invention is administered with a therapeutically effective amount of a further agent or agents. The compound, derivative or salt may for example be administered simultaneously with one or more further therapeutic agent(s), or it may be administered sequentially or separately. Accordingly, the invention provides a compound, derivative or salt of the invention for use as a medicament, wherein the compound, derivative or salt is for use with a therapeutically effective amount of a further therapeutic agent or agents (e.g. for administration simultaneously, sequentially or separately). In certain embodiments, the active agent of the invention is formulated and administered with a further therapeutic agent or agents as a single dose.

In certain embodiments, the further therapeutic agent or agents is/are an additional anti-diabetic, appetite suppressant, a food-intake-reducing, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, phendimetrazine, benzphetamine, sibutramine, rimonabant, topiramate, fluoxetine, bupropion, zonisamide, naltrexone, orlistat and cetilistat. Specific, non-limiting examples of an additional anti-diabetic agent include metformin, phenformin, rosiglitazone, pioglitazone, troglitazone, repaglinide, nateglinide, tolbutamide, acetohexamide, tolazamide, chlorpropamide, glipizide, glyburide, glimepiride, gliclazide, fibroblast growth factor 21, miglitol, acarbose, exenatide, pramlintide, vildagliptin and sitagliptin.

In alternative embodiments, the further therapeutic agent or agents is/are an additional cardioprotective or neuroprotective agent. Specific, non-limiting, examples of additional cardioprotective agents include aspirin, N-acetylcysteine, phenethylamines, coenzyme Q10, vitamin E, vitamin C, L-carnitine, carvedilol and dexrazoxane. Specific, non-limiting examples of neuroprotective agents include statins such as simvastatin, steroids such as progesterone, minocycline, resveratrol and vitamin E. Examples of agents used for the treatment of Parkinson's disease include anticholinergics, pramipexole, bromocriptine, levodopa, carbidopa, rasagiline, amantadine and ropinirole.

Dosages

A compound, derivative, salt or composition of the invention may be administered whenever the effect, e.g., appetite suppression, decreased food intake or decreased caloric intake, is desired, or slightly before to whenever the effect is desired, such as, but not limited to, about 10 minutes, about 15 minutes, about 30 minutes, about 60 minutes, about 90 minutes, or about 120 minutes, before the time the effect is desired.

The therapeutically effective amount of the active agent of the invention will be dependent on the molecule utilized, the subject being treated, the severity and type of the affliction, and the manner and route of administration. For example, a therapeutically effective amount of a compound of the invention may vary from about 0.01 g per kilogram (kg) body weight to about 1 g per kg body weight, for example about 0.1 g to about 20 mg per kg body weight, for example about 1 g to about 5 mg per kg body weight, or about 5 g to about 1 mg per kg body weight.

In one embodiment of the invention, a compound, derivative or salt of the invention may be administered to a subject at from 0.5 to 1,333 nmol per kg bodyweight, for example 1 to 1,333 nmol/kg bodyweight, for example 2 to 1,000 nmol per kg bodyweight, for example 4 to 1,333 nmol per kg bodyweight, for example from 5 to 1,000 nmol per kg bodyweight, for example at from 10 to 750 nmol per kg bodyweight, for example at from 20 to 500 nmol per kg bodyweight, in particular at from 30 to 240 nmol per kg bodyweight. In a preferred embodiment, a high activity compound of the invention is administered to a subject at from 0.2 to 10 nmol per kg bodyweight, for example 0.5 to 5.0 nmol/kg bodyweight, for example 1.0 to 2.0 nmol per kg bodyweight, for example 1.5 nmol per kg bodyweight. For a 75 kg subject, such doses correspond to dosages of from 37.5 nmol to 100 mol, for example from 75 nmol to 100 mol, for example from 150 nmol to 100 mol, for example from 300 nmol to 100 mol, for example from 375 nmol to 75 mol, for example from 750 nmol to 56.25 mol, for example from 1.5 to 37.5 mol, in particular from 2.25 to 18 mol. In a preferred embodiment for a high activity compound of the invention, for a 75 kg subject, such doses correspond to dosages of from 15 to 750 nmol, for example 37.5 to 375.0 nmol, for example 75 to 150 nmol, for example 112.5 nmol. The invention also contemplates dosages ranges bounded by any of the specific dosages mentioned herein.

The exact dose is readily determined by one of skill in the art based on the potency of the specific compound utilized, the route of delivery of the compound and the age, weight, sex and physiological condition of the subject.

For a compound with a long blood half-life, the doses discussed above may be given, for example, once or twice per month, or once, twice, three-times or four-times per week. For a preferred compound, a dose may be given no more frequently than once a week. Alternatively, for a compound with a shorter half-life in the blood, the doses discussed above may be given, for example, once, twice, three-times or four-times a day or once or twice a week. In some embodiments, a dose may be given once every 2, 3 or 4 days. According to certain embodiments they may be administered once shortly before each meal to be taken.

Examples

The invention is further described with reference to the following non-limiting examples.

Materials and Methods

Peptide Synthesis

Peptide synthesis was carried out on a tricyclic amide linker resin. Amino acids were attached using the Fmoc strategy. For the portion of the molecule from Xaa1 to Xaa42, each amino acid was added sequentially from the C- to the N-termini. Peptide couplings were mediated using reagents such as HBTU. Peptide cleavage from the resin was achieved with trifluoracetic acid in the presence of scavengers. In a second stage, the lysine 42 residue was functionalised at its F-amino group following deprotection of the F-amino group. The chain on the lysine 42 residue was then constructed sequentially using the same amino acid attachment chemistry.

Peptides were purified by reverse phase HPLC. Quality control was performed on all purified peptides and peptides were shown in most cases to be greater than 90% pure by HPLC in two buffer systems. MALDI-MS showed the expected molecular ion.

Example Synthesis

Example compound 193 (G Ref 6699) was prepared as follows using standard Fmoc chemistry:

Resin preparation: To 2Cl-Trt Resin (0.25 mmol, 1.00 eq) was added FMOC-LYS(DDE)-OH (133.15 mg, 250.00 mol, 1.00 eq) and DIEA (193.85 mg, 1.50 mmol, 261.97 μL, 6.00 eq) in DCM (8.0 mL). The mixture was agitated with $N_2$ for 2 h at 20° C., then added MeOH (0.25 mL) and agitated with $N_2$ for another 30 min. The resin was washed with DMF (12.0 mL*3). Then 20% piperidine in DMF (5.00 mL) was added and the mixture was agitated with $N_2$ for 30 min at 20° C. Then the mixture was filtered to get the resin. The resin was washed with DMF (12.0 mL*5) and filtered to get the resin.

FMOC-LYS(DDE)-OH has the Structure:

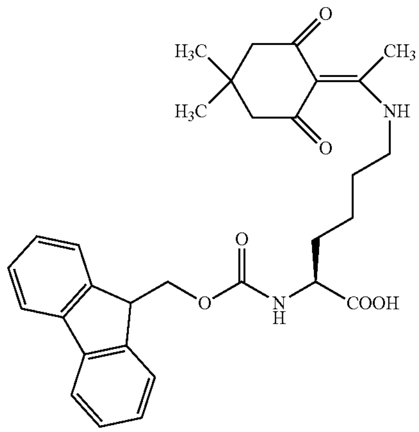 [SMILES: CC(NCCCC[C@H](NC(=O)OCC1c2ccccc2-c2ccccc21)C(=O)O)=C1C(=O)CC(C)(C)CC1=O]

The free acid is attached to the resin and the piperidine deprotection creates a free amino end group for the next coupling.

1. Coupling: a solution of FMOC-LYS(BOC)—OH (351.37 mg, 750.00 mol, 3.00 eq), DIEA (193.85 mg, 1.50 mmol, 261.97 μL, 6.00 eq) and HBTU (270.20 mg, 712.50 μmol, 2.85 eq) in DMF (3.00 mL) was added to the resin and agitated with $N_2$ for 30 min at 20° C. The resin was then washed with DMF (12.0 mL*3).
2. Deprotection: 20% piperidine in DMF (5.00 mL) was added to the resin and the mixture was agitated with $N_2$ for 30 min at 20° C. The resin was washed with DMF (12.0 mL*5) and filtered to get the resin.
3. Steps 2-3 were repeated using the reagents in Table 1 until the last amino acid had been added (reaction iteration #1 in Table 1 is the first added Lys residue, as set out in steps 2 and 3 above).

TABLE 1

| # | Materials | Coupling reagents |
|---|---|---|
| 1 | FMOC-PRO-OH (3.00 eq) | HBTU (2.85 eq) and DIPEA (6.00 eq) |
| 2 | FMOC-PRO-OH (3.00 eq) | HBTU (2.85 eq) and DIPEA (6.00 eq) |
| 3 | FMOC-PRO-OH (3.00 eq) | HBTU (2.85 eq) and DIPEA (6.00 eq) |
| 4 | FMOC-LYS(BOC)-OH (3.00 eq) | HBTU (2.85 eq) and DIPEA (6.00 eq) |
| 5 | FMOC-GLY-OH (3.00 eq) | HBTU (2.85 eq) and DIPEA (6.00 eq) |
| 6 | FMOC-SER(TBU)-OH (3.00 eq) | HBTU (2.85 eq) and DIPEA (6.00 eq) |
| 7 | FMOC-SER(TBU)-OH (3.00 eq) | HBTU (2.85 eq) and DIPEA (6.00 eq) |
| 8 | FMOC-PRO-OH (3.00 eq) | HBTU (2.85 eq) and DIPEA (6.00 eq) |
| 9 | FMOC-GLY-OH (3.00 eq) | HBTU (2.85 eq) and DIPEA (6.00 eq) |
| 10 | FMOC-GLY-OH (3.00 eq) | HBTU (2.85 eq) and DIPEA (6.00 eq) |
| 11 | FMOC-ALA-OH (3.00 eq) | HBTU (2.85 eq) and DIPEA (6.00 eq) |

TABLE 1-continued

| # | Materials | Coupling reagents |
|---|---|---|
| 12 | FMOC-LYS(BOC)-OH (3.00 eq) | HBTU (2.85 eq) and DIPEA (6.00 eq) |
| 13 | FMOC-LEU-OH (3.00 eq) | HBTU (2.85 eq) and DIPEA (6.00 eq) |
| 14 | FMOC-TRP(BOC)-OH (3.00 eq) | HBTU (2.85 eq) and DIPEA (6.00 eq) |
| 15 | FMOC-GLU(OTBU)-OH (3.00 eq) | HBTU (2.85 eq) and DIPEA (6.00 eq) |
| 16 | FMOC-ILE-OH (3.00 eq) | HBTU (2.85 eq) and DIPEA (6.00 eq) |
| 17 | FMOC-PHE-OH (3.00 eq) | HBTU (2.85 eq) and DIPEA (6.00 eq) |
| 18 | FMOC-LEU-OH (3.00 eq) | HBTU (2.85 eq) and DIPEA (6.00 eq) |
| 19 | FMOC-ARG(PBF)-OH (3.00 eq) | HBTU (2.85 eq) and DIPEA (6.00 eq) |
| 20 | FMOC-VAL-OH (3.00 eq) | HBTU (2.85 eq) and DIPEA (6.00 eq) |
| 21 | FMOC-ARG(PBF)-OH (3.00 eq) | HBTU (2.85 eq) and DIPEA (6.00 eq) |
| 22 | FMOC-GLU(OTBU)-OH (3.00 eq) | HBTU (2.85 eq) and DIPEA (6.00 eq) |
| 23 | FMOC-GLU(OTBU)-OH (3.00 eq) | HBTU (2.85 eq) and DIPEA (6.00 eq) |
| 24 | FMOC-GLU(OTBU)-OH (3.00 eq) | HBTU (2.85 eq) and DIPEA (6.00 eq) |
| 25 | FMOC-LEU-OH (3.00 eq) | HBTU (2.85 eq) and DIPEA (6.00 eq) |
| 26 | FMOC-GLN(TRT)-OH (3.00 eq) | HBTU (2.85 eq) and DIPEA (6.00 eq) |
| 27 | FMOC-LYS(BOC)-OH (3.00 eq) | HBTU (2.85 eq) and DIPEA (6.00 eq) |
| 28 | FMOC-SER(TBU)-OH (3.00 eq) | HBTU (2.85 eq) and DIPEA (6.00 eq) |
| 29 | FMOC-TYR(TBU)-OH (3.00 eq) | HBTU (2.85 eq) and DIPEA (6.00 eq) |
| 30 | FMOC-ASP(OTBU)-OH (3.00 eq) | HBTU (2.85 eq) and DIPEA (6.00 eq) |
| 31 | FMOC-SER(TBU)-OH (3.00 eq) | HBTU (2.85 eq) and DIPEA (6.00 eq) |
| 32 | FMOC-THR(TBU)-OH (3.00 eq) | HBTU (2.85 eq) and DIPEA (6.00 eq) |
| 33 | FMOC-PHE-OH (3.00 eq) | HBTU (2.85 eq) and DIPEA (6.00 eq) |
| 34 | FMOC-THR(TBU)-OH (3.00 eq) | HBTU (2.85 eq) and DIPEA (6.00 eq) |
| 35 | FMOC-GLY-OH (3.00 eq) | HBTU (2.85 eq) and DIPEA (6.00 eq) |
| 36 | FMOC-HIS(TRT)-OH (3.00 eq) | HBTU (2.85 eq) and DIPEA (6.00 eq) |
| 37 | FMOC-AIB-OH (3.00 eq) | HBTU (2.85 eq) and DIPEA (6.00 eq) |
| 38 | BOC-HIS(TRT)-OH (3.00 eq) | HBTU (2.85 eq) and DIPEA (6.00 eq) |

5. After the coupling of BOC—HIS(TRT)-OH in iteration #38, 3% $H_2N{\cdot}NH_2$/DMF was added and reacted for 30 min to remove Dde, and then repeated. The mixture was then drained and washed with DMF (15.0 mL) 5 times. After removal of the Dde group, the compound has a free amino end group at the F-amino group of the lysine from step 1 and that is available for the next coupling.
6. The reactions of steps 2-3 were then carried out using the reagents in Table 2 until the last reagent has been added (reaction iteration #40 in Table).

TABLE 2

| # | Materials | Coupling reagents |
|---|---|---|
| 39 | FMOC-GLU-OTBU (3.00 eq)* | HBTU (2.85 eq) and DIEA (6.00 eq) |
| 40 | 20-(tert-butoxy)-20-oxooctadecanoic acid (3.00 eq) | HBTU (2.85 eq) and DIEA (6.00 eq) |

* As the protected glutamic acid reagent 39 has its C-1 acid group protected with TBU, it reacts at its C-5 acid with the F-amino group of lysine 40. It is the FMOC-GLU-OTBU reagent that provides the glutamic acid residue portion in the Z part of the compound:

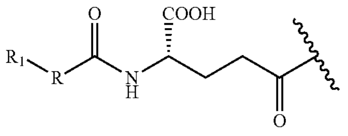

7. Peptide Cleavage and Purification:
The resin was washed with MeOH (20.0 mL*2) and dried under vacuum to provide 2.0 g peptide resin. Then 22.0 mL of cleavage buffer (92.5% TFA/2.5% Mpr/2.5% TIS/2.5% $H_2O$) was added to the flask containing the side chain protected peptide resin at 20° C. and the mixture was stirred for 2.5 h. The peptide was precipitated with cold tert-butyl methylether (250 mL) and centrifuged (2 min at 3000 rpm). The peptide precipitate was washed with tert-butyl methyl ether twice more (100 mL). The crude peptide was dried and the identity confirmed by LCMS.
The residue was purified by prep-HPLC (TFA condition; 30° C., A: 0.075% TFA/$H_2O$, B: $CH_3CN$) to give the title compound (202.4 mg, 40.66 μmol, 15.32% yield, 91.03% purity, TFA) as a white solid, the identity of which was confirmed by LCMS).

Equivalent methods were employed for all of the other peptides described herein. The sequences and other structural features of the exemplified peptides are shown in FIG. 1. In the FIGURE, the Lysine residue at position 42 is substituted on its F amino group with a group Y and Y is Z-Xaa43-Xaa44- (blank in the column in question means that the residue is absent), and Z is group a having the structure:

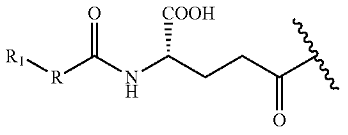

wherein R is a $C_{16}$-$C_{18}$ straight chain alkylene or alkenylene group; and
$R^1$ is $CO_2H$.

The number of carbon atoms in the alkylene or alkenylene group of R (n, n=16-18) is indicated in the column headed "n (R=Cn)" in FIG. 1. In the examples shown, n is 16 or 18.

Certain of the example compounds in FIG. 1 are duplicate preparations of compounds listed elsewhere in the FIGURE and they are indicated as such as "dupl" in the column headed 'Notes'.

Receptor Potency of Peptides at the Human GLP-1 Receptor, Overexpressed in CHO Cells Biological activity was assessed by potency of peptides to stimulate cAMP production in Chinese Hamster Ovary (CHO) cell lines overexpressing the human GLP receptor. Cells were plated at a density of $8\times10^{-5}$ cells/mL in serum-free media, into 96 well half area plates, on the day of the assay. A commercial cAMP kit (Cisbio) was used to quantify cAMP in the cell via HTRF (Homogeneous Time-Resolved Fluorescence) technology after 30 mins of peptide stimulation and a further 1 h lysis. Plates were read on a SpectraMax i3x Multi-Mode Detection Platform plate reader and concentration response curves drawn with Graph Pad Prism 7.0 (or higher). $EC_{50}$ values were generated for each peptide and compared to the controls for the day.

In Vivo Efficacy Study: Single Dose Feeding Studies in Male Rats

Male rats (Charles River Ltd, Margate, UK) were used for animal experiments. Ad libitum fed rats were individually housed in IVC cages. Animals were randomised into treatment groups, with stratification by body weight. All peptide solutions were prepared freshly immediately prior to administration. The control animals were dosed water 5% v/v water and 95% NaCl (0.9% w/v) whilst peptides (either 1.5, 2, 3 or 6 nmol/kg body weight) were resuspended in water for injection. Peptide and vehicle were administered in the early light phase (0900-1000) by subcutaneous injection and animals provided a known amount of food. Animals were given free access to food and water during the study period. Animal body weight and remaining food were weighed throughout the study, typically 24, 48, 72 and 96, and in some examples 168h post dosing. The results presented are the figures for 4 (96 h) or 7 days (168 h) post dosing.

The results for Example compounds 1 to 527 are shown in FIG. 1. The rats were dosed with a single subcutaneous injection of peptide. The dose was generally 1.5-6 nmol/kg body weight. In the Table in FIG. 1, column ‘n’ shows the number of times the compound in question was tested. Each test generally involved the compound being given to a group of 5 animals. The compounds were assessed for their propensity to inhibit food intake and their ability to bring about body weight change. The summation of their actions is reported as a single value, called “potency” in FIG. 1. The compounds were compared with semaglutide/Ozempic. For “potency”, a score of 8 means that the compound causes the same effect as Ozempic. A score above 8 indicates that there is greater inhibition of food intake and reduction in body weight and/or reduction in body weight gain than achieved by the same dose of Ozempic, or a similar effect to Ozempic but achieved with a lower dose of the test compounds. These high activity levels allow a compound to be administered at a lower dose than for semaglutide/Ozempic. In some cases, the dose can be ⅙th, $1/8^{th}$, $1/10^{th}$ or even $1/12^{th}$ of the level of semaglutide/Ozempic.

PK Measurements for Half-Life Assessment

Male large white pigs receive a single subcutaneous injection of the test compound at the start of study (0 hours). Repeated blood samples were taken from the pig over the proceeding 168 hours and plasma separated and stored at −20 to −80° C. Plasma concentration of the test compound was quantified using mass spectrum analysis. Time taken from $t_{max}$ to half of $C_{max}$ was calculated and represents the half-life ($t_{1/2}$) of the compound. Typically, the presented $t_{1/2}$ is the mean of four separate animals.

Results

FIG. 1 is a table providing amino acid sequences and other structural information for the example compounds of the invention. For example, the amino acid sequence of example compound no. 1 is as follows [SEQ ID NO: 1]:

His AIB His Gly Thr Phe Thr Ser Asp Leu Ser Lys Gln Leu Glu Glu Glu Ala Val Arg Leu Phe Ile Glu Trp Leu Lys Asn Gly Gly Pro Ser Ser Gly Ala Pro Pro Pro Lys

And the Lys residue at position 42 carries on its s-amino group a group Z, where Z is a group of formula:

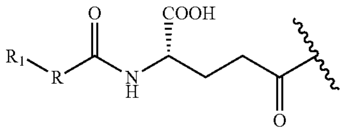

wherein R is a $C_{18}$ straight chain alkylene group; and $R^1$ is $CO_2H$.

The FIGURE also summarises the results of the in vivo feeding efficacy studies with the example peptides of the invention as discussed above.

To the right of the columns showing the feeding scores, the FIGURE shows receptor potency data for example peptides at the GLP-1 receptor, overexpressed in Chinese hamster ovary (CHO) cells. Biological activity was assessed by the potency of peptides to stimulate cAMP production in the CHO cells as described above.

As can be seen from the FIGURE, rats which were given free access to food and which were administered example peptides of the invention, achieved reduced weight gain or achieved weight loss compared with rats which were administered saline. This supports that the compounds of the invention are particularly effective at improving metabolism, and that they find use in the therapy of disorders such as obesity. However, the amount of food consumed by rats which were administered the example peptides was similar to or greater than the amount of food consumed by rats which were administered saline. The absence of, or only minimal, effect on amount of food ingested supports that the compounds have reduced side effects relating to nausea. As discussed above, rodents are not able to vomit, but those experiencing nausea are likely to be put off from consuming food. With the peptides of the invention, there was no observed evidence of the animals being put off consuming food.

Half-life:

The half-life of a selection of compounds of the invention was measured. The results, in hours, are shown in the column labelled t½ at the far right of the table in FIG. 1.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

SEQUENCE LISTING

```
Sequence total quantity: 536
SEQ ID NO: 1          moltype = AA  length = 39
FEATURE               Location/Qualifiers
REGION                1..39
                      note = Component of peptide hormone analogue
MOD_RES               2
```

-continued

```
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 1
HXHGTFTSDL SKQLEEEAVR LFIEWLKNGG PSSGAPPPK                          39

SEQ ID NO: 2            moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 2
HXHGTFTSDL SKQLEEERVR LFIEWLKNGG PSSGAPPPK                          39

SEQ ID NO: 3            moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 3
HXHGTFTSDL SKQLEEEAVR EFIEWLKNGG PSSGAPPPK                          39

SEQ ID NO: 4            moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 4
HXHGTFTSDL SKQLEEEAVR EFIEWLKHGG PSSGAPPPK                          39

SEQ ID NO: 5            moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 5
HXHGTFTSDL SKQLEEEAVR EFIEWLKQGG PSSGAPPPK                          39

SEQ ID NO: 6            moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
```

-continued

```
source                  1..39
                        mol_type = protein
                        organism = synthetic construct
SEQUENCE: 6
HXHGTFTSDL SKQLEEERVR LFIEWLKNGG PSSGAPPPK                        39

SEQ ID NO: 7            moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 7
HXHGTFTSDL SKQLEEERVR EFIEWLKNGG PSSGAPPPK                        39

SEQ ID NO: 8            moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 8
HXHGTFTSDL SKQLEEEAVR LFIEWLKNGG PSSGAPPPGK                       40

SEQ ID NO: 9            moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 9
HXHGTFTSDL SKQLEEEAVR EFIEWLKNGG PSSGAPPPGK                       40

SEQ ID NO: 10           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 10
HXHGTFTSDL SKQLEEERVR EFIEWLKNGG PSSGAPPPGK                       40

SEQ ID NO: 11           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 11
```

-continued

```
HXHGTFTSDL SKQLEEERVR EFIEWLKNGG PSSGAPPPGK                     40

SEQ ID NO: 12           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 12
HXHGTFTSDL SKQLEEERVR EFIEWLKHGG PSSGAPPPGK                     40

SEQ ID NO: 13           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 13
HXHGTFTSDL SKQLEEERVH EFIEWLKNGG PSSGAPPPGK                     40

SEQ ID NO: 14           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 14
HXHGTFTSDL SKQLEEERVR LFIEWLKNGG PSSGAPPPK                      39

SEQ ID NO: 15           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 15
HXHGTFTSDL SKQLEEERVR LFIEWLKNGG PSSGAPPPGK                     40

SEQ ID NO: 16           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 16
HXHGTFTSDL SKQLEEERVR LFIEWLKHGG PSSGAPPPGK                     40

SEQ ID NO: 17           moltype = AA  length = 40
FEATURE                 Location/Qualifiers
```

-continued

```
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 17
HXHGTFTSDL SKQLEEERVR LFIEWLKHGG PSHGAPPPGK                        40

SEQ ID NO: 18           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 18
HXHGTFTSDL SKQLEEERVR LFIEWLKHGG PSSGHPPPGK                        40

SEQ ID NO: 19           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 19
HXHGTFTSDL SKQLEEERVR LFIEWLKNGG PSHGHPPPGK                        40

SEQ ID NO: 20           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 20
HXHGTFTSDL SKQLEEERVR LFIEWLKNGG PSHGAPPPGK                        40

SEQ ID NO: 21           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 21
HXHGTFTSDL SKQLEEERVR LFIEWLKNGG PSSGHPPPGK                        40

SEQ ID NO: 22           moltype = AA  length = 39
FEATURE                 Location/Qualifiers
REGION                  1..39
                        note = Component of peptide hormone analogue
MOD_RES                 2
                        note = Aib
```

-continued

```
MOD_RES                 39
                        note = The residue at this position is Lys modified with a
                         Y group attached to its epsilon amino group
source                  1..39
                        mol_type = protein
                        organism = synthetic construct
SEQUENCE: 22
HXHGTFTSDL SKQLEEEAVR LFIEWLKNGG PSSGAPPPK                          39

SEQ ID NO: 23           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 23
FXHGTFTSDL SKQLEEEAVR LFIEWLKNGG PSSGAPPPK                          39

SEQ ID NO: 24           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 24
HXHGTFTSDL SKQLEEERVR LFIEWLKNGG PSSGHPPPK                          39

SEQ ID NO: 25           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 25
HXHGTFTSDL SKQLEEERVR LFIEWLKNGG PSSGKPPPK                          39

SEQ ID NO: 26           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 26
HXHGTFTSDL SKQLEEERVR LFIEWLKNGG PSHGAPPPK                          39

SEQ ID NO: 27           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
```

```
                        mol_type = protein
                        organism = synthetic construct
SEQUENCE: 27
HXHGTFTSDL SKQLEEERVR LFIEWLKNGG PSHGHPPPK                          39

SEQ ID NO: 28           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 28
HXHGTFTSDL SKQLEEEAVR EFIEWLKNGG PSHGHPPPK                          39

SEQ ID NO: 29           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 29
HXHGTFTSDL SKQLEEERVR LFIEWLKNGG PSHGHPPPK                          39

SEQ ID NO: 30           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 30
HXHGTFTSDL SKQLEEERVR EFIEWLKNGG PSHGHPPPK                          39

SEQ ID NO: 31           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 31
HXHGTFTSDL SKQLEEERVR LFIEWLKNGG PSHGHPPPK                          39

SEQ ID NO: 32           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 32
HXHGTFTSDL SKQLEEEAVR LFIEWLKNGG PSHGHPPPK                          39
```

```
SEQ ID NO: 33          moltype = AA  length = 39
FEATURE                Location/Qualifiers
REGION                 1..39
                       note = Component of peptide hormone analogue
MOD_RES                2
                       note = Aib
MOD_RES                39
                       note = The residue at this position is Lys modified with a
                        Y group attached to its epsilon amino group
source                 1..39
                       mol_type = protein
                       organism = synthetic construct
SEQUENCE: 33
HXHGTFTSDL SKQLEEEAVR LFIEWLKNGG PSHGHPPPK                        39

SEQ ID NO: 34          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 34
HXHGTFTSDL SKQLEEKRVR LFIEWLKNGG PSSGAPPPGK                       40

SEQ ID NO: 35          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 35
HXHGTFTSDL SKQLEEKAVR LFIEWLKNGG PSSGAPPPGK                       40

SEQ ID NO: 36          moltype = AA  length = 39
FEATURE                Location/Qualifiers
REGION                 1..39
                       note = Component of peptide hormone analogue
MOD_RES                2
                       note = Aib
MOD_RES                39
                       note = The residue at this position is Lys modified with a
                        Y group attached to its epsilon amino group
source                 1..39
                       mol_type = protein
                       organism = synthetic construct
SEQUENCE: 36
HXHGTFTSDL SKQLEEKRVR LFIEWLKNGG PSSGAPPPK                        39

SEQ ID NO: 37          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 37
HXHGTFTSDL SKQLEEKRVR LFIEWLKNGG PSSGAPPPGK                       40

SEQ ID NO: 38          moltype = AA  length = 40
FEATURE                Location/Qualifiers
REGION                 1..40
```

-continued

```
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 38
HXHGTFTSDL SKQLEEKRVR LFIEWLKNGG PSSGAPPPGK                       40

SEQ ID NO: 39         moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 39
HXHGTFTSDL SKQLEEEAVR LFIEWLKNGG PSSGAPPPGK                       40

SEQ ID NO: 40         moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 40
HXHGTFTSDL SKQLEEERVR LFIEWLKNGG PSSGAPPPGK                       40

SEQ ID NO: 41         moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 41
HXHGTFTSDL SKQLEEERVR LFIEWLKNGG PSSGHPPPGK                       40

SEQ ID NO: 42         moltype = AA  length = 39
FEATURE               Location/Qualifiers
REGION                1..39
                      note = Component of peptide hormone analogue
MOD_RES               2
                      note = Aib
MOD_RES               39
                      note = The residue at this position is Lys modified with a
                       Y group attached to its epsilon amino group
source                1..39
                      mol_type = protein
                      organism = synthetic construct
SEQUENCE: 42
HXHGTFTSDL SKQLEEKRVR LFIEWLKNGG PSSGAPPPK                        39

SEQ ID NO: 43         moltype = AA  length = 39
FEATURE               Location/Qualifiers
REGION                1..39
                      note = Component of peptide hormone analogue
MOD_RES               2
                      note = Aib
MOD_RES               39
```

```
                        note = The residue at this position is Lys modified with a
                         Y group attached to its epsilon amino group
source                  1..39
                        mol_type = protein
                        organism = synthetic construct
SEQUENCE: 43
HXHGTFTSDL SKQLEEKRVR LFIEWLKNGG PSHGHPPPK                          39

SEQ ID NO: 44           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 44
HXHGTFTSDL SKQLEEKRVR LFIEWLKNGG PSSGHPPPK                          39

SEQ ID NO: 45           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 45
HXHGTFTSDL SKQLEEERVR LFIEWLKNGG PSSGHPPPK                          39

SEQ ID NO: 46           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 46
HXHGTFTSDL SKQLEEKRVR LFIEWLKNGG PSSGHPPPGK                         40

SEQ ID NO: 47           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 47
HXHGTFTSDL SKQLEEEAVR LFIEWLKNGG PSSGHPPPGK                         40

SEQ ID NO: 48           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
```

```
                        organism = synthetic construct
SEQUENCE: 48
HXHGTFTSDL SKQLEEKAVR LFIEWLKNGG PSSGHPPPGK                        40

SEQ ID NO: 49           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 49
HXHGTFTSDL SKQLEEKRVR LFIEWLKNGG PSSGHPPPGK                        40

SEQ ID NO: 50           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 50
HXHGTFTSDL SKQLEEERVR LFIEWLKNGG PSSGAPPGK                         39

SEQ ID NO: 51           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 51
HXHGTFTSDL SKQLEEKRVR LFIEWLKNGG PSSGHPPGK                         39

SEQ ID NO: 52           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 52
HXHGTFTSDL SKQLEEKRVR LFIEWLKNGG PSSGAPPPGK                        40

SEQ ID NO: 53           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 53
HXHGTFTSDL SKQLEEKAVR LFIEWLKNGG PSSGAPPGK                         39
```

```
SEQ ID NO: 54          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 54
HXHGTFTSDL SKQLEEKRVR LFIEWLKNGG PSSGAPPPGK                        40

SEQ ID NO: 55          moltype = AA  length = 39
FEATURE                Location/Qualifiers
REGION                 1..39
                       note = Component of peptide hormone analogue
MOD_RES                2
                       note = Aib
MOD_RES                39
                       note = The residue at this position is Lys modified with a
                        Y group attached to its epsilon amino group
source                 1..39
                       mol_type = protein
                       organism = synthetic construct
SEQUENCE: 55
HXHGTFTSDL SKQLEEKRVR LFIEWLKNGG PSSGAPPPK                         39

SEQ ID NO: 56          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 56
HXHGTFTSDL SKQLEEKRVR LFIEWLKNGG PSSGAPPPGK                        40

SEQ ID NO: 57          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 57
HXHGTFTSDL SKQLEEKRVR LFIEWLKNGG PSSGHPPPGK                        40

SEQ ID NO: 58          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 58
HXHGTFTSDL SKQLEEKRVR LFIEWLKNGG PSSGKPPPGK                        40

SEQ ID NO: 59          moltype = AA  length = 40
FEATURE                Location/Qualifiers
REGION                 1..40
                       note = Component of peptide hormone analogue
```

```
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 59
HXHGTFTSDL SKQLEEKRVR LFIEWLKNGG PSSGKPPPGK                         40

SEQ ID NO: 60           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 60
HXHGTFTSDL SKQLEEKRVR LFIEWLKNGG PSSGAPPPK                          39

SEQ ID NO: 61           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 61
HXHGTFTSDL SKQLEEKRVR LFIEWLKNGG PSSGAPPPGK                         40

SEQ ID NO: 62           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 62
HXHGTFTSDL SKQLEEKRVR LFIEWLKNGG PSSGAPPPGK                         40

SEQ ID NO: 63           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 63
HXHGTFTSDL SKQLEEKRVR LFIEWLKNGG PSSGAPPPK                          39

SEQ ID NO: 64           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
```

-continued

```
                         Y group attached to its epsilon amino group
source                  1..40
                        mol_type = protein
                        organism = synthetic construct
SEQUENCE: 64
HXHGTFTSDY SKQLEEKRVR LFIEWLKQGG PSSGAPPPGK                        40

SEQ ID NO: 65           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 65
HXHGTFTSDL SKQLEEKRVR LFIEWLKNGG PSSGPPPGK                         39

SEQ ID NO: 66           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 66
HXHGTFTSDL SKQLEEKRVR LFIEWLKNGG PSSGAPPPGK                        40

SEQ ID NO: 67           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 67
HXHGTFTSDL SKQLEEKRVR LFIEWLKNAG PSSGAPPPGK                        40

SEQ ID NO: 68           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 68
HXHGTFTSDL SKQLEEKRVR LFIEWLKQGG PSSGAPPPGK                        40

SEQ ID NO: 69           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
```

-continued

```
SEQUENCE: 69
HXHGTFTSDL SKQLEEKRVR LFIEWLKQGG PSSGAPPPGK                        40

SEQ ID NO: 70          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 70
HXHGTFTSDL SKQLEEKRVR LFIEWLKNGG PSSGKPPPKK                        40

SEQ ID NO: 71          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 71
HXHGTFTSDL SKQLEEKRVR LFIEWLKNGG PSSGKPPPKK                        40

SEQ ID NO: 72          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 72
HXHGTFTSDL SKQLEEKRVR LFIEWLKNGG PSSGAPPPKK                        40

SEQ ID NO: 73          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 73
HXHGTFTSDL SKQLEEKRVR LFIEWLKNGG PSSGAPPPKK                        40

SEQ ID NO: 74          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y2 group attached to its epsilon amino group
source                 1..40
                       mol_type = protein
                       organism = synthetic construct
SEQUENCE: 74
HXHGTFTSDL SKQLEEKRVR LFIEWLKAGG PSSGAPPPGK                        40

SEQ ID NO: 75          moltype = AA  length = 39
```

-continued

```
FEATURE                Location/Qualifiers
REGION                 1..39
                       note = Component of peptide hormone analogue
MOD_RES                2
                       note = Aib
MOD_RES                39
                       note = The residue at this position is Lys modified with a
                        Y group attached to its epsilon amino group
source                 1..39
                       mol_type = protein
                       organism = synthetic construct
SEQUENCE: 75
HXHGTFTSDL SKQLEEKRVR LFIEWLKQGG PSSGAPPPK                         39

SEQ ID NO: 76          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 76
HXHGTFTSDY SKQLEEKRVR LFIEWLKAGG PSSGAPPPGK                        40

SEQ ID NO: 77          moltype = AA  length = 39
FEATURE                Location/Qualifiers
REGION                 1..39
                       note = Component of peptide hormone analogue
MOD_RES                2
                       note = Aib
MOD_RES                39
                       note = The residue at this position is Lys modified with a
                        Y group attached to its epsilon amino group
source                 1..39
                       mol_type = protein
                       organism = synthetic construct
SEQUENCE: 77
HXHGTFTSDY SKQLEEKRVR LFIEWLKQGG PSSGAPPPK                         39

SEQ ID NO: 78          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 78
HXHGTFTSDY SKQLEEKRVR LFIEWLKNAG PSSGAPPPGK                        40

SEQ ID NO: 79          moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 79
HXHGTFTSDL SKQLEEKRVR LFIEWLKQGG PSSGKPPPGK                        40

SEQ ID NO: 80          moltype = AA  length = 40
FEATURE                Location/Qualifiers
REGION                 1..40
                       note = Component of peptide hormone analogue
MOD_RES                2
```

```
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 80
HXHGTFTSDL SKQLEEKRVR LFIEWLKQGG PSSGKPPPGK                        40

SEQ ID NO: 81           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 81
HXHGTFTSDL SKQLEEKAVR LFIEWLKQGG PSSGKPPPGK                        40

SEQ ID NO: 82           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 82
HXHGTFTSDL SKQLEEKAVR LFIEWLKQGG PSSGKPPPGK                        40

SEQ ID NO: 83           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 83
HXHGTFTSDL SKQLEEERVR LFIEWLKQGG PSSGKPPPGK                        40

SEQ ID NO: 84           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 84
HXHGTFTSDL SKQLEEERVR LFIEWLKQGG PSSGKPPPGK                        40

SEQ ID NO: 85           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
```

-continued

```
source                  1..40
                        mol_type = protein
                        organism = synthetic construct
SEQUENCE: 85
HXHGTFTSDL SKQLEEKAVR LFIEWLKQGG PSSGHPPPGK                        40

SEQ ID NO: 86           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 86
HXHGTFTSDL SKQLEEERVR LFIEWLKQGG PSSGHPPPGK                        40

SEQ ID NO: 87           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 87
HXHGTFTSDL SKQLEEKRVR LFIEWLKQGG PSSGHPPPGK                        40

SEQ ID NO: 88           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 88
HXHGTFTSDL SKQLEEKRVR LFIEWLKQGG PSSGHPPPK                         39

SEQ ID NO: 89           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 89
HXHGTFTSDL SKQLEEKRVR LFIEWLKNAG PSSGHPPPGK                        40

SEQ ID NO: 90           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 90
```

-continued

```
HXHGTFTSDL SKQLEEKRVR LFIEWLKNAG PSSGHPPPK                      39

SEQ ID NO: 91           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 91
HXHGTFTSDY SKQLEEKRVR LFIEWLKHGG PSSGAPPPGK                     40

SEQ ID NO: 92           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 92
HXHGTFTSDL SKQLEEKRVR LFIEWLKHGG PSSGAPPPGK                     40

SEQ ID NO: 93           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 93
HXHGTFTSDY SKQLEEKRVR LFIEWLKHGG PSSGAPPPGK                     40

SEQ ID NO: 94           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 94
HXHGTFTSDL SKQLEEKRVR LFIEWLKHGG PSSGAPPPGK                     40

SEQ ID NO: 95           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 95
HXHGTFTSDL SKQLEEKRVR LFIEWLKHGG PSSGKPPPGK                     40

SEQ ID NO: 96           moltype = AA  length = 40
FEATURE                 Location/Qualifiers
```

-continued

```
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 96
HXHGTFTSDL SKQLEEKRVR LFIEWLKHGG PSSGHPPPGK                        40

SEQ ID NO: 97           moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 97
HXHGTFTSDL SKQLEEKRVR LFIEWLKNGG PSSGHPPPK                         39

SEQ ID NO: 98           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 98
HXHGTFTSDL SKQLEEKRVR EFIEWLKQGG PSSGAPPPGK                        40

SEQ ID NO: 99           moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 99
HXHGTFTSDL SKQLEEKRVH EFIEWLKQGG PSSGAPPPGK                        40

SEQ ID NO: 100          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 100
HXHGTFTSDL SKQLEEKRVR EFIEWLKQGG PSSGHPPPGK                        40

SEQ ID NO: 101          moltype = AA  length = 40
FEATURE                 Location/Qualifiers
REGION                  1..40
                        note = Component of peptide hormone analogue
MOD_RES                 2
                        note = Aib
```

-continued

```
MOD_RES                40
                       note = The residue at this position is Lys modified with a
                        Y group attached to its epsilon amino group
source                 1..40
                       mol_type = protein
                       organism = synthetic construct
SEQUENCE: 101
HXHGTFTSDL SKQLEEKRVH EFIEWLKQGG PSSGHPPPGK                        40

SEQ ID NO: 102         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 102
HXHGTFTSDL SKQLEEKRVR LFIEWLKQGG PSHGHPPPGK                        40

SEQ ID NO: 103         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 103
HXHGTFTSDL SKQLEEKRVH LFIEWLKQGG PSSGHPPPGK                        40

SEQ ID NO: 104         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 104
HXHGTFTSDY SKQLEEKRVR LFIEWLKQGG PSSGHPPPGK                        40

SEQ ID NO: 105         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 105
HXHGTFTSDL SKQLEEKRVQ EFIEWLKQGG PSSGHPPPGK                        40

SEQ ID NO: 106         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
```

```
                        mol_type = protein
                        organism = synthetic construct
SEQUENCE: 106
HXHGTFTSDL SKQLEEKRVR LFIEWLKNAG PSSGEPPPGK                         40

SEQ ID NO: 107          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 107
HXHGTFTSDL SKQLEEERVR LFIEWLKNAG PSSGHPPPGK                         40

SEQ ID NO: 108          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 108
HXHGTFTSDY SKQLEEKAVR LFIEWLKNAG PSSGAPPPKK                         40

SEQ ID NO: 109          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 109
HXHGTFTSDL SKQLEEKRVR LFIEWLKAGG PSSGAPPPKK                         40

SEQ ID NO: 110          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 110
HXHGTFTSDL SKQLEEKRVR LFIEWLKAGG PSSGAPPPKK                         40

SEQ ID NO: 111          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 111
HXHGTFTSDY SKQLEEKAVR LFIEWLKAGG PSSGAPPPGK                         40
```

```
SEQ ID NO: 112         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 112
HXHGTFTSDY SKQLEEKRVR LFIEWLKAGG PSSGKPPPGK                        40

SEQ ID NO: 113         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 113
HXHGTFTSDY SKQLEEKRVR LFIEWLKAGG PSSGAPPPKK                        40

SEQ ID NO: 114         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 114
HXHGTFTSDY SKQLEEKAVR LFIEWLKAGG PSSGAPPPKK                        40

SEQ ID NO: 115         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 115
HXHGTFTSDY SKQLEEKRVR LFIEWLKAGG PSSGKPPPKK                        40

SEQ ID NO: 116         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 116
HXHGTFTSDY SKQLEEKAVR LFIEWLKAGG PSSGAPPPKK                        40

SEQ ID NO: 117         moltype = AA  length = 40
FEATURE                Location/Qualifiers
REGION                 1..40
```

-continued

```
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 117
HXHGTFTSDY SKQLEEKAVR LFIEWLKAGG PSSGHPPPKK                        40

SEQ ID NO: 118           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 118
HXHGTFTSDY SKQLEEKAVR LFIEWLKAGG PSSGAPPPKK                        40

SEQ ID NO: 119           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 119
HXHGTFTSDY SKQLEEKAVR LFIEWLKAGG PSSGKPPPKK                        40

SEQ ID NO: 120           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 120
HXHGTFTSDY SKQLEEKAVR LFIEWLKAGG PSSGHPPPKK                        40

SEQ ID NO: 121           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 121
HXHGTFTSDY SKQLEEKAVR LFIEWLKAGG PSSGHPPPKK                        40

SEQ ID NO: 122           moltype = AA  length = 40
FEATURE                  Location/Qualifiers
REGION                   1..40
                         note = Component of peptide hormone analogue
MOD_RES                  2
                         note = Aib
MOD_RES                  40
```

-continued

```
                     note = The residue at this position is Lys modified with a
                      Y group attached to its epsilon amino group
source               1..40
                     mol_type = protein
                     organism = synthetic construct
SEQUENCE: 122
HXHGTFTSDL SKQLEEERVR LFIEWLKNAG PSSGHPPPKK                        40

SEQ ID NO: 123       moltype = AA  length = 40
FEATURE              Location/Qualifiers
REGION               1..40
                     note = Component of peptide hormone analogue
MOD_RES              2
                     note = Aib
MOD_RES              40
                     note = The residue at this position is Lys modified with a
                      Y group attached to its epsilon amino group
source               1..40
                     mol_type = protein
                     organism = synthetic construct
SEQUENCE: 123
HXHGTFTSDY SKQLEEERVR LFIEWLKNAG PSSGHPPPKK                        40

SEQ ID NO: 124       moltype = AA  length = 40
FEATURE              Location/Qualifiers
REGION               1..40
                     note = Component of peptide hormone analogue
MOD_RES              2
                     note = Aib
MOD_RES              40
                     note = The residue at this position is Lys modified with a
                      Y group attached to its epsilon amino group
source               1..40
                     mol_type = protein
                     organism = synthetic construct
SEQUENCE: 124
HXHGTFTSDY SKQLEEERVR LFIEWLKNAG PSSGKPPPKK                        40

SEQ ID NO: 125       moltype = AA  length = 40
FEATURE              Location/Qualifiers
REGION               1..40
                     note = Component of peptide hormone analogue
MOD_RES              2
                     note = Aib
MOD_RES              40
                     note = The residue at this position is Lys modified with a
                      Y group attached to its epsilon amino group
source               1..40
                     mol_type = protein
                     organism = synthetic construct
SEQUENCE: 125
HXHGTFTSDL SKQLEEERVR LFIEWLKNAG PSSGHPPPKK                        40

SEQ ID NO: 126       moltype = AA  length = 40
FEATURE              Location/Qualifiers
REGION               1..40
                     note = Component of peptide hormone analogue
MOD_RES              2
                     note = Aib
MOD_RES              40
                     note = The residue at this position is Lys modified with a
                      Y group attached to its epsilon amino group
source               1..40
                     mol_type = protein
                     organism = synthetic construct
SEQUENCE: 126
HXHGTFTSDY SKQLEEERVR LFIEWLKNAG PSSGHPPPKK                        40

SEQ ID NO: 127       moltype = AA  length = 40
FEATURE              Location/Qualifiers
REGION               1..40
                     note = Component of peptide hormone analogue
MOD_RES              2
                     note = Aib
MOD_RES              40
                     note = The residue at this position is Lys modified with a
                      Y group attached to its epsilon amino group
source               1..40
                     mol_type = protein
```

```
                        organism = synthetic construct
SEQUENCE: 127
HXHGTFTSDY SKQLEEERVR LFIEWLKNAG PSSGKPPPKK                        40

SEQ ID NO: 128          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 128
HXHGTFTSDY SKQLEEKRVR LFIEWLKAGG PSSGKPPPKK                        40

SEQ ID NO: 129          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 129
HXHGTFTSDY SKQLEEKRVR LFIEWLKAGG PSSGKPPPGK K                      41

SEQ ID NO: 130          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 130
HXHGTFTSDY SKQLEEKRVR LFIEWLKAGG PSSGHPPPGK K                      41

SEQ ID NO: 131          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 131
HXHGTFTSDY SKQLEEKRVR LFIEWLKHGG PSSGKPPPKK                        40

SEQ ID NO: 132          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 132
HXHGTFTSDY SKQLEEKRVR LFIEWLKHGG PSSGKPPPGK K                      41
```

```
SEQ ID NO: 133          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 133
HXHGTFTSDY SKQLEEKRVR LFIEWLKHGG PSSGHPPPGK K                      41

SEQ ID NO: 134          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 134
HXHGTFTSDY SKQLEEKRVR LFIEWLKHGG PSSGKPPPKK                        40

SEQ ID NO: 135          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 135
HXHGTFTSDY SKQLEEKRVR LFIEWLKHGG PSSGHPPPKK                        40

SEQ ID NO: 136          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 136
HXHGTFTSDY SKQLEEKRVR LFIEWLKHGG PSSGAPPPKK                        40

SEQ ID NO: 137          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 137
HXHGTFTSDL SKQLEEERVR LFIEWLKHGG PSSGKPPPKK                        40

SEQ ID NO: 138          moltype = AA  length = 40
FEATURE                 Location/Qualifiers
REGION                  1..40
                        note = Component of peptide hormone analogue
```

```
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 138
HXHGTFTSDL SKQLEEERVR LFIEWLKHGG PSSGHPPPKK                        40

SEQ ID NO: 139          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 139
HXHGTFTSDL SKQLEEKRVH EFIEWLKHGG PSSGKPPPKK                        40

SEQ ID NO: 140          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 140
HXHGTFTSDL SKQLEEKRVH EFIEWLKHGG PSSGKPPPKK                        40

SEQ ID NO: 141          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 141
HXHGTFTSDY SKQLEEKAVH EFIEWLKHGG PSSGKPPPKK                        40

SEQ ID NO: 142          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 142
HXHGTFTSDY SKQLEEKAVH EFIEWLKHGG PSSGKPPPKK                        40

SEQ ID NO: 143          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
```

```
                         Y group attached to its epsilon amino group
source                  1..40
                        mol_type = protein
                        organism = synthetic construct
SEQUENCE: 143
HXHGTFTSDY SKQLEEKAVH EFIEWLKAGG PSSGKPPPKK                        40

SEQ ID NO: 144          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 144
HXHGTFTSDY SKQLEEKAVH EFIEWLKAGG PSSGKPPPKK                        40

SEQ ID NO: 145          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 145
HXHGTFTSDY SKQLEEKRVR LFIEWLKNAG PSSGKPPPKK                        40

SEQ ID NO: 146          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 146
HXHGTFTSDY SKQLEEKRVR LFIEWLKNAG PSSGKPPPGK                        40

SEQ ID NO: 147          moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 147
HXHGTFTSDY SKQLEEKRVR LFIEWLKNAG PSSGKPPGK                         39

SEQ ID NO: 148          moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
```

```
SEQUENCE: 148
HXHGTFTSDY SKQLEEKRVR LFIEWLKNAG PSSGKPPGK                        39

SEQ ID NO: 149          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 149
HXHGTFTSDY SKQLEEERVR LFIEWLKNAG PSSGAPPPKK                       40

SEQ ID NO: 150          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 150
HXHGTFTSDY SKQLEEERVR LFIEWLKNAG PSSGKPPPGK                       40

SEQ ID NO: 151          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 151
HXHGTFTSDY SKQLEEERVR LFIEWLKNAG PSSGAPPPGK                       40

SEQ ID NO: 152          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 152
HXHGTFTSDY SKQLEEERVR LFIEWLKNAG PSSGAPPPGK                       40

SEQ ID NO: 153          moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 153
HXHGTFTSDY SKQLEEERVR LFIEWLKNAG PSSGKPPGK                        39

SEQ ID NO: 154          moltype = AA  length = 39
```

```
FEATURE                Location/Qualifiers
REGION                 1..39
                       note = Component of peptide hormone analogue
MOD_RES                2
                       note = Aib
MOD_RES                39
                       note = The residue at this position is Lys modified with a
                        Y group attached to its epsilon amino group
source                 1..39
                       mol_type = protein
                       organism = synthetic construct
SEQUENCE: 154
HXHGTFTSDY SKQLEEERVR LFIEWLKNAG PSSGKPPGK                         39

SEQ ID NO: 155         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 155
HXHGTFTSDL SKQLEEERVR LFIEWLKNAG PSSGKPPPKK                        40

SEQ ID NO: 156         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 156
HXHGTFTSDL SKQLEEERVR LFIEWLKNAG PSSGRPPPKK                        40

SEQ ID NO: 157         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 157
HXHGTFTSDL SKQLEEERVR LFIEWLKNAG PSSGRPPPGK                        40

SEQ ID NO: 158         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 158
HXHGTFTSDL SKQLEEERVR LFIEWLKNAG PSSGHPPPGK                        40

SEQ ID NO: 159         moltype = AA  length = 40
FEATURE                Location/Qualifiers
REGION                 1..40
                       note = Component of peptide hormone analogue
MOD_RES                2
```

-continued

```
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 159
HXHGTFTSDY SKQLEEERVR LFIEWLKNAG PSSGHPPPGK                        40

SEQ ID NO: 160          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 160
HXHGTFTSDL SKQLEEERVR LFIEWLKNAG PSSGKPPPGK                        40

SEQ ID NO: 161          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 161
HXHGTFTSDL SKQLEEERVR LFIEWLKNAG PSSGKPPPGK                        40

SEQ ID NO: 162          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 162
HXHGTFTSDY SKQLEEERVR LFIEWLKAGG PSSGAPPPGK                        40

SEQ ID NO: 163          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 163
HXHGTFTSDY SKQLEEERVR LFIEWLKAGG PSSGAPPPGK                        40

SEQ ID NO: 164          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
```

-continued

```
source                  1..40
                        mol_type = protein
                        organism = synthetic construct
SEQUENCE: 164
HXHGTFTSDY SKQLEEERVR LFIEWLKAGG PSSGHPPPGK                        40

SEQ ID NO: 165          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 165
HXHGTFTSDL SKQLEEERVR LFIEWLKAGG PSSGAPPPGK                        40

SEQ ID NO: 166          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 166
HXHGTFTSDY SKQLEEERVR LFIEWLKAGG PSSGHPPPGK                        40

SEQ ID NO: 167          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 167
HXHGTFTSDY SKQLEEERVR LFIEWLKAGG PSSGHPPPGK                        40

SEQ ID NO: 168          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 168
HXHGTFTSDY SKQLEEERVR LFIEWLKAGG PSSGHPPPKK                        40

SEQ ID NO: 169          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 169
```

-continued

```
HXHGTFTSDY SKQLEEERVR LFIEWLKAGG PSSGHPPPKK                      40

SEQ ID NO: 170          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 170
HXHGTFTSDY SKQLEEERVR LFIEWLKAGG PSSGHPPPKK                      40

SEQ ID NO: 171          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 171
HXHGTFTSDY SKQLEEERVR LFIEWLKAGG PSSGHPPPGK K                    41

SEQ ID NO: 172          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 172
HXHGTFTSDY SKQLEEERVR LFIEWLKAGG PSSGKPPPGK                      40

SEQ ID NO: 173          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 173
HXHGTFTSDY SKQLEEERVR LFIEWLKAGG PSSGAPPPKK                      40

SEQ ID NO: 174          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 174
HXHGTFTSDY SKQLEEERVR LFIEWLKAGG PSSGHPPPKK                      40

SEQ ID NO: 175          moltype = AA  length = 40
FEATURE                 Location/Qualifiers
```

```
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 175
HXHGTFTSDY SKQLEEERVR LFIEWLKAGG PSSGAPPPKK                        40

SEQ ID NO: 176          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 176
HXHGTFTSDY SKQLEEERVR LFIEWLKHGG PSSGKPPPKK                        40

SEQ ID NO: 177          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 177
HXHGTFTSDY SKQLEEERVR LFIEWLKNAG PSSGHPPPKK                        40

SEQ ID NO: 178          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 178
HXHGTFTSDY SKQLEEERVR LFIEWLKHGG PSSGKPPPKK                        40

SEQ ID NO: 179          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 179
HXHGTFTSDY SKQLEEERVR LFIEWLKHGG PSSGKPPPGK K                      41

SEQ ID NO: 180          moltype = AA  length = 41
FEATURE                 Location/Qualifiers
REGION                  1..41
                        note = Component of peptide hormone analogue
MOD_RES                 2
                        note = Aib
```

```
MOD_RES                 41
                        note = The residue at this position is Lys modified with a
                         Y group attached to its epsilon amino group
source                  1..41
                        mol_type = protein
                        organism = synthetic construct
SEQUENCE: 180
HXHGTFTSDY SKQLEEERVR LFIEWLKHGG PSSGAPPPGK K                      41

SEQ ID NO: 181          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 181
HXHGTFTSDY SKQLEEERVR LFIEWLKHGG PSSGNPPPGK K                      41

SEQ ID NO: 182          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 182
HXHGTFTSDY SKQLEEERVR LFIEWLKHGG PSSGEPPPGK K                      41

SEQ ID NO: 183          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 183
HXHGTFTSDY SKQLEEERVR LFIEWLKHGG PSSGQPPPGK K                      41

SEQ ID NO: 184          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 184
HXHGTFTSDY SKQLEEERVR LFIEWLKHGG PSSGSPPPGK K                      41

SEQ ID NO: 185          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
```

```
                        mol_type = protein
                        organism = synthetic construct
SEQUENCE: 185
HXHGTFTSDY SKQLEEERVR LFIEWLKHGG PSSGHPPPKK                         40

SEQ ID NO: 186          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 186
HXHGTFTSDY SKQLEEERVR LFIEWLKHGG PSSGKPPPGK K                       41

SEQ ID NO: 187          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 187
HXHGTFTSDY SKQLEEKRVR LFIEWLKHGG PSSGHPPPGK K                       41

SEQ ID NO: 188          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 188
HXHGTFTSDY SKQLEEERVR LFIEWLKHGG PSSGKPPPGK K                       41

SEQ ID NO: 189          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 189
HXHGTFTSDY SKQLEEERVR LFIEWLKHGG PSSGHPPPGK K                       41

SEQ ID NO: 190          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 190
HXHGTFTSDY SKQLEEERVR LFIEWLKHGG PSSGHPPPGK K                       41
```

```
SEQ ID NO: 191          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 191
HXHGTFTSDY SKQLEEERVR LFIEWLKAGG PSSGKPPPGK                        40

SEQ ID NO: 192          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 192
HXHGTFTSDY SKQLEEKRVR LFIEWLKAGG PSSGKPPPGK                        40

SEQ ID NO: 193          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 193
HXHGTFTSDY SKQLEEERVR LFIEWLKAGG PSSGKPPPKK                        40

SEQ ID NO: 194          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 194
HXHGTFTSDY SKQLEEKRVR LFIEWLKNAG PSSGHPPPKK                        40

SEQ ID NO: 195          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 195
HXHGTFTSDY SKQLEEERVR LFIEWLKNAG PSSGHPPPGK K                      41

SEQ ID NO: 196          moltype = AA  length = 41
FEATURE                 Location/Qualifiers
REGION                  1..41
```

```
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 196
HXHGTFTSDY SKQLEEERVR LFIEWLKAGG PSSGKPPPGK K                        41

SEQ ID NO: 197          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 197
HXHGTFTSDY SKQLEEERVR LFIEWLKAGG PSSGKPPPGK K                        41

SEQ ID NO: 198          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 198
HXHGTFTSDY SKQLEEERVR LFIEWLKAGG PSSGHPPPGK K                        41

SEQ ID NO: 199          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 199
HXHGTFTSDY SKQLEEERVH LFIEWLKQGG PSSGHPPPGK                          40

SEQ ID NO: 200          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 200
HXHGTFTSDY SKQLEEKRVH LFIEWLKHGG PSSGHPPPGK                          40

SEQ ID NO: 201          moltype = AA  length = 40
FEATURE                 Location/Qualifiers
REGION                  1..40
                        note = Component of peptide hormone analogue
MOD_RES                 2
                        note = Aib
MOD_RES                 40
```

```
                        note = The residue at this position is Lys modified with a
                         Y group attached to its epsilon amino group
source                  1..40
                        mol_type = protein
                        organism = synthetic construct
SEQUENCE: 201
HXHGTFTSDY SKQLEEKRVH LFIEWLKAGG PSSGHPPPGK                         40

SEQ ID NO: 202          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 202
HXHGTFTSDY SKQLEEKRVH LFIEWLKHGG PSSGKPPPKK                         40

SEQ ID NO: 203          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 203
HXHGTFTSDY SKQLEEERVH LFIEWLKHGG PSSGKPPPKK                         40

SEQ ID NO: 204          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 204
HXHGTFTSDY SKQLEEERVH LFIEWLKHGG PSSGHPPPKK                         40

SEQ ID NO: 205          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 205
HXHGTFTSDY SKQLEEERVH LFIEWLKHGG PSSGHPPPKK                         40

SEQ ID NO: 206          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
```

```
                        organism = synthetic construct
SEQUENCE: 206
HXHGTFTSDY SKQLEEERVH LFIEWLKNAG PSSGHPPPKK                        40

SEQ ID NO: 207          moltype = AA  length = 39
FEATURE                 Location/Qualifiers
REGION                  1..39
                        note = Component of peptide hormone analogue
MOD_RES                 2
                        note = Aib
MOD_RES                 39
                        note = The residue at this position is Lys modified with a
                         Y group attached to its epsilon amino group
source                  1..39
                        mol_type = protein
                        organism = synthetic construct
SEQUENCE: 207
HXHGTFTSDY SKQLEEERVH LFIEWLKAGG PSSGHPPPK                         39

SEQ ID NO: 208          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 208
HXHGTFTSDY SKQLEEERVH LFIEWLKHGG PSSGHPPPGK K                      41

SEQ ID NO: 209          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 209
HXHGTFTSDY SKQLEEERVH LFIEWLKHGG PSSGHPPPGK K                      41

SEQ ID NO: 210          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 210
HXHGTFTSDY SKQLEEERVH LFIEWLKAGG PSSGHPPPGK K                      41

SEQ ID NO: 211          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 211
HXHGTFTSDY SKQLEEERVH LFIEWLKAGG PSSGKPPPGK K                      41
```

-continued

```
SEQ ID NO: 212         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 212
HXHGTFTSDY SKQLEEERVH EFIEWLKQGG PSSGHPPPGK                        40

SEQ ID NO: 213         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 213
HXHGTFTSDY SKQLEEERVH EFIEWLKAGG PSSGHPPPGK                        40

SEQ ID NO: 214         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 214
HXHGTFTSDY SKQLEEERVH EFIEWLKHGG PSSGHPPPGK                        40

SEQ ID NO: 215         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 215
HXHGTFTSDY SKQLEEERVH EFIEWLKQGG PSSGHPPPGK K                      41

SEQ ID NO: 216         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 216
HXHGTFTSDY SKQLEEERVR EFIEWLKNAG PSSGAPPPGK                        40

SEQ ID NO: 217         moltype = AA  length = 40
FEATURE                Location/Qualifiers
REGION                 1..40
                       note = Component of peptide hormone analogue
```

```
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 217
HXHGTFTSDY SKQLEEKAVH EFIEWLKHGG PSSGHPPPKK                        40

SEQ ID NO: 218         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 218
HXHGTFTSDY SKQLEEKAVH EFIEWLKHGG PSSGHPPPGK                        40

SEQ ID NO: 219         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 219
HXHGTFTSDY SKQLEEERVH EFIEWLKHGG PSSGHPPPKK                        40

SEQ ID NO: 220         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 220
HXHGTFTSDY SKQLEEERVH EFIEWLKHGG PSSGHPPPGK                        40

SEQ ID NO: 221         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 221
HXHGTFTSDY SKQLEEERVH EFIEWLKHGG PSSGKPPPKK                        40

SEQ ID NO: 222         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
```

```
                         Y group attached to its epsilon amino group
source                  1..40
                        mol_type = protein
                        organism = synthetic construct
SEQUENCE: 222
HXHGTFTSDY SKQLEEERVH LFIEWLKAGG PSSGAPPPGK                        40

SEQ ID NO: 223          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 223
HXHGTFTSDY SKQLEEERVH LFIEWLKHGG PSSGAPPPGK                        40

SEQ ID NO: 224          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 224
HXHGTFTSDY SKQLEEERVH LFIEWLKAGG PSSGKPPPKK                        40

SEQ ID NO: 225          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 225
HXHGTFTSDY SKQLEEERVH EFIEWLKAGG PSSGKPPPKK                        40

SEQ ID NO: 226          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 226
HXHGTFTSDY SKQLEEKRVH EFIEWLKAGG PSSGKPPPKK                        40

SEQ ID NO: 227          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
```

```
SEQUENCE: 227
HXHGTFTSDY SKQLEEKRVH LFIEWLKAGG PSSGKPPPKK                       40

SEQ ID NO: 228         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 228
HXHGTFTSDY SKQLEEERVH EFIEWLKAGG PSSGHPPPKK                       40

SEQ ID NO: 229         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 229
HXHGTFTSDY SKQLEEERVR EFIEWLKAGG PSSGHPPPKK                       40

SEQ ID NO: 230         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 230
HXHGTFTSDY SKQLEEERVR EFIEWLKAGG PSSGKPPPKK                       40

SEQ ID NO: 231         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 231
HXHGTFTSDY SKQLEEERVR EFIEWLKAGG PSSGNPPPKK                       40

SEQ ID NO: 232         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 232
HXHGTFTSDY SKQLEEERVR EFIEWLKAGG PSSGEPPPKK                       40

SEQ ID NO: 233         moltype = AA  length = 40
```

```
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 233
HXHGTFTSDY SKQLEEERVR EFIEWLKAGG PSSGQPPPKK                         40

SEQ ID NO: 234         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 234
HXHGTFTSDY SKQLEEERVH LFIEWLKAGG PSSGHPPPKK                         40

SEQ ID NO: 235         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 235
HXHGTFTSDY SKQLEEERVH LFIEWLKAGG PSSGKPPPGK                         40

SEQ ID NO: 236         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 236
HXHGTFTSDY SKQLEEERVH LFIEWLKAGG PSSGNPPPKK                         40

SEQ ID NO: 237         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 237
HXHGTFTSDY SKQLEEERVH LFIEWLKAGG PSSGEPPPKK                         40

SEQ ID NO: 238         moltype = AA  length = 40
FEATURE                Location/Qualifiers
REGION                 1..40
                       note = Component of peptide hormone analogue
MOD_RES                2
```

```
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 238
HXHGTFTSDY SKQLEEERVH LFIEWLKAGG PSSGQPPPKK                        40

SEQ ID NO: 239        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 239
HXHGTFTSDY SKQLEEKAVH LFIEWLKAGG PSSGEPPPGK                        40

SEQ ID NO: 240        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 240
HXHGTFTSDY SKQLEEKAVH LFIEWLKAGG PSSGQPPPGK                        40

SEQ ID NO: 241        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 241
HXHGTFTSDY SKQLEEERVR LFIEWLKNGG PSSGAPPPGK                        40

SEQ ID NO: 242        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 242
HXHGTFTSDY SKQLEEERVR LFIEWLKNGG PSSGHPPPGK                        40

SEQ ID NO: 243        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
```

```
source                  1..40
                        mol_type = protein
                        organism = synthetic construct
SEQUENCE: 243
HXHGTFTSDY SKQLEEKRVR EFIEWLKQGG PSSGAPPPGK                        40

SEQ ID NO: 244          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 244
HXHGTFTSDY SKQLEEKRVR EFIEWLKQGG PSSGHPPPGK                        40

SEQ ID NO: 245          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 245
HXHGTFTSDY SKQLEEKRVH EFIEWLKHGG PSSGHPPPGK                        40

SEQ ID NO: 246          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 246
HXHGTFTSDY SKQLEEKRVH LFIEWLKQGG PSSGHPPPGK                        40

SEQ ID NO: 247          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 247
HXHGTFTSDY SKQLEEKRVH EFIEWLKAGG PSSGHPPPGK                        40

SEQ ID NO: 248          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 248
```

-continued

```
HXHGTFTSDY SKQLEEKRVR LFIEWLKAGG PSSGHPPPGK                        40

SEQ ID NO: 249          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 249
HXHGTFTSDY SKQLEEERVR LFIEWLKHGG PSSGHPPPGK                        40

SEQ ID NO: 250          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 250
HXHGTFTSDY SKQLEEERVR EFIEWLKAGG PSSGHPPPGK K                      41

SEQ ID NO: 251          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 251
HXHGTFTSDY SKQLEEERVR EFIEWLKAGG PSSGKPPPGK K                      41

SEQ ID NO: 252          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 252
HXHGTFTSDY SKQLEEERVH EFIEWLKAGG PSSGHPPPGK K                      41

SEQ ID NO: 253          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 253
HXHGTFTSDY SKQLEEERVH EFIEWLKAGG PSSGKPPPGK K                      41

SEQ ID NO: 254          moltype = AA  length = 40
FEATURE                 Location/Qualifiers
```

-continued

```
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 254
HXHGTFTSDL SKQLEEERVR EFIEWLKHGG PSSGKPPPKK                         40

SEQ ID NO: 255        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 255
HXHGTFTSDY SKQLEEERVR EFIEWLKHGG PSSGKPPPKK                         40

SEQ ID NO: 256        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 256
HXHGTFTSDL SKQLEEERVH EFIEWLKHGG PSSGKPPPKK                         40

SEQ ID NO: 257        moltype = AA  length = 40
FEATURE               Location/Qualifiers
REGION                1..40
                      note = Component of peptide hormone analogue
MOD_RES               2
                      note = Aib
MOD_RES               40
                      note = The residue at this position is Lys modified with a
                       Y group attached to its epsilon amino group
source                1..40
                      mol_type = protein
                      organism = synthetic construct
SEQUENCE: 257
HXHGTFTSDY SKQLEEERVH EFIEWLKHGG PSSGKPPPKK                         40

SEQ ID NO: 258        moltype = AA  length = 41
FEATURE               Location/Qualifiers
REGION                1..41
                      note = Component of peptide hormone analogue
MOD_RES               2
                      note = Aib
MOD_RES               41
                      note = The residue at this position is Lys modified with a
                       Y group attached to its epsilon amino group
source                1..41
                      mol_type = protein
                      organism = synthetic construct
SEQUENCE: 258
HXHGTFTSDY SKQLEEKRVH EFIEWLKAGG PSSGKPPPGK K                       41

SEQ ID NO: 259        moltype = AA  length = 41
FEATURE               Location/Qualifiers
REGION                1..41
                      note = Component of peptide hormone analogue
MOD_RES               2
                      note = Aib
```

```
MOD_RES                 41
                        note = The residue at this position is Lys modified with a
                         Y group attached to its epsilon amino group
source                  1..41
                        mol_type = protein
                        organism = synthetic construct
SEQUENCE: 259
HXHGTFTSDY SKQLEEKAVH LFIEWLKAGG PSSGKPPPGK K                      41

SEQ ID NO: 260          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 260
HXHGTFTSDY SKQLEEKAVH LFIEWLKAGG PSSGKPPPKK                        40

SEQ ID NO: 261          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 261
HXHGTFTSDY SKQLEEKAVH EFIEWLKAGG PSSGKPPPGK K                      41

SEQ ID NO: 262          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 262
HXHGTFTSDY SKQLEEERVH LFIEWLKAGG PSSGKSPPPG KK                     42

SEQ ID NO: 263          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 263
HXHGTFTSDY SKQLEEERVH LFIEWLKAGG PSSGQSPPPG KK                     42

SEQ ID NO: 264          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
```

```
                       mol_type = protein
                       organism = synthetic construct
SEQUENCE: 264
HXHGTFTSDY SKQLEEERVH LFIEWLKAGG PSSGHSPPPG KK                     42

SEQ ID NO: 265         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 265
HXHGTFTSDY SKQLEEERVK LFIEWLKAGG PSSGKPPPGK K                      41

SEQ ID NO: 266         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 266
HXHGTFTSDY SKQLEEERVK EFIEWLKAGG PSSGKPPPGK K                      41

SEQ ID NO: 267         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 267
HXHGTFTSDY SKQLEEERVQ LFIEWLKAGG PSSGKPPPGK K                      41

SEQ ID NO: 268         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 268
HXHGTFTSDY SKQLEEKAVR LFIEWLKAGG PSSGHPPPGK                        40

SEQ ID NO: 269         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 269
HXHGTFTSDY SKQLEEKAVR LFIEWLKAGG PSSGKPPPGK                        40
```

```
SEQ ID NO: 270         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 270
HXHGTFTSDY SKQLEEKAVH LFIEWLKAGG PSSGKPPPGK                        40

SEQ ID NO: 271         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 271
HXHGTFTSDY SKQLEEKAVH LFIEWLKAGG PSSGEPPPGK K                      41

SEQ ID NO: 272         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 272
HXHGTFTSDY SKQLEEERVH LFIEWLKAGG PSSGHPPPGK                        40

SEQ ID NO: 273         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 273
HXHGTFTSDY SKQLEEKAVH LFIEWLKAGG PSSGHPPPGK                        40

SEQ ID NO: 274         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 274
HXHGTFTSDY SKQLEEKAVH LFIEWLKAGG PSSGNPPPGK                        40

SEQ ID NO: 275         moltype = AA  length = 40
FEATURE                Location/Qualifiers
REGION                 1..40
```

```
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 275
HXHGTFTSDY SKQLEEKAVR LFIEWLKAGG PSSGEPPPGK                        40

SEQ ID NO: 276          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 276
HXHGTFTSDY SKQLEEERVK LFIEWLKAGG PSSGEPPPGK                        40

SEQ ID NO: 277          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 277
HXHGTFTSDY SKQLEEKAVK LFIEWLKAGG PSSGEPPPGK                        40

SEQ ID NO: 278          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 278
HXHGTFTSDY SKQLEEERVR LFIEWLKAGG PSHGHPPPGK                        40

SEQ ID NO: 279          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 279
HXHGTFTSDY SKQLEEERVR LFIEWLKAGG PSHGHHPPPG K                      41

SEQ ID NO: 280          moltype = AA  length = 40
FEATURE                 Location/Qualifiers
REGION                  1..40
                        note = Component of peptide hormone analogue
MOD_RES                 2
                        note = Aib
MOD_RES                 40
```

```
                        note = The residue at this position is Lys modified with a
                         Y group attached to its epsilon amino group
source                  1..40
                        mol_type = protein
                        organism = synthetic construct
SEQUENCE: 280
HXHGTFTSDY SKQLEEKAVH LFIEWLKAGG PSHGHPPPGK                        40

SEQ ID NO: 281          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 281
HXHGTFTSDY SKQLEEERVH LFIEWLKAGG PSSGEPPPGK                        40

SEQ ID NO: 282          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 282
HXHGTFTSDY SKQLEEERVR LFIEWLKAGG PSSGEPPPGK                        40

SEQ ID NO: 283          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 283
HXHGTFTSDY SKQLEEKRVR EFIEWLKQGG PSSGEPPPGK                        40

SEQ ID NO: 284          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 284
HXHGTFTSDY SKQLEEKRVH LFIEWLKQGG PSSGEPPPGK                        40

SEQ ID NO: 285          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
```

```
                         organism = synthetic construct
SEQUENCE: 285
HXHGTFTSDY SKQLEEKRVR EFIEWLKAGG PSSGEPPPGK                       40

SEQ ID NO: 286           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 286
HXHGTFTSDY SKQLEEKRVH LFIEWLKAGG PSSGEPPPGK                       40

SEQ ID NO: 287           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 287
HXHGTFTSDY SKQLEEKRVR EFIEWLKHGG PSSGEPPPGK                       40

SEQ ID NO: 288           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 288
HXHGTFTSDY SKQLEEKRVH LFIEWLKHGG PSSGEPPPGK                       40

SEQ ID NO: 289           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 289
HXHGTFTSDY SKQLEEKRVR EFIEWLKAGG PSHGHPPPGK                       40

SEQ ID NO: 290           moltype = AA  length = 40
FEATURE                  Location/Qualifiers
REGION                   1..40
                         note = Component of peptide hormone analogue
MOD_RES                  2
                         note = Aib
MOD_RES                  40
                         note = The residue at this position is Lys modified with a
                          Y group attached to its epsilon amino group
source                   1..40
                         mol_type = protein
                         organism = synthetic construct
SEQUENCE: 290
HXHGTFTSDY SKQLEEKRVH LFIEWLKAGG PSHGHPPPGK                       40
```

```
SEQ ID NO: 291         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 291
HXHGTFTSDY SKQLEEERVH EFIEWLKAGG PSSGEPPPGK                        40

SEQ ID NO: 292         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 292
HXHGTFTSDY SKQLEEERVH EFIEWLKAGG PSHGHPPPGK                        40

SEQ ID NO: 293         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 293
HXHGTFTSDY SKQLEEERVH EFIEWLKHGG PSSGAPPPGK                        40

SEQ ID NO: 294         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 294
HXHGTFTSDY SKQLEEERVH LFIEWLKHGG PSSGHPPPGK                        40

SEQ ID NO: 295         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 295
HXHGTFTSDY SKQLEEKAVH EFIEWLKAGG PSSGEPPPGK K                      41

SEQ ID NO: 296         moltype = AA  length = 41
FEATURE                Location/Qualifiers
REGION                 1..41
                       note = Component of peptide hormone analogue
```

```
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 296
HXHGTFTSDY SKQLEEKAVH EFIEWLKAGG PSSGHPPPGK K                      41

SEQ ID NO: 297         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 297
HXHGTFTSDY SKQLEEKAVH EFIEWLKHGG PSSGKPPPGK K                      41

SEQ ID NO: 298         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 298
HXHGTFTSDY SKQLEEKRVH LFIEWLKAGG PSSGKPPPGK K                      41

SEQ ID NO: 299         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 299
HXHGTFTSDY SKQLEEKRVR EFIEWLKAGG PSSGKPPPGK K                      41

SEQ ID NO: 300         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 300
HXHGTFTSDY SKQLEEKAVH LFIEWLKAGG PSSGHPPPGK K                      41

SEQ ID NO: 301         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
```

```
                         Y group attached to its epsilon amino group
source                  1..41
                        mol_type = protein
                        organism = synthetic construct
SEQUENCE: 301
HXHGTFTSDY SKQLEEKAVR EFIEWLKAGG PSSGKPPPGK K                       41

SEQ ID NO: 302          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 302
HXHGTFTSDY SKQLEEKRVH LFIEWLKAGG PSSGEPPPGK K                       41

SEQ ID NO: 303          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 303
HXHGTFTSDY SKQLEEKRVR EFIEWLKAGG PSSGEPPPGK K                       41

SEQ ID NO: 304          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 304
HXHGTFTSDY SKQLEEKRVR EFIEWLKAGG PSSGHPPPGK K                       41

SEQ ID NO: 305          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 305
HXHGTFTSDY SKQLEEKRVR EFIEWLKAGG PSSGAPPPGK                         40

SEQ ID NO: 306          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
```

```
SEQUENCE: 306
HXHGTFTSDY SKQLEEKRVR EFIEWLKAGG PSSGHPPPGK                       40

SEQ ID NO: 307          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 307
HXHGTFTSDY SKQLEEKRVR EFIEWLKAGG PSSGQPPPGK                       40

SEQ ID NO: 308          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 308
HXHGTFTSDY SKQLEEKRVR EFIEWLKQGG PSSGEPPPGK K                     41

SEQ ID NO: 309          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 309
HXHGTFTSDY SKQLEEKRVR EFIEWLKQGG PSSGHPPPGK K                     41

SEQ ID NO: 310          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 310
HXHGTFTSDY SKQLEEKRVR EFIEWLKHGG PSSGHPPPGK K                     41

SEQ ID NO: 311          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 311
HXHGTFTSDY SKQLEEKRVR EFIEWLKQGG PSSGKPPPGK K                     41

SEQ ID NO: 312          moltype = AA  length = 40
```

```
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 312
HXHGTFTSDY SKQLEEKAVR LFIEWLKAGG PSSGNPPPKK                        40

SEQ ID NO: 313         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 313
HXHGTFTSDY SKQLEEERVH EFIEWLKAGG PSSGNPPPKK                        40

SEQ ID NO: 314         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 314
HXHGTFTSDY SKQLEEKRVH EFIEWLKHGG PSSGNPPPKK                        40

SEQ ID NO: 315         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 315
HXHGTFTSDY SKQLEEERVR LFIEWLKHGG PSSGNPPPKK                        40

SEQ ID NO: 316         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 316
HXHGTFTSDY SKQLEEKRVR LFIEWLKQGG PSHGNPPPGK                        40

SEQ ID NO: 317         moltype = AA  length = 41
FEATURE                Location/Qualifiers
REGION                 1..41
                       note = Component of peptide hormone analogue
MOD_RES                2
```

```
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 317
HXHGTFTSDY SKQLEEKAVH EFIEWLKAGG PSSGNPPPGK K                      41

SEQ ID NO: 318          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 318
HXHGTFTSDY SKQLEEKRVR EFIEWLKQGG PSSGNPPPGK                        40

SEQ ID NO: 319          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 319
HXHGTFTSDY SKQLEEERVR EFIEWLKAGG PSSGNPPPGK                        40

SEQ ID NO: 320          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 320
HXHGTFTSDY SKQLEEKRVH EFIEWLKAGG PSSGNPPPGK K                      41

SEQ ID NO: 321          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 321
HXHGTFTSDY SKQLEEERVR LFIEWLKHGG PSSGNPPPGK K                      41

SEQ ID NO: 322          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
```

```
source                  1..40
                        mol_type = protein
                        organism = synthetic construct
SEQUENCE: 322
HXHGTFTSDY SKQLEEKAVK LFIEWLKAGG PSSGNPPPGK                        40

SEQ ID NO: 323          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 323
HXHGTFTSDY SKQLEEKRVR LFIEWLKAGG PSSGNPPPGK                        40

SEQ ID NO: 324          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 324
HXHGTFTSDY SKQLEEKAVK EFIEWLKAGG PSSGKPPPGK K                      41

SEQ ID NO: 325          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 325
HXHGTFTSDY SKQLEEKAVH EFIEWLKAGG PSSGKPPPGK K                      41

SEQ ID NO: 326          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 326
HXHGTFTSDY SKQLEEKAVH LFIEWLKAGG PSSGNPPPGK K                      41

SEQ ID NO: 327          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 327
```

```
HXHGTFTSDY SKQLEEKAVH EFIEWLKAGG PSSGNPPPKK                    40

SEQ ID NO: 328         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 328
HXHGTFTSDY SKQLEEKAVH EFIEWLKAGG PSSGEPPPKK                    40

SEQ ID NO: 329         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 329
HXHGTFTSDY SKQLEEKAVH EFIEWLKAGG PSSGEPPPGK K                  41

SEQ ID NO: 330         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 330
HXHGTFTSDY SKQLEEKAVR LFIEWLKAGG PSSGHPPPKK                    40

SEQ ID NO: 331         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 331
HXHGTFTSDY SKQLEEERVR LFIEWLKAGG PSSGKPPPKK                    40

SEQ ID NO: 332         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 332
HXHGTFTSDY SKQLEEERVH EFIEWLKAGG PSSGHPPPKK                    40

SEQ ID NO: 333         moltype = AA  length = 40
FEATURE                Location/Qualifiers
```

-continued

```
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 333
HXHGTFTSDL SKQLEEKRVH EFIEWLKHGG PSSGKPPPKK                        40

SEQ ID NO: 334          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 334
HXHGTFTSDY SKQLEEERVH EFIEWLKAGG PSSGKPPPKK                        40

SEQ ID NO: 335          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 335
HXHGTFTSDL SKQLEEERVR LFIEWLKHGG PSSGKPPPKK                        40

SEQ ID NO: 336          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 336
HXHGTFTSDY SKQLEEKRVR LFIEWLKAGG PSSGKPPPGK K                      41

SEQ ID NO: 337          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 337
HXHGTFTSDY SKQLEEKAVH EFIEWLKAGG PSHGKPPPGK K                      41

SEQ ID NO: 338          moltype = AA  length = 41
FEATURE                 Location/Qualifiers
REGION                  1..41
                        note = Component of peptide hormone analogue
MOD_RES                 2
                        note = Aib
```

```
MOD_RES                 41
                        note = The residue at this position is Lys modified with a
                         Y group attached to its epsilon amino group
source                  1..41
                        mol_type = protein
                        organism = synthetic construct
SEQUENCE: 338
HXHGTFTSDY SKQLEEKAVH EFIEWLKAGG PSHGEPPPGK K                      41

SEQ ID NO: 339          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 339
HXHGTFTSDY SKQLEEKAVH EFIEWLKAGG PSHGNPPPGK K                      41

SEQ ID NO: 340          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 340
HXHGTFTSDY SKQLEEKAVH EFIEWLKAGG PSHGHPPPGK K                      41

SEQ ID NO: 341          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 341
HXHGTFTSDY SKQLEEKAVR LFIEWLKAGG PSSGHPPPGK K                      41

SEQ ID NO: 342          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 342
HXHGTFTSDY SKQLEEKAVR EFIEWLKAGG PSSGHPPPGK K                      41

SEQ ID NO: 343          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
```

```
                        mol_type = protein
                        organism = synthetic construct
SEQUENCE: 343
HXHGTFTSDY SKQLEEKAVH EFIEWLKAGG PSHGKHPPPG KK                      42

SEQ ID NO: 344          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 344
HXHGTFTSDY SKQLEEKRVR EFIEWLKAGG PSHGHHPPPG KK                      42

SEQ ID NO: 345          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 345
HXHGTFTSDY SKQLEEKAVH EFIEWLKAGG PSHGHKPPPG KK                      42

SEQ ID NO: 346          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 346
HXHGTFTSDY SKQLEEKAVH EFIEWLKAGG PSHGHEPPPG KK                      42

SEQ ID NO: 347          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 347
HXHGTFTSDY SKQLEEKRVR EFIEWLKAGG PSHGNPPPGK                         40

SEQ ID NO: 348          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 348
HXHGTFTSDY SKQLEEKAVH EFIEWLKAGG PSHGNPPPGK                         40
```

```
SEQ ID NO: 349         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 349
HXHGTFTSDL SKQLEEKAVH EFIEWLKAGG PSHGNPPPGK                        40

SEQ ID NO: 350         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 350
HXHGTFTSDL SKQLEEKAVR LFIEWLKAGG PSSGHPPPKK                        40

SEQ ID NO: 351         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 351
HXHGTFTSDL SKQLEEERVR LFIEWLKAGG PSSGKPPPKK                        40

SEQ ID NO: 352         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 352
HXHGTFTSDY SKQLEEERVR LFIEWLKAGG PSSGKPPPGK K                      41

SEQ ID NO: 353         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 353
HXHGTFTSDY SKQLEEKAVR EFIEWLKAGG PSSGHPPPKK                        40

SEQ ID NO: 354         moltype = AA  length = 40
FEATURE                Location/Qualifiers
REGION                 1..40
```

-continued

```
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 354
HXHGTFTSDY SKQLEEERVR EFIEWLKAGG PSSGKPPPKK                        40

SEQ ID NO: 355          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 355
HXHGTFTSDY SKQLEEERVK EFIEWLKAGG PSSGKPPPKK                        40

SEQ ID NO: 356          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 356
HXHGTFTSDY SKQLEEKAVK LFIEWLKAGG PSSGHPPPKK                        40

SEQ ID NO: 357          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 357
HXHGTFTSDY SKQLEEERVK LFIEWLKAGG PSSGKPPPKK                        40

SEQ ID NO: 358          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 358
HXHGTFTSDY SKQLEEKAVH LFIEWLKAGG PSSGHPPPKK                        40

SEQ ID NO: 359          moltype = AA  length = 40
FEATURE                 Location/Qualifiers
REGION                  1..40
                        note = Component of peptide hormone analogue
MOD_RES                 2
                        note = Aib
MOD_RES                 40
```

```
                        note = The residue at this position is Lys modified with a
                         Y group attached to its epsilon amino group
source                  1..40
                        mol_type = protein
                        organism = synthetic construct
SEQUENCE: 359
HXHGTFTSDY SKQLEEERVH LFIEWLKAGG PSSGKPPPKK                        40

SEQ ID NO: 360          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 360
HXHGTFTSDY SKQLEEKAVH EFIEWLKAGG PSSGHPPPKK                        40

SEQ ID NO: 361          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 361
HXHGTFTSDV SKQLEEKAVR LFIEWLKAGG PSSGHPPPKK                        40

SEQ ID NO: 362          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 362
HXHGTFTSDV SKQLEEERVR LFIEWLKAGG PSSGKPPPKK                        40

SEQ ID NO: 363          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 363
HXHGTFTSDY SKQLEEKAVR LFIEWLKAGG PSSGKPPPKK                        40

SEQ ID NO: 364          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
```

-continued

```
                        organism = synthetic construct
SEQUENCE: 364
HXHGTFTSDY SKQLEEKAVR LFIEWLKAGG PSSGHPPPKK                        40

SEQ ID NO: 365          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 365
HXHGTFTSDL SKQLEEKAVR LFIEWLKAGG PSSGNPPPKK                        40

SEQ ID NO: 366          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 366
HXHGTFTSDL SKQLEEKAVR LFIEWLKAGG PSSGEPPPKK                        40

SEQ ID NO: 367          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 367
HXHGTFTSDY SKQLEEKRVR EFIEWLKAGG PSSGKPPPKK                        40

SEQ ID NO: 368          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 368
HXHGTFTSDY SKQLEEKRVR EFIEWLKAGG PSSGHPPPKK                        40

SEQ ID NO: 369          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 369
HXHGTFTSDY SKQLEEKRVR EFIEWLKAGG PSSGNPPPKK                        40
```

-continued

```
SEQ ID NO: 370         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 370
HXHGTFTSDY SKQLEEKRVR EFIEWLKAGG PSSGEPPPKK                        40

SEQ ID NO: 371         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 371
HXHGTFTSDY SKQLEEKRVR EFIEWLKAGG PSSGQPPPKK                        40

SEQ ID NO: 372         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 372
HXHGTFTSDL SKQLEEKRVH LFIEWLKQGG PSSGHPPPGK                        40

SEQ ID NO: 373         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 373
HXHGTFTSDY SKQLEEKRVR EFIEWLKAGG PSSGNPPPGK K                      41

SEQ ID NO: 374         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 374
HXHGTFTSDY SKQLEEKRVR EFIEWLKAGG PSSGQPPPGK K                      41

SEQ ID NO: 375         moltype = AA  length = 40
FEATURE                Location/Qualifiers
REGION                 1..40
                       note = Component of peptide hormone analogue
```

```
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 375
HXHGTFTSDY SKQLEEKRVR EFIEWLKAGG PSSGNPPPGK                        40

SEQ ID NO: 376         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 376
HXHGTFTSDY SKQLEEKRVR EFIEWLKAGG PSSGKPPPGK                        40

SEQ ID NO: 377         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 377
HXHGTFTSDY SKQLEEKAVR EFIEWLKAGG PSSGNPPPGK                        40

SEQ ID NO: 378         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 378
HXHGTFTSDY SKQLEEKAVR EFIEWLKAGG PSSGEPPPGK                        40

SEQ ID NO: 379         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 379
HXHGTFTSDY SKQLEEKAVR EFIEWLKAGG PSSGQPPPGK                        40

SEQ ID NO: 380         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
```

-continued

```
                         Y group attached to its epsilon amino group
source                  1..40
                        mol_type = protein
                        organism = synthetic construct
SEQUENCE: 380
HXHGTFTSDY SKQLEEKAVR EFIEWLKAGG PSSGHPPPGK                        40

SEQ ID NO: 381          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 381
HXHGTFTSDY SKQLEEKAVR EFIEWLKAGG PSSGKPPPGK                        40

SEQ ID NO: 382          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 382
HXHGTFTSDY SKQLEEKAVH EFIEWLKAGG PSSGNPPPGK                        40

SEQ ID NO: 383          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 383
HXHGTFTSDY SKQLEEKAVH EFIEWLKAGG PSSGEPPPGK                        40

SEQ ID NO: 384          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 384
HXHGTFTSDY SKQLEEKAVH EFIEWLKAGG PSSGQPPPGK                        40

SEQ ID NO: 385          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
```

```
SEQUENCE: 385
HXHGTFTSDY SKQLEEKAVH EFIEWLKAGG PSSGHPPPGK                        40

SEQ ID NO: 386         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 386
HXHGTFTSDY SKQLEEKAVH EFIEWLKAGG PSSGKPPPGK                        40

SEQ ID NO: 387         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 387
HXHGTFTSDL SKQLEEKRVR EFIEWLKHGG PSSGKPPPKK                        40

SEQ ID NO: 388         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 388
HXHGTFTSDY SKQLEEKAVR EFIEWLKAGG PSSGKPPPKK                        40

SEQ ID NO: 389         moltype = AA  length = 40
FEATURE                Location/Qualifiers
REGION                 1..40
                       note = Component of peptide hormone analogue
MOD_RES                2
                       note = Aib
MOD_RES                40
                       note = The residue at this position is Lys modified with a
                        Y group attached to its epsilon amino group
source                 1..40
                       mol_type = protein
                       organism = synthetic construct
SEQUENCE: 389
HXHGTFTSDY SKQLEEKAVK EFIEWLKAGG PSSGKPPPKK                        40

SEQ ID NO: 390         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 390
HXHGTFTSDL SKQLEEKRVR EFIEWLKHGG PSSGKPPPGK K                      41

SEQ ID NO: 391         moltype = AA  length = 41
```

-continued

```
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 391
HXHGTFTSDY SKQLEEKRVR EFIEWLKHGG PSSGKPPPGK K                      41

SEQ ID NO: 392         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 392
HXHGTFTSDY SKQLEEKAVK EFIEWLKAGG PSSGNPPPGK K                      41

SEQ ID NO: 393         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 393
HXHGTFTSDY SKQLEEKRVK EFIEWLKAGG PSSGNPPPGK K                      41

SEQ ID NO: 394         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 394
HXHGTFTSDY SKQLEEERVR EFIEWLKAGG PSSGQPPPGK K                      41

SEQ ID NO: 395         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 395
HXHGTFTSDY SKQLEEERVK EFIEWLKAGG PSSGNPPPGK K                      41

SEQ ID NO: 396         moltype = AA  length = 41
FEATURE                Location/Qualifiers
REGION                 1..41
                       note = Component of peptide hormone analogue
MOD_RES                2
```

```
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 396
HXHGTFTSDY SKQLEEERVK EFIEWLKAGG PSSGQPPPGK K                      41

SEQ ID NO: 397          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 397
HXHGTFTSDY SKQLEEERVK EFIEWLKAGG PSSGHPPPGK K                      41

SEQ ID NO: 398          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 398
HXHGTFTSDY SKQLEEKAVR EFIEWLKQGG PSSGKPPPGK K                      41

SEQ ID NO: 399          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 399
HXHGTFTSDY SKQLEEKAVK EFIEWLKQGG PSSGKPPPGK K                      41

SEQ ID NO: 400          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 400
HXHGTFTSDY SKQLEEERVR EFIEWLKAGG PSSGKPPPGK K                      41

SEQ ID NO: 401          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
```

```
source                  1..41
                        mol_type = protein
                        organism = synthetic construct
SEQUENCE: 401
HXHGTFTSDY SKQLEEKAVH EFIEWLKAGG PSSGKPPPGK K                     41

SEQ ID NO: 402          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 402
HXHGTFTSDY SKQLEEERVR EFIEWLKAGG PSSGKPPPGK K                     41

SEQ ID NO: 403          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 403
HXHGTFTSDY SKQLEEKAVH EFIEWLKAGG PSSGKPPPGK K                     41

SEQ ID NO: 404          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 404
HXHGTFTSDY SKQLEEKRVH EFIEWLKHGG PSSGKPPPGK K                     41

SEQ ID NO: 405          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 405
HXHGTFTSDY SKQLEEERVR LFIEWLKAGG PSSGQPPPKK                       40

SEQ ID NO: 406          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 406
```

```
HXHGTFTSDY SKQLEEERVR LFIEWLKAGG PSSGNPPPKK                       40

SEQ ID NO: 407          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 407
HXHGTFTSDY SKQLEEERVR LFIEWLKAGG PSSGEPPPKK                       40

SEQ ID NO: 408          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 408
HXHGTFTSDY SKQLEEERVR LFIEWLKAGG PSHGKPPPKK                       40

SEQ ID NO: 409          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 409
HXHGTFTSDY SKQLEEERVR LFIEWLKNAG PSSGKPPPGK K                     41

SEQ ID NO: 410          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 410
HXHGTFTSDY SKQLEEERVR EFIEWLKNAG PSSGKPPPGK K                     41

SEQ ID NO: 411          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 411
HXHGTFTSDY SKQLEEERVR EFIEWLKNAG PSSGKPPPKK                       40

SEQ ID NO: 412          moltype = AA  length = 40
FEATURE                 Location/Qualifiers
```

```
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 412
HXHGTFTSDY SKQLEEKRVK EFIEWLKAGG PSSGHPPPGK                         40

SEQ ID NO: 413          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 413
HXHGTFTSDL SKQLEEKRVR EFIEWLKAGG PSSGHPPPGK                         40

SEQ ID NO: 414          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 414
HXHGTFTSDY SKQLEEKRVR EFIEWLKNGG PSSGHPPPGK                         40

SEQ ID NO: 415          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 415
HXHGTFTSDY SKQLEEKRVR EFIEWLKNAG PSSGHPPPGK                         40

SEQ ID NO: 416          moltype = AA  length = 40
FEATURE                 Location/Qualifiers
REGION                  1..40
                        note = Component of peptide hormone analogue
MOD_RES                 2
                        note = Aib
MOD_RES                 40
                        note = The residue at this position is Lys modified with a
                         Y group attached to its epsilon amino group
source                  1..40
                        mol_type = protein
                        organism = synthetic construct
SEQUENCE: 416
HXHGTFTSDY SKQLEEKRVR EFIEWLKHGG PSSGHPPPGK                         40

SEQ ID NO: 417          moltype = AA  length = 42
FEATURE                 Location/Qualifiers
REGION                  1..42
                        note = Component of peptide hormone analogue
MOD_RES                 2
                        note = Aib
```

```
MOD_RES                 42
                        note = The residue at this position is Lys modified with a
                         Y group attached to its epsilon amino group
source                  1..42
                        mol_type = protein
                        organism = synthetic construct
SEQUENCE: 417
HXHGTFTSDY SKQLEEKRVR EFIEWLKAGG PSSGHQPPPG KK                    42

SEQ ID NO: 418          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 418
HXHGTFTSDY SKQLEEKRVR EFIEWLKAGG PSSGQHPPPG KK                    42

SEQ ID NO: 419          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 419
HXHGTFTSDY SKQLEEKRVR EFIEWLKAGG PSSGKQPPPG KK                    42

SEQ ID NO: 420          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 420
HXHGTFTSDY SKQLEEKRVR EFIEWLKAGG PSSGQQPPPG KK                    42

SEQ ID NO: 421          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 421
HXHGTFTSDY SKQLEEKRVR EFIEWLKAGG PSSGEFPPPG KK                    42

SEQ ID NO: 422          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
```

```
                        mol_type = protein
                        organism = synthetic construct
SEQUENCE: 422
HXHGTFTSDY SKQLEEKRVR EFIEWLKAGG PSSGKFPPPG KK                    42

SEQ ID NO: 423          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 423
HXHGTFTSDY SKQLEEKRVR EFIEWLKAGG PSSGKFPPGK K                     41

SEQ ID NO: 424          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 424
HXHGTFTSDY SKQLEEKRVR EFIEWLKAGG PSSGKQPPGK K                     41

SEQ ID NO: 425          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 425
HXHGTFTSDY SKQLEEKRVR EFIEWLKAGG PSSGPSPPPG KK                    42

SEQ ID NO: 426          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 426
HXHGTFTSDY SKQLEEKRVR EFIEWLKAGG PSSGKSPPPG KK                    42

SEQ ID NO: 427          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 427
HXHGTFTSDY SKQLEEKRVQ EFIEWLKAGG PSSGKPPPGK K                     41
```

```
SEQ ID NO: 428         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 428
HXHGTFTSDL SKQLEEKAVH EFIEWLKAGG PSSGKPPPGK K                      41

SEQ ID NO: 429         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 429
HXHGTFTSDL SKQLEEKAVR EFIEWLKAGG PSSGKPPPGK K                      41

SEQ ID NO: 430         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 430
HXHGTFTSDL SKQLEEERVR EFIEWLKAGG PSSGKPPPGK K                      41

SEQ ID NO: 431         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 431
HXHGTFTSDV SKQLEEKAVH EFIEWLKAGG PSSGKPPPGK K                      41

SEQ ID NO: 432         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 432
HXHGTFTSDV SKQLEEKAVR EFIEWLKAGG PSSGKPPPGK K                      41

SEQ ID NO: 433         moltype = AA  length = 41
FEATURE                Location/Qualifiers
REGION                 1..41
```

-continued

```
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 433
HXHGTFTSDV SKQLEEERVR EFIEWLKAGG PSSGKPPPGK K                      41

SEQ ID NO: 434          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 434
HXHGTFTSDY SKQLEEKAVH EFIEWLKAGG PSSGQPPPGK K                      41

SEQ ID NO: 435          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 435
HXHGTFTSDY SKQLEEKAVR EFIEWLKAGG PSSGQPPPGK K                      41

SEQ ID NO: 436          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 436
HXHGTFTSDY SKQLEEKAVR EFIEWLKAGG PSSGKKPPGK K                      41

SEQ ID NO: 437          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 437
HXHGTFTSDY SKQLEEKAVR EFIEWLKAGG PSSGKRPPGK K                      41

SEQ ID NO: 438          moltype = AA  length = 42
FEATURE                 Location/Qualifiers
REGION                  1..42
                        note = Component of peptide hormone analogue
MOD_RES                 2
                        note = Aib
MOD_RES                 42
```

-continued

```
                        note = The residue at this position is Lys modified with a
                         Y group attached to its epsilon amino group
source                  1..42
                        mol_type = protein
                        organism = synthetic construct
SEQUENCE: 438
HXHGTFTSDY SKQLEEKAVR EFIEWLKAGG PSSGKKPPPG KK                     42

SEQ ID NO: 439          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 439
HXHGTFTSDY SKQLEEKAVR EFIEWLKAGG PSSGKRPPPG KK                     42

SEQ ID NO: 440          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 440
HXHGTFTSDY SKQLEEKAVR EFIEWLKAGG PSSGRPPPGK K                      41

SEQ ID NO: 441          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 441
HXHGTFTSDY SKQLEEKAVR EFIEWLKAGG PSSGKEPPPG KK                     42

SEQ ID NO: 442          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 442
HXHGTFTSDY SKQLEEKAVR EFIEWLKAGG PSSGNPPPGK K                      41

SEQ ID NO: 443          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
```

```
                        organism = synthetic construct
SEQUENCE: 443
HXHGTFTSDY SKQLEEKAVR EFIEWLKAGG PSSGEPPPGK K                      41

SEQ ID NO: 444          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 444
HXHGTFTSDY SKQLEEKAVR EFIEWLKNAG PSSGKPPPGK K                      41

SEQ ID NO: 445          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 445
HXHGTFTSDY SKQLEEKAVR EFIEWLKHGG PSSGKPPPGK K                      41

SEQ ID NO: 446          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 446
HXHGTFTSDY SKQLEEKAVR EFIEWLKQGG PSSGKPPPGK K                      41

SEQ ID NO: 447          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 447
HXHGTFTSDY SKQLEEKAVR EFIEWLKQGG PSSGNPPPGK K                      41

SEQ ID NO: 448          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 448
HXHGTFTSDY SKQLEEKAVR EFIEWLKQGG PSSGEPPPGK K                      41
```

```
SEQ ID NO: 449         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 449
HXHGTFTSDY SKQLEEKAVR EFIEWLKQGG PSSGQPPPGK K                      41

SEQ ID NO: 450         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 450
HXHGTFTSDY SKQLEEKAVR EFIEWLKQGG PSSGHPPPGK K                      41

SEQ ID NO: 451         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 451
HXHGTFTSDV SKQLEEKRVR EFIEWLKQGG PSSGKPPPGK K                      41

SEQ ID NO: 452         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 452
HXHGTFTSDL SKQLEEKAVR EFIEWLKQGG PSSGKPPPGK K                      41

SEQ ID NO: 453         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 453
HXHGTFTSDV SKQLEEKRVR EFIEWLKQGG PSSGKPPPGK K                      41

SEQ ID NO: 454         moltype = AA  length = 41
FEATURE                Location/Qualifiers
REGION                 1..41
                       note = Component of peptide hormone analogue
```

-continued

```
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 454
HXHGTFTSDV SKQLEEKAVR EFIEWLKQGG PSSGKPPPGK K                      41

SEQ ID NO: 455         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 455
HXHGTFTSDY SKQLEEKAVR EFIEWLKAGG PSSGKPPPGK K                      41

SEQ ID NO: 456         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 456
HXHGTFTSDL SKQLEEKAVR EFIEWLKAGG PSSGNPPPGK K                      41

SEQ ID NO: 457         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 457
HXHGTFTSDL SKQLEEKAVR EFIEWLKQGG PSSGNPPPGK K                      41

SEQ ID NO: 458         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 458
HXHGTFTSDL SKQLEEKRVR EFIEWLKAGG PSSGNPPPGK K                      41

SEQ ID NO: 459         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
```

```
                        Y group attached to its epsilon amino group
source                  1..41
                        mol_type = protein
                        organism = synthetic construct
SEQUENCE: 459
HXHGTFTSDL SKQLEEKRVR EFIEWLKQGG PSSGNPPPGK K                       41

SEQ ID NO: 460          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 460
HXHGTFTSDL SKQLEEKRVR EFIEWLKAGG PSSGKPPPGK K                       41

SEQ ID NO: 461          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 461
HXHGTFTSDL SKQLEEKRVR EFIEWLKQGG PSSGKPPPGK K                       41

SEQ ID NO: 462          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 462
HXHGTFTSDL SKQLEEKRVR EFIEWLKHGG PSSGNPPPGK K                       41

SEQ ID NO: 463          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 463
HXHGTFTSDV SKQLEEKRVR EFIEWLKAGG PSSGNPPPGK K                       41

SEQ ID NO: 464          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
```

-continued

```
SEQUENCE: 464
HXHGTFTSDV SKQLEEKRVR EFIEWLKQGG PSSGNPPPGK K                     41

SEQ ID NO: 465         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 465
HXHGTFTSDL SKQLEEKAVR EFIEWLKQGG PSSGQPPPGK K                     41

SEQ ID NO: 466         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 466
HXHGTFTSDL SKQLEEKRVR EFIEWLKQGG PSSGQPPPGK K                     41

SEQ ID NO: 467         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 467
HXHGTFTSDL SKQLEEKAVR EFIEWLKAGG PSSGEPPPGK K                     41

SEQ ID NO: 468         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 468
HXHGTFTSDL SKQLEEKAVR EFIEWLKAGG PSSGQPPPGK K                     41

SEQ ID NO: 469         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 469
HXHGTFTSDL SKQLEEKAVR EFIEWLKAGG PSSGHPPPGK K                     41

SEQ ID NO: 470         moltype = AA  length = 41
```

```
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 470
HXHGTFTSDY SKQLEEKRVR EFIEWLKQGG PSSGQPPPGK K                       41

SEQ ID NO: 471          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 471
HXHGTFTSDV SKQLEEKAVR EFIEWLKAGG PSSGQPPPGK K                       41

SEQ ID NO: 472          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 472
HXHGTFTSDV SKQLEEKRVR EFIEWLKAGG PSSGKPPPGK K                       41

SEQ ID NO: 473          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 473
HXHGTFTSDV SKQLEEKAVH EFIEWLKQGG PSSGKPPPGK K                       41

SEQ ID NO: 474          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 474
HXHGTFTSDV SKQLEEKAVH EFIEWLKQGG PSSGHPPPGK K                       41

SEQ ID NO: 475          moltype = AA  length = 41
FEATURE                 Location/Qualifiers
REGION                  1..41
                        note = Component of peptide hormone analogue
MOD_RES                 2
```

```
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 475
HXHGTFTSDV SKQLEEKAVH EFIEWLKQGG PSSGQPPPGK K                      41

SEQ ID NO: 476          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 476
HXHGTFTSDV SKQLEEKAVH EFIEWLKAGG PSSGHPPPGK K                      41

SEQ ID NO: 477          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 477
HXHGTFTSDV SKQLEEKAVH EFIEWLKAGG PSSGQPPPGK K                      41

SEQ ID NO: 478          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 478
HXHGTFTSDV SKQLEEKAVR EFIEWLKQGG PSSGQPPPGK K                      41

SEQ ID NO: 479          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 479
HXHGTFTSDY SKQLEEKAVH EFIEWLKQGG PSSGKPPPGK K                      41

SEQ ID NO: 480          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
```

```
source                  1..41
                        mol_type = protein
                        organism = synthetic construct
SEQUENCE: 480
HXHGTFTSDL SKQLEEKAVH EFIEWLKQGG PSSGKPPPGK K                      41

SEQ ID NO: 481          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 481
HXHGTFTSDV SKQLEEKRVR EFIEWLKAGG PSSGQPPPGK K                      41

SEQ ID NO: 482          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 482
HXHGTFTSDV SKQLEEKRVR EFIEWLKQGG PSSGQPPPGK K                      41

SEQ ID NO: 483          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 483
HXHGTFTSDY SKQLEEKAVR EFIEWLKQGG PSSGKKPPGK K                      41

SEQ ID NO: 484          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 484
HXHGTFTSDV SKQLEEKAVR EFIEWLKQGG PSSGKKPPGK K                      41

SEQ ID NO: 485          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 485
```

```
HXHGTFTSDV SKQLEEKAVR EFIEWLKAGG PSSGKKPPGK K                    41

SEQ ID NO: 486          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 486
HXHGTFTSDV SKQLEEKAVR EFIEWLKAGG PSSGKKPPPG KK                   42

SEQ ID NO: 487          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 487
HXHGTFTSDV SKQLEEKRVR EFIEWLKQGG PSSGKKPPGK K                    41

SEQ ID NO: 488          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 488
HXHGTFTSDV SKQLEEKRVR EFIEWLKAGG PSSGKKPPGK K                    41

SEQ ID NO: 489          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 489
HXHGTFTSDV SKQLEEKAVR EFIEWLKQGG PSSGKPPPGK K                    41

SEQ ID NO: 490          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 490
HXHGTFTSDY SKQLEEKRVR EFIEWLKAGG PSSGKPPPGK K                    41

SEQ ID NO: 491          moltype = AA  length = 41
FEATURE                 Location/Qualifiers
```

-continued

```
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 491
YXHGTFTSDV SKQLEEKAVR EFIEWLKQGG PSSGKPPPGK K                       41

SEQ ID NO: 492          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 492
FXHGTFTSDV SKQLEEKAVR EFIEWLKQGG PSSGKPPPGK K                       41

SEQ ID NO: 493          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 493
YXEGTFTSDV SKQLEEKAVR EFIEWLKQGG PSSGKPPPGK K                       41

SEQ ID NO: 494          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 494
YXHGTFTSDY SKQLEEKAVR EFIEWLKQGG PSSGKPPPGK K                       41

SEQ ID NO: 495          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 495
FXHGTFTSDY SKQLEEKAVR EFIEWLKQGG PSSGKPPPGK K                       41

SEQ ID NO: 496          moltype = AA  length = 41
FEATURE                 Location/Qualifiers
REGION                  1..41
                        note = Component of peptide hormone analogue
MOD_RES                 2
                        note = Aib
```

```
MOD_RES                 41
                        note = The residue at this position is Lys modified with a
                         Y group attached to its epsilon amino group
source                  1..41
                        mol_type = protein
                        organism = synthetic construct
SEQUENCE: 496
YXEGTFTSDY SKQLEEKAVR EFIEWLKQGG PSSGKPPPGK K                      41

SEQ ID NO: 497          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 497
HXHGTFTSDY SKQLEEKRVR EFIEWLKQGG PSSGKPPPGK K                      41

SEQ ID NO: 498          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 498
YXHGTFTSDY SKQLEEKRVR EFIEWLKQGG PSSGKPPPGK K                      41

SEQ ID NO: 499          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 499
FXHGTFTSDY SKQLEEKRVR EFIEWLKQGG PSSGKPPPGK K                      41

SEQ ID NO: 500          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 500
YXEGTFTSDY SKQLEEKRVR EFIEWLKQGG PSSGKPPPGK K                      41

SEQ ID NO: 501          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
```

-continued

```
                        mol_type = protein
                        organism = synthetic construct
SEQUENCE: 501
FXEGTFTSDY SKQLEEKRVR EFIEWLKQGG PSSGKPPPGK K                       41

SEQ ID NO: 502          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 502
FXEGTFTSDV SKQLEEKRVR EFIEWLKQGG PSSGKPPPGK K                       41

SEQ ID NO: 503          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 503
FXEGTFTSDL SKQLEEKRVR EFIEWLKQGG PSSGKPPPGK K                       41

SEQ ID NO: 504          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 504
FXEGTFTSDY SKQLEEKAVR EFIEWLKQGG PSSGKPPPGK K                       41

SEQ ID NO: 505          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 505
FXEGTFTSDV SKQLEEKAVR EFIEWLKQGG PSSGKPPPGK K                       41

SEQ ID NO: 506          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 506
FXEGTFTSDL SKQLEEKAVR EFIEWLKQGG PSSGKPPPGK K                       41
```

```
SEQ ID NO: 507         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 507
HXEGTFTSDY SKQLEEKRVR EFIEWLKQGG PSSGKPPPGK K                      41

SEQ ID NO: 508         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 508
HXEGTFTSDY SKQLEEKAVR EFIEWLKAGG PSSGKPPPGK K                      41

SEQ ID NO: 509         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 509
HXEGTFTSDV SKQLEEKAVR EFIEWLKQGG PSSGKPPPGK K                      41

SEQ ID NO: 510         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 510
HXEGTFTSDY SKQLEEKAVR EFIEWLKQGG PSSGKPPPGK K                      41

SEQ ID NO: 511         moltype = AA  length = 41
FEATURE                Location/Qualifiers
REGION                 1..41
                       note = Component of peptide hormone analogue
MOD_RES                2
                       note = Aib
MOD_RES                41
                       note = The residue at this position is Lys modified with a
                        Y group attached to its epsilon amino group
source                 1..41
                       mol_type = protein
                       organism = synthetic construct
SEQUENCE: 511
HXEGTFTSDL SKQLEEKAVR EFIEWLKQGG PSSGKPPPGK K                      41

SEQ ID NO: 512         moltype = AA  length = 41
FEATURE                Location/Qualifiers
REGION                 1..41
```

-continued

```
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 512
FXQGTFTSDV SKQLEEKAVR EFIEWLKQGG PSSGKPPPGK K                      41

SEQ ID NO: 513          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 513
FXQGTFTSDV SKQLEEKRVR EFIEWLKQGG PSSGKPPPGK K                      41

SEQ ID NO: 514          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 514
HXQGTFTSDV SKQLEEKRVR EFIEWLKQGG PSSGKPPPGK K                      41

SEQ ID NO: 515          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 515
HXEGTFTSDV SKQLEEKRVR EFIEWLKQGG PSSGKPPPGK K                      41

SEQ ID NO: 516          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 516
YXEGTFTSDV SKQLEEKAVR EFIEWLKQGG PSSGKPPPGK K                      41

SEQ ID NO: 517          moltype = AA  length = 41
FEATURE                 Location/Qualifiers
REGION                  1..41
                        note = Component of peptide hormone analogue
MOD_RES                 2
                        note = Aib
MOD_RES                 41
```

```
                        note = The residue at this position is Lys modified with a
                         Y group attached to its epsilon amino group
source                  1..41
                        mol_type = protein
                        organism = synthetic construct
SEQUENCE: 517
YXEGTFTSDV SKQLEEKRVR EFIEWLKQGG PSSGKPPPGK K                      41

SEQ ID NO: 518          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 518
YXQGTFTSDV SKQLEEKAVR EFIEWLKQGG PSSGKPPPGK K                      41

SEQ ID NO: 519          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 519
HXQGTFTSDV SKQLEEKAVR EFIEWLKQGG PSSGKPPPGK K                      41

SEQ ID NO: 520          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 520
HXQGTFTSDV SKQLEEKAVR EFIEWLKAGG PSSGKKPPPG KK                     42

SEQ ID NO: 521          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
                        organism = synthetic construct
SEQUENCE: 521
HXQGTFTSDV SKQLEEKAVR EFIEWLKQGG PSSGKKPPPG KK                     42

SEQ ID NO: 522          moltype = AA  length = 42
FEATURE                 Location/Qualifiers
REGION                  1..42
                        note = Component of peptide hormone analogue
MOD_RES                 2
                        note = Aib
MOD_RES                 42
                        note = The residue at this position is Lys modified with a
                         Y group attached to its epsilon amino group
source                  1..42
                        mol_type = protein
```

```
                        organism = synthetic construct
SEQUENCE: 522
HXQGTFTSDV SKQLEEKRVR EFIEWLKQGG PSSGKKPPPG KK                    42

SEQ ID NO: 523          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 523
FXEGTFTSDV SKQLEEKRVR EFIEWLKQGG PSSGKPPPGK K                     41

SEQ ID NO: 524          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 524
FXEGTFTSDV SKQLEEKRVR EFIEWLKAGG PSSGKPPPGK K                     41

SEQ ID NO: 525          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 525
FXEGTFTSDV SKQLEEKRVR EFIEWLKQGG PSSGEPPPGK K                     41

SEQ ID NO: 526          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 526
FXEGTFTSDV SKQLEEKRVR EFIEWLKQGG PSSGQPPPGK K                     41

SEQ ID NO: 527          moltype = AA  length = 41
FEATURE                 Location/Qualifiers
REGION                  1..41
                        note = Component of peptide hormone analogue
MOD_RES                 2
                        note = Aib
MOD_RES                 41
                        note = The residue at this position is Lys modified with a
                         Y group attached to its epsilon amino group
source                  1..41
                        mol_type = protein
                        organism = synthetic construct
SEQUENCE: 527
FXEGTFTSDV SKQLEEKRVR EFIEWLKQGG PSSGKPPPGK K                     41
```

-continued

```
SEQ ID NO: 528          moltype = AA  length = 42
FEATURE                 Location/Qualifiers
REGION                  1..42
                        note = Component of peptide hormone analogue
VARIANT                 1
                        note = The residue at this position is His, Tyr or Phe
MOD_RES                 2
                        note = Aib
VARIANT                 3
                        note = The residue at this position is His, Gln or Glu
VARIANT                 10
                        note = The residue at this position is Leu, Tyr or Val
VARIANT                 17
                        note = The residue at this position is Glu or Lys
VARIANT                 18
                        note = The residue at this position is Ala or Arg
VARIANT                 20
                        note = The residue at this position is Arg, Gln, Lys or His
VARIANT                 21
                        note = The residue at this position is Leu, Ala, Arg, Lys
                         or Glu
VARIANT                 28
                        note = The residue at this position is Ala, Asn, Gln, His
VARIANT                 29
                        note = The residue at this position is Gly or Ala
VARIANT                 33
                        note = The residue at this position is Ser, His or Gln
VARIANT                 35
                        note = The residue at this position is Lys, Pro, His, Arg,
                         Asn, Gln, Glu, Ser or Ala
VARIANT                 36
                        note = The residue at this position is Phe, His, Gln, Glu,
                         Lys, Ser, Arg or absent
VARIANT                 39
                        note = The residue at this position is Pro or Gly
VARIANT                 40
                        note = The residue at this position is Gly or absent
VARIANT                 41
                        note = The residue at this position is Lys or absent
MOD_RES                 42
                        note = The residue at this position is Lys modified with a
                         Y2 group attached to its epsilon amino group
source                  1..42
                        mol_type = protein
                        organism = synthetic construct
SEQUENCE: 528
XXXGTFTSDX SKQLEEXXVX XFIEWLKXXG PSXGXXPPXX XK                     42

SEQ ID NO: 529          moltype = AA  length = 31
FEATURE                 Location/Qualifiers
source                  1..31
                        mol_type = protein
                        organism = Homo sapiens
SEQUENCE: 529
HAEGTFTSDV SSYLEGQAAK EFIAWLVKGR G                                 31

SEQ ID NO: 530          moltype = AA  length = 30
FEATURE                 Location/Qualifiers
MOD_RES                 30
                        note = AMIDATION
source                  1..30
                        mol_type = protein
                        organism = Homo sapiens
```

```
SEQUENCE: 530
HAEGTFTSDV SSYLEGQAAK EFIAWLVKGR                                   30

SEQ ID NO: 531         moltype = AA  length = 29
FEATURE                Location/Qualifiers
source                 1..29
                       mol_type = protein
                       organism = Homo sapiens
SEQUENCE: 531
HSQGTFTSDY SKYLDSRRAQ DFVQWLMNT                                    29

SEQ ID NO: 532         moltype = AA  length = 37
FEATURE                Location/Qualifiers
source                 1..37
                       mol_type = protein
                       organism = Homo sapiens
SEQUENCE: 532
HSQGTFTSDY SKYLDSRRAQ DFVQWLMNTK RNRNNIA                           37

SEQ ID NO: 533         moltype = AA  length = 5
FEATURE                Location/Qualifiers
REGION                 1..5
                       note = Component of peptide hormone analogue
source                 1..5
                       mol_type = protein
                       organism = synthetic construct
SEQUENCE: 533
PPPGK                                                              5

SEQ ID NO: 534         moltype = AA  length = 4
FEATURE                Location/Qualifiers
REGION                 1..4
                       note = Component of peptide hormone analogue
source                 1..4
                       mol_type = protein
                       organism = synthetic construct
SEQUENCE: 534
PPPK                                                               4

SEQ ID NO: 535         moltype = AA  length = 5
FEATURE                Location/Qualifiers
REGION                 1..5
                       note = Component of peptide hormone analogue
source                 1..5
                       mol_type = protein
                       organism = synthetic construct
SEQUENCE: 535
DDDDY                                                              5

SEQ ID NO: 536         moltype = AA  length = 5
FEATURE                Location/Qualifiers
REGION                 1..5
                       note = Component of peptide hormone analogue
source                 1..5
                       mol_type = protein
                       organism = synthetic construct
SEQUENCE: 536
HPFHL                                                              5
```

The invention claimed is:

1. A compound of the structure

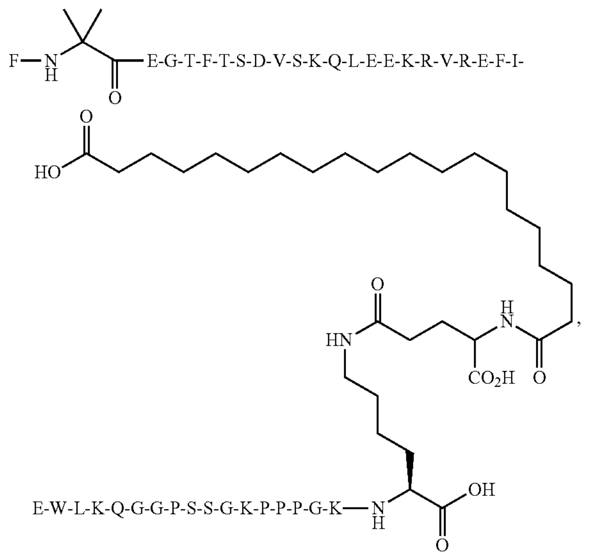

or a pharmaceutically acceptable salt thereof.

2. The compound of claim 1, wherein the compound is in the form of an acetate salt.

3. The compound of claim 1, wherein the compound is in the form of a chloride salt.

4. A pharmaceutical composition comprising a compound of the structure

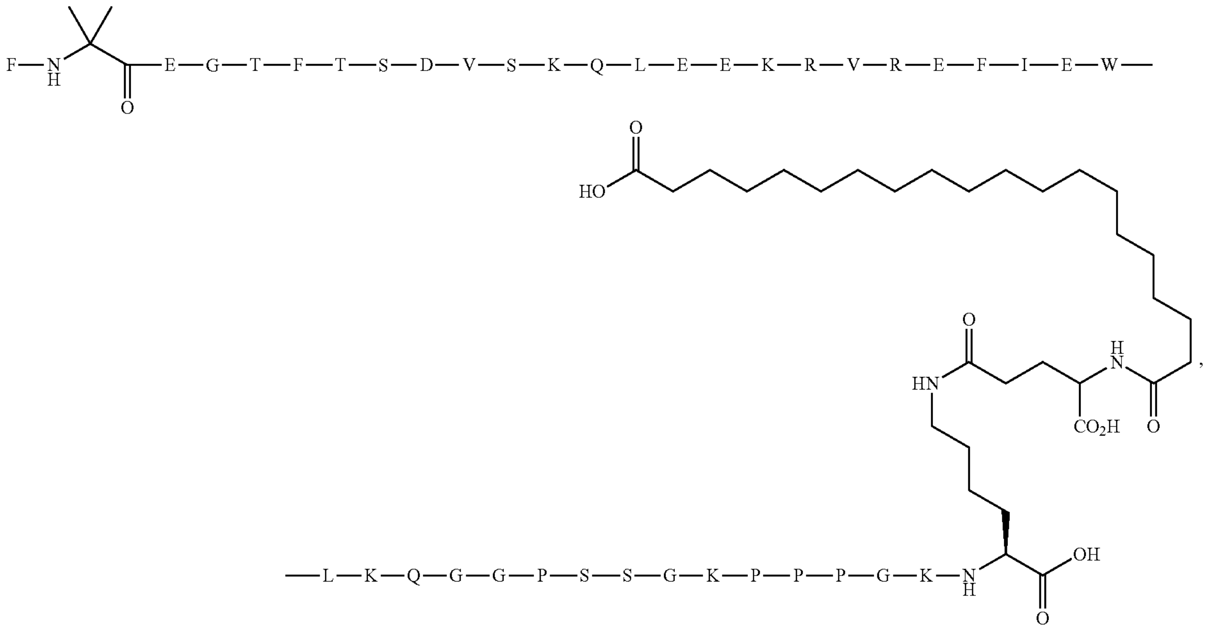

or a pharmaceutically acceptable salt thereof, and a pharmaceutically acceptable excipient.

5. The pharmaceutical composition of claim 4, wherein the compound is in the form of an acetate salt.

6. The pharmaceutical composition of claim 4, wherein the compound is in the form of a chloride salt.

7. The pharmaceutical composition of claim 4, wherein the pharmaceutical composition is in the form of an injectable aqueous solution.

8. The pharmaceutical composition of claim 4, wherein the pharmaceutical composition is present in a syringe or other administration device for subcutaneous administration.

9. A method for inducing or maintaining weight loss or managing body weight in a subject, the method comprising administering to the subject an effective amount of a pharmaceutical composition comprising a compound of the structure

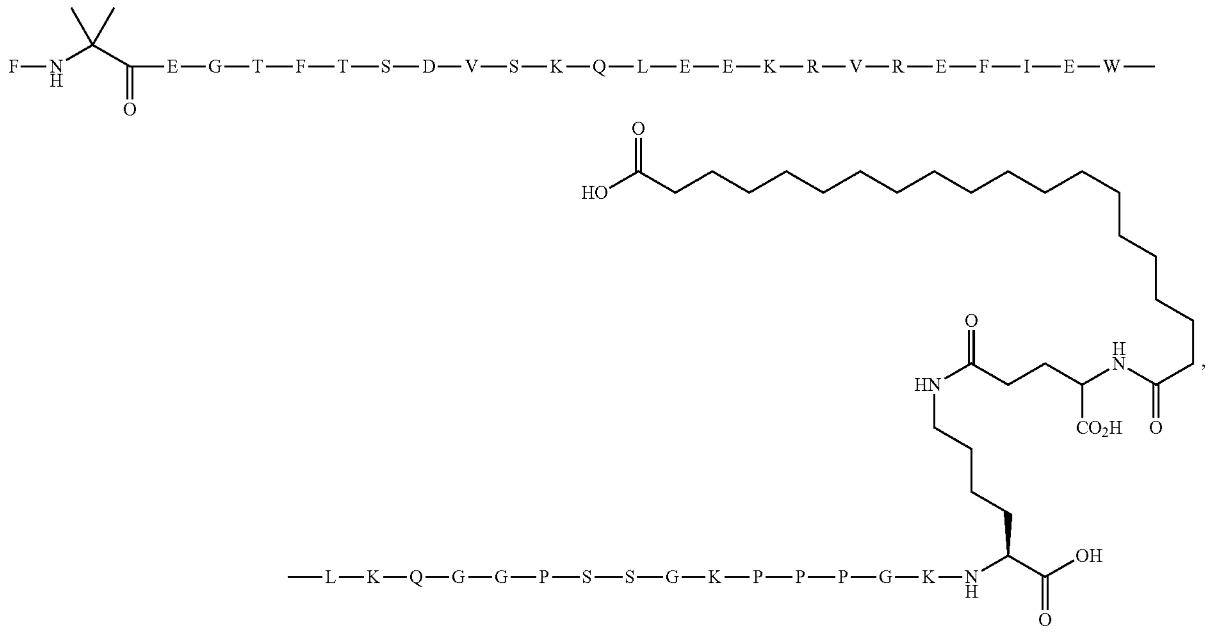

or a pharmaceutically acceptable salt thereof, and a pharmaceutically acceptable excipient.

10. The method of claim 9, wherein the compound is in the form of an acetate salt.

11. The method of claim 9, wherein the compound is in the form of a chloride salt.

12. The method of claim 9, wherein the pharmaceutical composition is in the form of an injectable aqueous solution.

13. The method of claim 9, wherein the pharmaceutical composition is present in a syringe or other administration device for subcutaneous administration.

14. The method of claim 9, wherein the pharmaceutical composition is administered to the subject by subcutaneous administration.

15. A compound comprising a peptide comprising the amino acid sequence of SEQ ID NO: 502, or a pharmaceutically acceptable salt thereof.

16. The compound of claim 15, wherein the compound comprises a lipid moiety linked to the peptide.

17. The compound of claim 16, wherein the lipid moiety is linked to the C-terminal lysine of the peptide.

18. The compound of claim 16, wherein the lipid moiety has a structure of a group of formula:

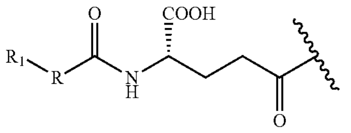

wherein R is a $C_{16}$-$C_{18}$ alkylene or alkenylene group; and $R^1$ is $CO_2H$.

19. The compound of claim 18, wherein R is a $C_{18}$ alkylene group.

20. The compound of claim 15, wherein the compound is in the form of an acetate salt.

21. The compound of claim 15, wherein the compound is in the form of a chloride salt.

22. A pharmaceutical composition comprising the compound of claim 15, and a pharmaceutically acceptable excipient.

23. The pharmaceutical composition of claim 22, wherein the pharmaceutical composition is in the form of an injectable aqueous solution.

24. The pharmaceutical composition of claim 22, wherein the pharmaceutical composition is present in a syringe or other administration device for subcutaneous administration.

* * * * *